US008946382B2

(12) United States Patent
Cuttitta et al.

(10) Patent No.: US 8,946,382 B2
(45) Date of Patent: Feb. 3, 2015

(54) APELIN PEPTIDES AND METHODS OF USE

(75) Inventors: Frank Cuttitta, Adamstown, MD (US); Ingalill Avis, Gaithersburg, MD (US); David Salomon, Frederick, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 707 days.

(21) Appl. No.: 12/715,338

(22) Filed: Mar. 1, 2010

(65) Prior Publication Data

US 2010/0221255 A1    Sep. 2, 2010

Related U.S. Application Data

(60) Provisional application No. 61/156,351, filed on Feb. 27, 2009.

(51) Int. Cl.
| | |
|---|---|
| C07K 14/47 | (2006.01) |
| C07K 16/26 | (2006.01) |
| G01N 33/566 | (2006.01) |
| A61K 38/00 | (2006.01) |

(52) U.S. Cl.
CPC ............. *C07K 14/47* (2013.01); *C07K 16/26* (2013.01); *G01N 33/566* (2013.01); *A61K 38/00* (2013.01)
USPC .......................................................... 530/326

(58) Field of Classification Search
CPC ........................................................ C07K 14/47
USPC ............................................................ 530/326
See application file for complete search history.

(56) References Cited

U.S. PATENT DOCUMENTS 6,492,324 B1   12/2002   Hinuma et al.

OTHER PUBLICATIONS

Ibragimova and Eade (Biophysical Journal, Oct. 1999, vol. 77, pp. 2191-2198).*
Burgess et al, Journal of Cell Biology vol. 111 Nov. 1990 2129-2138.*
Lazar et al Molecular and Cellular Biology Mar. 1988 vol. 8 No. 3 1247-1252.*
Schwartz et al, Proc Natl Acad Sci USA vol. 84:6408-6411 (1987)).*
Lin et al Biochemistry USA vol. 14:1559-1563 (1975)).*
Bianco et al., Cripto-1 Is Required for Hypoxia to Induce Cardiac Differentiation of Mouse Embryonic Stem Cells. *The American Journal of Pathology.* 2009; 175(5):2146-2158.
Bianco et al., Role of Human Cripto-1 in Tumor Angiogenesis. *Journal of the National Cancer Institute.* 2005; 97(2):132-141.
Charles, Putative Role for Apelin in Pressure/Volume Homeostasis and Cardiovascular Disease. *Cardiovascular & Hematological Agents in Medicinal Chemistry.* 2007; 5(1):1-10.
Cuttitta, Peptide Amidation: Signature of Bioactivity. *The Anatomical Record.* 1993; 236:87-93.
D'Aniello et al., G Protein—Coupled Receptor APJ and Its Ligand Apelin Act Downstream of Cripto to Specify Embryonic Stem Cells Toward the Cardiac Lineage Through Extracellular Signal-Regulated Kinase/p70S6 Kinase Signaling Pathway. *Circulation Research.* 2009; 105(3):231-238.
Eberlein et al., Patters of Prohormone Processing. Order Revealed by a New Procholecystokinin-Derived Peptide. *J. Biol. Chem.* 1992; 267(3):1517-1521.
Fenger and Johnsen, α-Amidated peptides derived from pro-opiomelanocortin in normal human pituitary. *Biochem. J.* 1988; 250:781-788.
Habata et al., Apelin, the natural ligand of the orphan receptor APJ, is abundantly secreted in the colostrum. *Biochimica et Biophysica Acta.* 1999 1452(1):25-35.
Hosoya et al., Molecular and Functional Characteristics of APJ. Tissue Distribution of mRNA and Interaction with the Endogenous Ligand Apelin. *J. Biol. Chem.* 2000; 275(28):21061-21067.
Jonas et al., Alternative RNA processing events in human calcitonin/calcitonin gene-related peptide gene expression. *Proc. Natl. Acad. Sci. USA.* 1985; 82:1994-1998.
Kälin et al., Paracrine and autocrine mechanisms of apelin signaling govern embryonic and tumor angiogenesis. *Dev. Biol.* 2007; 305(2):599-614.
Kunduzova et al., Apelin/APJ signaling system: a potential link between adipose tissue and endothelial angiogenic processes. *The FASEB Journal.* 2008; 22(12):4146-4153.
Lee et al., Characterization of Apelin, the Ligand for the APJ Receptor. *J. Neurochem.* 2000; 74(1): 34-41.
Lee et al., Modification of the Terminal Residue of Apelin-13 Antagonizes Its Hypotensive Action. *Endocrinology.* 2005; 146(1):231-236.
Martínez et al., Identification of Vasoactive Nonpeptidic Positive and Negative Modulators of Adrenomedullin Using a Neutralizing Antibody-Based Screening Strategy. *Endocrinology.* 2004; 145(8):3858-3865.
Masri et al., Apelin (65-77) activates p70 S6 kinase and is mitogenic for umbilical endothelial cells. *The FASEB Journal.* 2004; 18(15):1909-1911.
Masri et al., The Apelin Receptor is Coupled to $G_{i1}$ or $G_{i2}$ Protein and is Differentially Desensitized by Apelin Fragments. *J. Biol. Chem.* 2006; 281(27):18317-18326.
Ørskov et al., Complete Sequences of Glucagon-like Peptide-1 from Human and Pig Small Intestine. *J. Biol. Chem.* 1989; 264(22):12826-12829.
Pritchard et al., Minireview: Neuropeptide Processing and Its Impact on Melanocortin Pathways. *Endocrinology.* 2007; 148(9):4201-4207.

(Continued)

*Primary Examiner* — Lynn Bristol
(74) *Attorney, Agent, or Firm* — Klarquist Sparkman, LLP

(57) ABSTRACT

The present disclosure concerns the use of biologically active apelin peptides and compositions that are processed from larger precursor proteins and further post-translationally modified to influence cell growth. Particular methods are useful for promoting cell growth, while others are particularly useful for inhibiting cell growth.

3 Claims, 18 Drawing Sheets

(56) References Cited

OTHER PUBLICATIONS

Quinn et al., α-Amidation of Peptide Hormones in Lung Cancer. *Cancer Cells.* 1991; 3(12): 504-510.

Rotwein et al., Biosynthesis of Human Insulin-like Growth Factor I (IGF-I). *J. Biol. Chem.* 1987; 262(24):11807-11812.

Siegfried et al., A mitogenic peptide amide encoded within the E peptide domain of the insulin-like growth factor IB prohormone. *Proc. Natl. Acad. Sci. USA.* 1992; 89:8107-8111.

Sorli et al., Apelin is a potent activator of tumour neoangiogenesis. *Oncogene.* 2007; 26:7692-7699.

Strizzi et al., Emerging Roles of Nodal and Cripto-1: From Embryogenesis to Breast Cancer Progression. *Breast Disease.* 2008; 29:91-103.

Szokodi et al., Apelin, the Novel Endogenous Ligand of the Orphan Receptor APJ, Regulates Cardiac Contractility. *Circ. Res.* 2002; 91:434-440.

Tatemoto et al., Isolation and Characterization of a Novel Endogenous Peptide Ligand for the Human APJ Receptor. *Biochemical and Biophysical Research Communications.* 1998; 251:471-476.

Wang et al., Immunohistochemical localization of apelin in human normal breast and breast carcinoma. *J. Mol. Hist.* 2008; 39:121-124.

Watanabe et al., Growth Factor Induction of Cripto-1 Shedding by Glycosylphosphatidylinositol-Phospholipase D and Enhancement of Endothelial Cell Migration. *The Journal of Biological Chemistry.* 2007; 282(43):31643-31655.

Zeng et al., Apelin and Its Receptor Control Heart Field Formation during Zebrafish Gastrulation. *Dev. Cell.* 2007; 12:391-402.

Cuttitta et al., Peptide physiology of human cancer cells and its relationship with autocrine/paracrine growth. In Julia M. Polak (editor) *Diagnostic Histopathology of Neuroendocrine Tumours.* Churchill Livingstone, New York, pp. 15-39, 1993.

\* cited by examiner

FIG. 1
Alignment of Human Apelin Peptides

Human Apelin-36 (42-77) (SEQ ID NO: 15)    L-V-Q-P-R-G-S-R-N-G-P-G-P-W-Q-G-G-R-R-K-F-R-R-Q-R-P-R-L-S-H-K-G-P-M-P-F Human Apelin-17 (61-77) (SEQ ID NO: 16)                                                  K-F-R-R-Q-R-P-R-L-S-H-K-G-P-M-P-F Human Apelin-13 (65-77) (SEQ ID NO: 17)                                                              Q-R-P-R-L-S-H-K-G-P-M-P-F Human Apelin-36 (42-57) [Salcut]            L-V-Q-P-R-G-S-R-N-G-P-G-P-W-Q-G          (SEQ ID NO: 18)

Human Apelin-36 (42-57) [Salcut-amide]      L-V-Q-P-R-G-S-R-N-G-P-G-P-W-Q-G-NH$_2$   (SEQ ID NO: 19)

Human Apelin-36 (42-58) [Salcut-glycine]    L-V-Q-P-R-G-S-R-N-G-P-G-P-W-Q-G-G        (SEQ ID NO: 20)

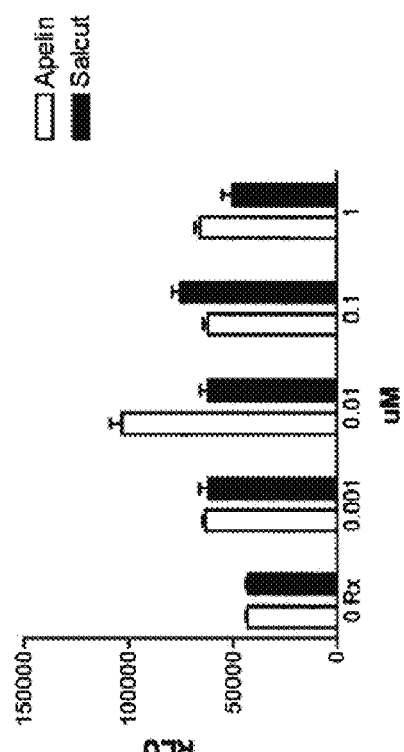
FIG. 3I  Human Lymphatic EC (LEC) 3 day incubation
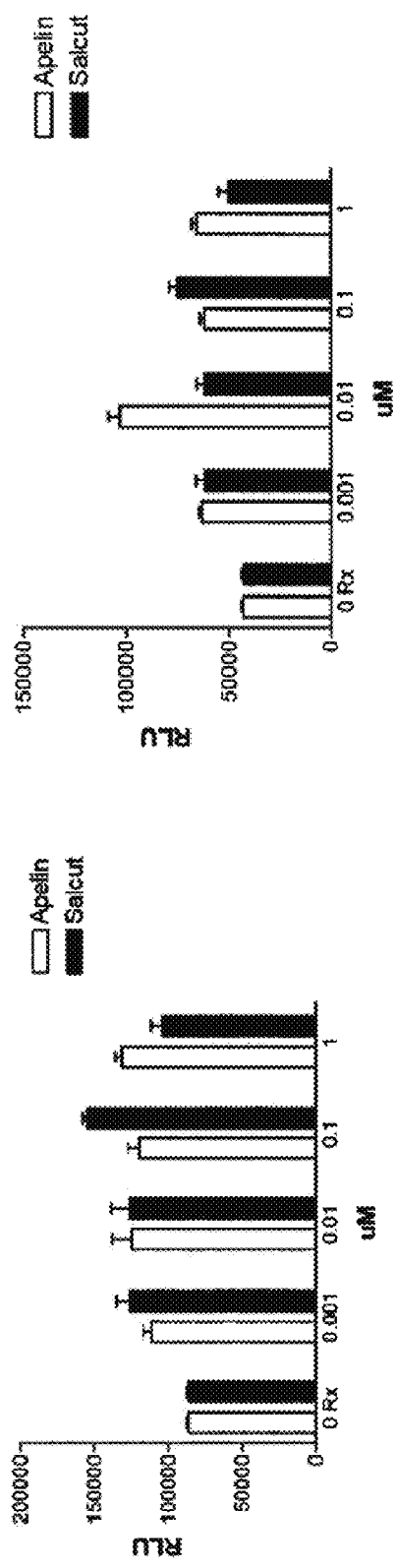
FIG. 3J  Human Lymphatic EC (LEC) 5 day incubation
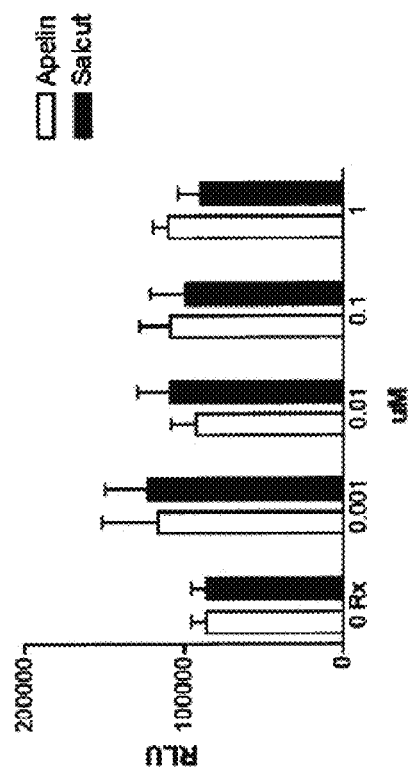
FIG. 3K  Monkey EC (CRL 1780)

**3-18-08 HTB 103
Salcut**

**3-18-08 HTB 103
Apelin**

Salcut-NH2 Induced Growth Regulation (Stimulation/Suppression) of Human Tumor Cell Lines Over 1nM to 1uM Dose Range Salcut-NH2 Induced Growth Regulation (Stimulation/Suppression) of Human Tumor Cell Lines Over 0.1nM to 2.0/10uM Dose Range Salcut-NH2 and Derivatives Induced Growth Regulation (Stimulation/Suppression) of Human Blood Vessel Endothelial Cell Line (HMEC-1) Over 1nM to 1uM Dose Range Salcut-NH2 Induced Aortic Ring/Vessel Outcropping
- Dose Response Curve -

Elisa Titration Curve Using Different Absorption Peptides And Different Solid Phased Ligand Targets Effects of Salcut-NH2 Treatment on Nude Mouse Xenograft Growth of the Human Bronchioloalveolar CA Cell Line A549

Apelin-13(F13A) Antagonist Blocks Apelin-13 Induced Proliferation But Not Salcut-NH2 Mediated Growth

APL(F/A) = Apelin-13(F13A), Apelin-13 Peptide Antagonist
RLU = Relative Luminescent Units

US 8,946,382 B2

APELIN PEPTIDES AND METHODS OF USE

CROSS REFERENCE TO RELATED APPLICATION

This application claims the benefit of U.S. Provisional Application No. 61/156,351, filed Feb. 27, 2009, which is incorporated herein by reference.

FIELD OF THE DISCLOSURE

This disclosure relates to the field of biologically active peptides that are processed from larger precursor proteins and further post-translationally modified. This disclosure also related to methods of use of such post-translationally modified peptides, for example for inhibiting cell growth or for enhancing cell growth.

BACKGROUND

Biologically active peptides are generally first synthesized as inactive, higher molecular weight precursors. Processing of a proprotein precursor, by enzymatic cleavage and covalent modifications, yields active peptide(s) from the larger proprotein. It is not uncommon for a proprotein to be processed such that more than one biologically active peptide is produced from the same precursor molecule. For example, cholecystokinin, proopiomelanocortin, calcitonin, proglucagon, and proadrenomedulin each produce several different biologically active peptides.

Amidation is often a biologically important post-translational modification, as the amidated form of a protein generally is biologically active and more resistant to carboxypeptidases. An amidation motif has been used to identify potential cleavage/amidation sites in precursor proteins which may result in the generation of biologically active amidated peptides from a precursor protein (see, for example, Eberlein et al., *J. Biol. Chem.*, 267:1517-1521, 1992; Siegfried et al., *Proc. Natl. Acad. Sci. USA*, 89:8107-8111, 1992; Quinn et al., *Cancer Cells*, 3:504-510, 1991; Cuttitta, *The Anatomical Record*, 236:87-93, 1993; Fenger and Johnsen, *Biochem. J.*, 250:781-788, 1988; Orskov et al., *J. Biol. Chem.*, 264:12826-12829, 1989). The amidation motif consists of an invariant glycine residue followed by a region of basic amino acids on the carboxy-terminal side of the glycine residue.

Although the free acid and amidated forms of a peptide are difficult to distinguish structurally, the amide can be 100-1000 times more biologically active than the free acid form of the peptide (Cuttitta, *The Anatomical Record*, 236:87-93, 1993). Amidated peptides can exhibit the same type of biological activity as other peptides processed from the same precursor protein, although their activity may vary with peptide size (Tatemoto et al., *Biochem. Biophys. Res. Comm.*, 251:471-476, 1998).

SUMMARY OF THE DISCLOSURE

This disclosure provides apelin-36 (42-57) peptide (also known as salcut) and variants thereof, and nucleic acid molecules encoding these peptides, including cDNA sequences. In specific embodiments, these amino acid sequences are post-translationally modified, for example into an amide-derived form. The amide-derived form of apelin-36 (42-57) (also known as salcut-$NH_2$) has both cell growth enhancing and inhibiting activity; depending for instance on dosage. Thus, the molecules and compounds disclosed herein are useful for modifying angiogenesis. In addition, the molecules disclosed herein are useful for inhibiting or treating tumor cell growth.

The molecules provided herein are further useful for ameliorating, treating, detecting, prognosing, and diagnosing diseases and conditions associated with abnormal apelin-36 (42-57) levels, or more specifically abnormal amidated apelin-36 (42-57) levels, such as neoplasia, hypertension, preeclampsia syndrome, diabetes, ocular degeneration, idiopathic pulmonary fibrosis, wound healing, abnormal angiogenesis, altered mast cell migration, chronic obstructive pulmonary disease, inflammatory diseases such as arthritis (juvenile and rheumatoid) and inflammatory bowel disease, cardiovascular disease, avascular or ischemic insult, myocardial infarction, stroke, vasculititis/angiitis, systemic or vascular sclerosis, gangrene, congelation (severe frostbite), alopecia, eczema, ulcers, lymphedema (parasite induced, for example elephantiasis/elephantitis, or tumor induced), vascular hyperplasia, hemangioma, diabetic induced retinopathy, macular degenerative disease, psoriasis, endometriosis, among others.

In some embodiments the disclosed molecules are used for quantitating apelin-36 (42-57) levels, or more specifically amidated apelin-36 (42-57) levels, in biological samples, such as samples from cancer patients, in order to measure the severity of the disease state. Antibodies specific for apelin-36 (42-57) can be used to screen samples for the presence and quantity of the disclosed peptides.

Also provided herein are inhibitors or antagonists of amidated apelin-36 (42-57), for example apelin-36 (42-58) (also referred to as salcut-Gly), free-acid form of apelin-36 (42-57), small molecule inhibitors, and neutralizing monoclonal antibodies. Activators of amidated apelin-36 (42-57) are also provided herein.

The foregoing and other features and advantages of the invention will become more apparent from the following detailed description of a several embodiments which proceeds with reference to the accompanying figures.

BRIEF DESCRIPTION OF THE FIGURES

FIG. 1 illustrates amino acid sequences of apelin peptides; these are aligned to assist in comparisons.

FIG. 3 is a series of graphs demonstrating the proliferative response of various endothelial cells and epithelial cells to various concentrations of apelin-13 (65-77), apelin-36 (42-57) (salcut), the free acid form of apelin-36 (42-57) (salcut-OH), or apelin-36 (42-58) (salcut-glycine). FIG. 3I shows the proliferative response of the human lymphatic endothelial cell line after a three day incubation in the presence of both apelin-13 (65-77) and apelin 36 (42-57). FIG. 3J shows the proliferative response of the human lymphatic endothelial cell line after a five day incubation in the presence of both apelin-13 (65-77) and apelin 36 (42-57). FIG. 3K shows the proliferative response of the CRL 1780 monkey endothelial cell line in the presence of both apelin-13 (65-77) and apelin 36 (42-57).

FIG. 4A shows a biphasic response curve of apelin 36 (42-57) on the MCF-7 human breast cancer cell line. FIG. 4B shows a lack of a statistically significant proliferative response of the A549 cells to various concentrations of apelin 36 (42-57), although there appears to be a downward trend (inhibition) in proliferation with increased concentration of apelin 36 (42-57). The resulting biphasic response curve is indicative of either cell toxicity at a higher dose range or a two receptor system (high affinity receptor-mediating proliferation and low affinity receptor inducing growth suppression; a homeostatic feedback mechanism).

FIGS. 5A and 5B show biphasic response curves of the HMC-1 human mast cell line and HTB 103 human gastric cancer cell line, respectively. The resulting biphasic response curve is indicative of either cell toxicity at a higher dose range or a two receptor system (high affinity receptor-mediating proliferation and low affinity receptor inducing growth suppression; a homeostatic feedback mechanism).

FIG. 6A shows a biphasic response curve of the HMEC-1 cells to apelin 36 (42-57). FIG. 6B shows that salcut OH and salcut Gly have no effect on HMEC-1 cell proliferation. The resulting biphasic response curve is indicative of either cell toxicity at a higher dose range or a two receptor system (high affinity receptor-mediating proliferation and low affinity receptor inducing growth suppression; a homeostatic feedback mechanism). Salcut-OH (free-acid) and the salcut-Gly (glycine extended) derivative are non-responsive over the dose range tested.

FIG. 13 is a series of graphs demonstrating that the apelin-13(F13A) antagonist blocks apelin-13 induced proliferation but not salcut-NH2 mediated growth.

FIG. 14 is a series of graphs showing the proliferative response of the human breast cancer cell line MDA-MB43 to various concentrations of salcut-NH2 and biotinylated salcut.

SEQUENCE LISTING

Figure 2:
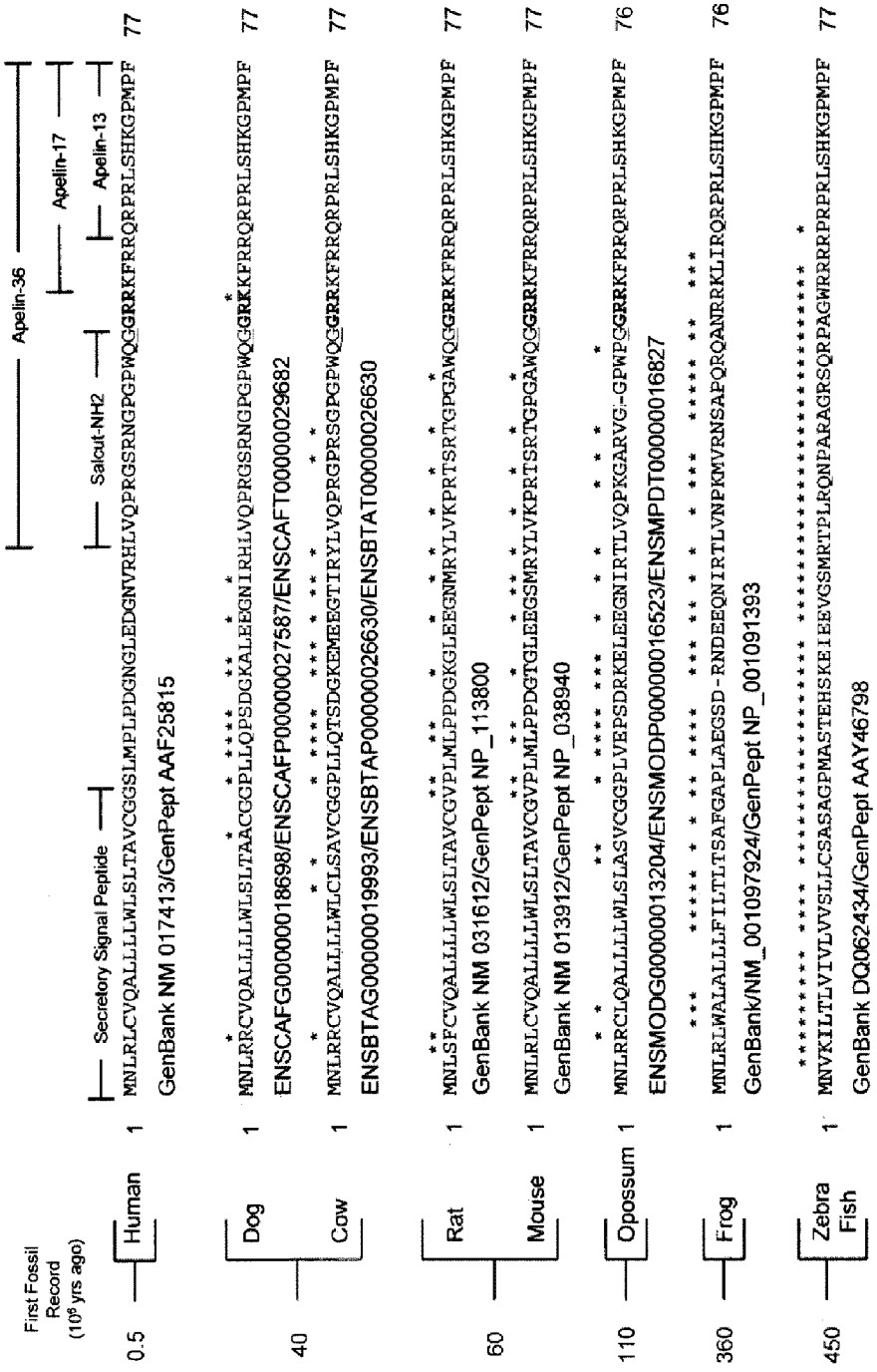
FIG. 2 is an alignment of the amino acid sequences of human (SEQ ID NO: 8), dog (SEQ ID NO: 9), bovine (SEQ ID NO: 10, rat (SEQ ID NO: 11), mouse (SEQ ID NO: 12), opossum (SEQ ID NO: 13), frog (SEQ ID NO: 37), and zebra fish (SEQ ID NO: 14) apelin preproprotein, demonstrating the evolutionary conservation of apelin in mammals. Also shown are the regions of apelin which correspond to the secretory signal peptide (residues 1-22), apelin-36 (42-77), apelin-17 (61-77), apelin-13 (65-77), and salcut-$NH_2$/apelin-36 (42-57). Accession numbers for the gene, cDNA, or protein sequences for each species are identified.

The nucleic and amino acid sequences listed herein and/or herewith are shown using standard letter abbreviations for nucleotide bases, and three letter code for amino acids, as defined in 37 C.F.R. §1.822. Only one strand of each nucleic acid sequence is shown, but the complementary strand is understood as included by any reference to the displayed strand.

SEQ ID NO: 1 shows the cDNA sequence of the human apelin preproprotein, also presented as positions 308-541 of GenBank Accession No. NM_017413.

SEQ ID NO: 2 shows the cDNA sequence of the dog apelin preproprotein, also presented as Ensembl Accession No. ENSCAFT00000029682.

SEQ ID NO: 3 shows the cDNA sequence of the bovine apelin preproprotein, also presented as GenBank Accession No. NM_174503 or Ensembl Accession No. ENSBTAT00000026630.

SEQ ID NO: 4 shows the cDNA sequence of the rat apelin preproprotein, also presented as positions 327-560 of GenBank Accession No. NM_031612.

SEQ ID NO: 5 shows the cDNA sequence of the mouse apelin preproprotein, also presented as positions 348-581 of GenBank Accession No. NM_013912.

SEQ ID NO: 6 shows the cDNA sequence of the opossum apelin preproprotein, also presented as Ensembl Accession No. ENSMODT00000016827.

SEQ ID NO: 7 shows the cDNA sequence of the zebra fish apelin preproprotein, also presented as positions 73-306 of GenBank Accession No. DQ062434.

SEQ ID NO: 8 shows the amino acid sequence of the human apelin preproprotein, also presented as GenBank Accession No. NP_059109 or Accession No. AAF25815.

SEQ ID NO: 9 shows the amino acid sequence of the dog apelin preproprotein, also presented as Ensembl Accession No. ENSCAFP00000027587.

SEQ ID NO: 10 shows the amino acid sequence of the bovine apelin preproprotein, also presented as GenBank Accession No. NP_776928 or Ensembl Accession No. ENSBTAP00000026630.

SEQ ID NO: 11 shows the amino acid sequence of the rat apelin preproprotein, also presented as GenBank Accession No. NP_113800.

SEQ ID NO: 12 shows the amino acid sequence of the mouse apelin preproprotein, also presented as GenBank Accession No. NP_038940.

SEQ ID NO: 13 shows the amino acid sequence of the opossum apelin preproprotein, also presented as Ensembl Accession No. ENSMODP00000016523.

SEQ ID NO: 14 shows the amino acid sequence of the zebra fish apelin preproprotein, also presented as GenBank Accession No. AAY46798.

SEQ ID NO: 15: shows the amino acid sequence of human apelin-36.

SEQ ID NO: 16 shows the amino acid sequence of human apelin-17.

SEQ ID NO: 17 shows the amino acid sequence of human apelin-13.

SEQ ID NO: 18 shows the amino acid sequence of human apelin-36 (42-57), also known as human salcut or salcut-OH (the free-acid derivative of salcut).

SEQ ID NO: 19 shows the amino acid sequence of the amide derivative of human apelin-36 (42-57), also known as human salcut-$NH_2$.

SEQ ID NO: 20 shows the amino acid sequence of a glycine-extended form of human apelin-36 (42-57), also known as human salcut-Gly or human apelin-36 (42-58).

SEQ ID NO: 21 shows the amino acid sequence of dog apelin-36 (42-57), also known as dog salcut or salcut-OH (the free-acid derivative of salcut).

SEQ ID NO: 22 shows the amino acid sequence of the amide derivative of dog apelin-36 (42-57), also known as dog salcut-$NH_2$.

SEQ ID NO: 23 shows the amino acid sequence of a glycine-extended form of dog apelin-36 (42-57), also known as dog salcut-Gly or dog apelin-36 (42-58).

SEQ ID NO: 24 shows the amino acid sequence of bovine apelin-36 (42-57), also known as bovine salcut or salcut-OH (the free-acid derivative of salcut).

SEQ ID NO: 25 shows the amino acid sequence of the amide derivative of bovine apelin-36 (42-57), also known as bovine salcut-$NH_2$.

SEQ ID NO: 26 shows the amino acid sequence of a glycine-extended form of bovine apelin-36 (42-57), also known as bovine salcut-Gly or bovine apelin-36 (42-58).

SEQ ID NO: 27 shows the amino acid sequence of rat apelin-36 (42-57), also known as rat salcut or salcut-OH (the free-acid derivative of salcut).

SEQ ID NO: 28 shows the amino acid sequence of the amide derivative of rat apelin-36 (42-57), also known as rat salcut-$NH_2$.

SEQ ID NO: 29 shows the amino acid sequence of a glycine-extended form of rat apelin-36 (42-57), also known as rat salcut-Gly or rat apelin-36 (42-58).

SEQ ID NO: 30 shows the amino acid sequence of mouse apelin-36 (42-57), also known as mouse salcut or salcut-OH (the free-acid derivative of salcut).

SEQ ID NO: 31 shows the amino acid sequence of the amide derivative of mouse apelin-36 (42-57), also known as mouse salcut-$NH_2$.

SEQ ID NO: 32 shows the amino acid sequence of a glycine-extended form of mouse apelin-36 (42-57), also known as mouse salcut-Gly or mouse apelin-36 (42-58).

SEQ ID NO: 33 shows the amino acid sequence of opossum apelin-36 (42-57), also known as opossum salcut or salcut-OH (the free-acid derivative of salcut).

SEQ ID NO: 34 shows the amino acid sequence of the amide derivative of opossum apelin-36 (42-57) (based on the numbering of the human apelin sequence), also known as opossum salcut-$NH_2$.

SEQ ID NO: 35 shows the amino acid sequence of a glycine-extended form of opossum apelin-36 (42-57), also known as opossum salcut-Gly or opossum apelin-36 (42-58) (based on the numbering of the human apelin sequence).

SEQ ID NO: 36 shows the cDNA sequence of the frog apelin preproprotein, also referred to as positions 97-327 of GenBank Accession No. NM_001097924.

SEQ ID NO: 37 shows the amino acid sequence of the frog apelin preproprotein, also referred to as GenBank Accession No. NP_001091393.

SEQ ID NO: 38 shows cysteine linked salcut-$NH_2$.

SEQ ID NO: 39 shows the cDNA sequence of the rhesus monkey apelin preproprotein, also presented as Ensembl Accession No. ENSMMUT00000003625.

SEQ ID NO: 40 shows the amino acid sequence of the rhesus monkey apelin preproprotein, also presented as Ensembl Accession No. ENSMMUP00000003428.

SEQ ID NO: 41 shows the amino acid sequence of rhesus monkey apelin-36 (42-57), also known as rhesus monkey salcut or salcut-OH (the free-acid derivative of salcut).

SEQ ID NO: 42 shows the amino acid sequence of the amide derivative of rhesus monkey apelin-36 (42-57), also known as rhesus monkey salcut-$NH_2$.

SEQ ID NO: 43 shows the amino acid sequence of a glycine-extended form of rhesus monkey apelin-36 (42-57), also known as rhesus monkey salcut-Gly or rhesus monkey apelin-36 (42-58).

DETAILED DESCRIPTION OF SEVERAL EMBODIMENTS

I. Abbreviations

CA Cancer
EC Endothelial cell
ELISA Enzyme-Linked ImmunoSorbent Assay
GFP Green Fluorescent Protein
HMC Human Mast Cell
HMEC Human microvascular endothelial cell
LEC Lymphatic endothelial cell
PAE Porcine aortic endothelial cell
RLU Relative Luminescent Units

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Amidation or amide derivative: A post-translational modification that leads to biological activity of an otherwise inert peptide or that enhances the biological activity of the peptide, wherein a peptide is post-translationally modified by C-terminal amidation. The amino acid to be modified is always followed by a glycine, which provides the amide group. The process of post-translational amidation of a peptide derived from a precursor proprotein is well characterized and involves three enzymatic steps (Cuttitta, *The Anatomical Record*, 236: 87-93, 1993). Step one involves endoproteolytic cleavage at a pair of basic amino acids near the carboxy terminus of the protein. Step two involves carboxypeptidase-mediated removal of basic residues. Step three is the amidation reaction, which involves oxidation of a terminal glycine to form the amide of the neighboring carboxy terminal amino acid. Glycine is the only known amino acid to function as an amide donor for its neighboring amino acid. Although the free acid and amidated forms of a peptide are difficult to distinguish structurally, the amide can be 100-1000 times more biologically active than the free acid form of the peptide (Cuttitta, *The Anatomical Record*, 236:87-93, 1993). C-terminal amidation is essential to the biological activity of many polypeptides, including neuropeptides and hormones.

Animal: Living multicellular organisms, a category which includes, for example, mammals, for example humans, and birds.

Antibody: Immunoglobulin (Ig) molecules and immunologically active portions of Ig molecules, for instance, molecules that contain an antigen binding site which specifically binds (immunoreacts with) an antigen. In one embodiment the antigen is CD34. Monoclonal, polyclonal, and humanized immunoglobulins are encompassed by the disclosure. The disclosure also includes synthetic and genetically engineered variants of these immunoglobulins.

A naturally occurring antibody (for example, IgG) includes four polypeptide chains, two heavy chains and two light chains inter-connected by disulfide bonds. However, it has been shown that the antigen-binding function of an antibody can be performed by fragments of a naturally occurring antibody. Thus, these antigen-binding fragments are also intended to be designated by the term "antibody". Examples of binding fragments encompassed within the term antibody include (i) an Fab fragment consisting of the variable light (VL), variable heavy (VH), constant light (CL) and constant heavy (CH)1 domains; (ii) an Fd fragment consisting of the VH and CH1 domains; (iii) an Fv fragment consisting of the VL and VH domains of a single arm of an antibody, (iv) a dAb fragment (Ward et al., (1989) *Nature* 341:544-546) which consists of a VH domain; and (v) an F(ab')$_2$ fragment, a bivalent fragment comprising two Fab fragments linked by a disulfide bridge at the hinge region. Furthermore, although the two domains of the Fv fragment are coded for by separate genes, a synthetic linker can be made that enables them to be made as a single protein chain (known as single chain Fv (scFv); Bird et al. (1988) *Science* 242:423-426; and Huston et al. (1988) *Proc. Natl. Acad. Sci.* 85:5879-5883) by recombinant methods. Such single chain antibodies, as well as dsFv, a disulfide stabilized Fv (Bera et al. (1998) *J. Mol. Biol.* 281:475-483), and dimeric Fvs (diabodies), that are generated by pairing different polypeptide chains (Holliger et al. (1993) *Proc. Natl. Acad. Sci.* 90:6444-6448), are also included.

In one embodiment, antibody fragments for use in this disclosure are those which are capable of cross-linking their target antigen, for example, bivalent fragments such as F(ab')$_2$ fragments. Alternatively, an antibody fragment which does not itself cross-link its target antigen (for example, a Fab fragment) can be used in conjunction with a secondary antibody which serves to cross-link the antibody fragment, thereby cross-linking the target antigen. Antibodies can be fragmented using conventional techniques and the fragments screened for utility in the same manner as described for whole antibodies. An antibody is further intended to include humanized monoclonal molecules that specifically bind the target antigen.

"Specifically binds" refers to the ability of individual antibodies to specifically immunoreact with an antigen. This binding is a non-random binding reaction between an antibody molecule and the antigen. In one embodiment, the antigen is CD34. Binding specificity is typically determined from the reference point of the ability of the antibody to differentially bind the antigen of interest and an unrelated antigen, and therefore distinguish between two different antigens, particularly where the two antigens have unique epitopes. An antibody that specifically binds to a particular epitope is referred to as a "specific antibody".

A variety of methods for attaching detectable labels to antibodies are well known in the art. Detectable labels useful for such purposes are also well known in the art, and include radioactive isotopes such as $^{32}$P, fluorophores, chemiluminescent agents, and enzymes.

Antigen: Any molecule that can bind specifically with an antibody. An antigen is also a substance that antagonizes or stimulates the immune system to produce antibodies. Antigens are often foreign substances such as allergens, bacteria or viruses that invade the body.

Antisense, Sense, and Antigene: Double-stranded DNA (dsDNA) has two strands, a 5'→3' strand, referred to as the plus strand, and a 3'→5' strand (the reverse complement), referred to as the minus strand. Because RNA polymerase adds nucleic acids in a 5'→3' direction, the minus strand of the DNA serves as the template for the RNA during transcription.

Thus, the RNA formed will have a sequence complementary to the minus strand and identical to the plus strand (except that U is substituted for T).

Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a dsDNA target.

Apelin: The apelin gene has been identified in various species, including human, dog, bovine, rat, mouse, rhesus monkey, and zebra fish and codes for an apelin preproprotein of 77 amino acids (also referred to herein as apelin (1-77)). In processing the apelin preproprotein, a signal peptide corresponding to residues 1-22 of the apelin preproprotein is cleaved off, resulting in a 55 amino acid (residues 23-77) apelin proprotein (also referred to herein as apelin (23-77)). Apelin-36 is a 36 amino acid long peptide derived from the 55 amino acid long apelin (23-77) proprotein (Tatemoto et al., *Biochem. Biophys. Res. Comm.*, 251:471-476, 1998) and corresponds to residues 42-77 of the preproprotein (also referred to herein as apelin-36 (42-77). Apelin-17 and apelin-13 are derived from the carboxy (C)-terminal end of apelin. Apelin-17 corresponds to residues 61-77 of the apelin proprotein and is also referred to as apelin-17 (61-77). Apelin-13 corresponds to residues 65-77 of the apelin proprotein and is also referred to as apelin-13 (65-77). Salcut (also referred to as apelin-36 (42-57) or salcut-OH) is an apelin peptide derived from residues 42-77 of the apelin proprotein or the 16 amino acids from the amino terminal end of apelin-36 (42-77). Salcut can be modified, for example by amidation or addition of a glycine residue at the carboxy-terminal end of the peptide. In frogs and opossum, apelin is 76 amino acids long (also referred to herein as apelin (1-76)).

APJ receptor (apelin receptor): A member of the seven-transmembrane-domain G-protein receptor family; this receptor is structurally related to the angiotensin II receptor type I (ATIR). Apelin-36 (42-77), apelin-17 (61-77), and apelin-13 (65-77) all have a carboxy terminal phenylalanine residue and can bind the APJ receptor. A peptide antagonist version of apelin-13 (65-77), (Ala-13)-Apelin-13 (Lee et al., *Endocrinology*, 146:231-236, 2005), has an alanine residue substituted for the carboxy terminal phenylalanine. (Ala-13)-Apelin-13 binds to the APJ receptor but does not stimulate APJ receptor activity.

Binding or stable binding: An oligonucleotide binds or stably binds to a target nucleic acid if a sufficient amount of the oligonucleotide forms base pairs or is hybridized to its target nucleic acid, to permit detection of that binding. Binding can be detected by either physical or functional properties of the target:oligonucleotide complex. Binding between a target and an oligonucleotide can be detected by any procedure known to one skilled in the art, including both functional and physical binding assays. Binding may be detected functionally by determining whether binding has an observable effect upon a biosynthetic process such as expression of a coding sequence, DNA replication, transcription, amplification and the like.

Physical methods of detecting the binding of complementary strands of DNA or RNA are well known in the art, and include such methods as DNase I or chemical footprinting, gel shift and affinity cleavage assays, Northern blotting, dot blotting and light absorption detection procedures. For example, one method that is widely used, because it is so simple and reliable, involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and target disassociate from each other, or melt.

The binding between an oligomer and its target nucleic acid is frequently characterized by the temperature ($T_m$) (under defined ionic strength and pH) at which 50% of the target sequence remains hybridized to a perfectly matched probe or complementary strand. A higher ($T_m$) means a stronger or more stable complex relative to a complex with a lower ($T_m$).

Other art-recognized forms of stable binding occur between an antibody and antigen, a receptor and ligand, a binding protein and ligand, an enzyme and substrate, and a lectin and a carbohydrate (see, for example, Pio et al, *J. Biol. Chem.*, 276:12292-12300, 2001). Such interactions can be used as tools to measure activators or inhibitors of activity (for example, salcut cell growth modulator activity). In one embodiment, a receptor-trap, wherein a soluble receptor or binding protein binds ligand so that the ligand is no longer available to bind to its cognate receptor, is used as a measure of binding or stability of binding. In another embodiment, depending on type of glycosylation, for example on a receptor (such as a salcut receptor), a lectin would block or enhance ligand (such as salcut) binding.

Cell growth (proliferation): Relates to growth in cell populations or cell number by means of cell reproduction or division. Cell growth can be modulated by an agent, or a combination of agents, in order to enhance, stimulate, or increase cell growth (increase the number of cells in a population) or inhibit, decrease cell growth (maintain or decrease the number of cells in a population). An increase or decrease in cell growth or proliferation can be quantified using any method known to those of skill in the art. An increase or decrease in cell growth can be expressed as a statistically significant change in the number or percentage of cells in a cell population in the presence of an agent or combination of agents, compared to the same cell population in the absence of the agent or combination of agents. cDNA (complementary DNA): A piece of DNA lacking internal, non-coding segments (introns) and transcriptional regulatory sequences. cDNA may also contain untranslated regions (UTRs) that are responsible for translational control in the corresponding RNA molecule. cDNA is usually synthesized in the laboratory by reverse transcription from messenger RNA extracted from cells or other samples.

DNA (deoxyribonucleic acid): DNA is a long chain polymer which comprises the genetic material of most living organisms (some viruses have genes comprising ribonucleic acid (RNA)). The repeating units in DNA polymers are four different nucleotides, each of which comprises one of the four bases, adenine (A), guanine (G), cytosine (C), and thymine (T) bound to a deoxyribose sugar to which a phosphate group is attached. Triplets of nucleotides (referred to as codons) code for each amino acid in a polypeptide, or for a stop signal. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a specific protein, or a fragment thereof, encompasses both the sense strand and its reverse complement. Thus, for instance, it is appropriate to generate probes or primers from the reverse complement sequence of the disclosed nucleic acid molecules.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ concentration) of the hybridization buffer will determine the stringency of hybridization, though waste times also influence stringency. Calculations regarding hybridization conditions required for attaining particular degrees of stringency are discussed by Sambrook et al. (ed.), *Molecular Cloning: A Laboratory Manual,* 2nd ed., vol. 1-3, Cold Spring Harbor Laboratory Press, Cold Spring Harbor, N.Y., 1989, chapters 9 and 11, herein incorporated by reference.

For present purposes, "stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize.

Injectable composition: A pharmaceutically acceptable fluid composition comprising at least one active ingredient, for example, a peptide derived from apelin, such as the amide derivative of apelin-36 (42-57). The active ingredient is usually dissolved or suspended in a physiologically acceptable carrier, and the composition can additionally comprise minor amounts of one or more non-toxic auxiliary substances, such as emulsifying agents, preservatives, and pH buffering agents and the like. Such injectable compositions that are useful for use with the compositions of this disclosure are conventional; appropriate formulations are well known in the art.

Isolated: An "isolated" biological component (such as a nucleic acid molecule, protein or portion of a tissue) that has been substantially separated or purified away from other biological components in the tissue or cell of the organism in which the component naturally occurs. An "isolated" cell is a cell that has been purified from the other cellular components of a tissue. Cells can be isolated by, for instance mechanical and/or enzymatic methods.

Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Labeled: A biomolecule, such as a peptide or a specific binding agent, attached covalently or noncovalently to a detectable label or reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, for example, in Sambrook et al., *Molecular Cloning: A Laboratory Manual,* CSHL, New York, 1989 and Ausubel et al., *Current Protocols in Molecular Biology,* Greene Publ. Assoc. and Wiley-Intersciences, 1998.

Mammal: This term includes both human and non-human mammals. Similarly, the term "subject" includes both human and veterinary subjects.

Nucleotide: "Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in an oligonucleotide/polynucleotide. A nucleotide sequence refers to the sequence of bases in an oligonucleotide/polynucleotide.

The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U). Inosine is also a base that can be integrated into DNA or RNA in a nucleotide (dITP or ITP, respectively).

Oligonucleotide: An oligonucleotide is a plurality of joined nucleotides joined by native phosphodiester bonds, between about 6 and about 500 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Particular oligonucleotides and oligonucleotide analogs can include linear sequences up to about 300 nucleotides in length, for example a sequence (such as DNA or RNA) that is at least 6 bases, for example at least 8, 10, 12, 15, 17, 20, 25, 30, 35, 40, 45, 50, 100 or even 200 or more bases long, or from about 6 to about 50 bases, for example about 8-25 bases, such as 10, 12, 15, 17, 20, or 25 bases.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Parenteral: Administered outside of the intestine, For example, not via the alimentary tract. Generally, parenteral formulations are those that will be administered through any possible mode except ingestion. This term especially refers to injections, whether administered intravenously, intrathecally, intramuscularly, intraperitoneally, or subcutaneously, and various surface applications including intranasal, intradermal, and topical application, for instance.

Peptide: "Peptides," "polypeptides," and "oligopeptides" are chains of amino acids (typically L-amino acids) whose alpha carbons are linked through peptide bonds formed by a condensation reaction between the carboxyl group of the alpha carbon of one amino acid and the amino group of the alpha carbon of another amino acid. The terminal amino acid at one end of the chain (for example, the amino terminal) has a free amino group, while the terminal amino acid at the other end of the chain (for example, the carboxy terminal) has a free carboxyl group. As such, the term "amino terminus" (abbreviated N-terminus) refers to the free alpha-amino group on the amino acid at the amino terminal end of the peptide, or to the alpha-amino group (imino group when participating in a peptide bond) of an amino acid at any other location within the peptide. The term "carboxy terminus" (abbreviated C-terminus) refers to the free carboxyl group on the amino acid at the carboxy terminal end of a peptide, or to the carboxyl group of an amino acid at any other location within the peptide.

Typically, the amino acids making up a peptide are numbered in order, starting at the amino terminus and increasing in the direction toward the carboxy terminus of the peptide. Thus, when one amino acid is said to "follow" another, that amino acid is positioned closer to the carboxy terminal end of the peptide than the preceding amino acid.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of the compounds herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

A "pharmaceutical agent" or "drug" refers to a chemical compound or other composition (including peptide based pharmaceuticals) capable of inducing a desired therapeutic or prophylactic effect when properly administered to a subject.

Polypeptide: A polymer in which the monomers are amino acid residues that are joined together through amide bonds. When the amino acids are alpha-amino acids, either the L-optical isomer or the D-optical isomer can be used, the L-isomers being preferred in nature. The term polypeptide or protein as used herein encompasses any amino acid sequence and includes, but may not be limited to, modified sequences such as glycoproteins or amidated proteins. The term polypeptide is specifically intended to cover naturally occurring proteins, as well as those that are recombinantly or synthetically produced.

Substantially purified polypeptide as used herein refers to a polypeptide that is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

A non-conservative amino acid substitution can result from changes in: (a) the structure of the amino acid backbone in the area of the substitution; (b) the charge or hydrophobicity of the amino acid; or (c) the bulk of an amino acid side chain. Substitutions generally expected to produce the greatest changes in protein properties are those in which: (a) a hydrophilic residue is substituted for (or by) a hydrophobic residue; (b) a proline is substituted for (or by) any other residue; (c) a residue having a bulky side chain, e.g., phenylalanine, is substituted for (or by) one not having a side chain, e.g., glycine; or (d) a residue having an electropositive side chain, e.g., lysyl, arginyl, or histadyl, is substituted for (or by) an electronegative residue, e.g., glutamyl or aspartyl.

Variant amino acid sequences may, for example, be 80, 90 or even 95 or 98% identical to the native amino acid sequence. Programs and algorithms for determining percentage identity can be found at the NCBI website.

Post-translational modification: The modification of a newly formed protein; may involve deletion of amino acids, chemical modification of certain amino acids (for example, amidation, acetylation, phosphorylation, glycosylation, formation of pyroglutamate, oxidation/reduction of sulfa group on a methionine, or addition of similar small molecules) to certain amino acids.

Preproprotein: A biologically inert polypeptide that is post-translationally modified to yield one or more biologically active peptides. The maturation pathway of preproproteins involves the proteolytic cleavage of an amino terminal signal peptide to yield a proprotein, which can have biological activity. Enzymatic processing of the resulting proprotein can yield one or more biologically active peptides.

Probes and primers: Nucleic acid probes and primers can be readily prepared based on the nucleic acid molecules provided as indicators of disease or disease progression. It is also appropriate to generate probes and primers based on fragments or portions of these nucleic acid molecules. Also appropriate are probes and primers specific for the reverse complement of these sequences, as well as probes and primers to 5' or 3' regions.

A probe comprises an isolated nucleic acid attached to a detectable label or other reporter molecule. Typical labels and reporter molecules include radioactive isotopes, enzyme substrates, co-factors, ligands, chemiluminescent or fluorescent agents, haptens, and enzymes. Methods for labeling and guidance in the choice of labels appropriate for various purposes are discussed, e.g., in Sambrook et al. (In *Molecular Cloning: A Laboratory Manual*, CSHL, New York, 1989) and Ausubel et al. (In *Current Protocols in Molecular Biology*, John Wiley & Sons, New York, 1998).

Primers are short nucleic acid molecules, for instance DNA oligonucleotides 8 nucleotides or more in length. Longer DNA oligonucleotides may be about 10, 12, 15, 17, 20, 25, 30 or 50 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, e.g., by the polymerase chain reaction (PCR) or other in vitro nucleic-acid amplification methods known in the art.

Methods for preparing and using nucleic acid probes and primers are described, for example, in Sambrook et al. (In *Molecular Cloning: A Laboratory Manual*, CSHL, New York, 1989), Ausubel et al. (ed.) (In *Current Protocols in Molecular Biology*, John Wiley & Sons, New York, 1998), and Innis et al. (*PCR Protocols, A Guide to Methods and Applications*, Academic Press, Inc., San Diego, Calif., 1990). Amplification primer pairs (for instance, for use with polymerase chain reaction amplification) can be derived from a known sequence such as the salcut sequences described herein, for example, by using computer programs intended for that purpose such as Primer (Version 0.5, ©1991, Whitehead Institute for Biomedical Research, Cambridge, Mass.).

One of ordinary skill in the art will appreciate that the specificity of a particular probe or primer increases with its length. Thus, for example, a primer comprising 15 consecutive nucleotides of a salcut protein-encoding nucleotide will anneal to a target sequence, such as another homolog of the designated salcut protein, with a higher specificity than a corresponding primer of only 8 or 10 nucleotides. Thus, in order to obtain greater specificity, probes and primers can be selected that comprise at least 12, 15, 17, 20, 23, 25, 27, 30 or more consecutive nucleotides of a salcut protein-encoding nucleotide sequences.

Also provided are isolated nucleic acid molecules that comprise specified lengths of the disclosed salcut nucleotide sequences. Such molecules may comprise at least 8, 10, 12, 15, 20, 23, 25 or more consecutive nucleotides of these sequences. These molecules may be obtained from any region of the disclosed sequences.

Purified: A "purified" biological component (such as a nucleic acid molecule, protein or portion of a tissue) that has been substantially separated or purified away from other biological components in the tissue or cell of the organism in which the component naturally occurs. A "purified" cell is a cell that has been purified from the other cellular components of a tissue. Cells can be purified by, for instance mechanical and/or enzymatic methods.

Nucleic acids and proteins that have been "purified" include nucleic acids and proteins purified by standard purification methods. The term also embraces nucleic acids and proteins prepared by recombinant expression in a host cell as well as chemically synthesized nucleic acids.

The term "purified" does not require absolute purity; rather, it is intended as a relative term.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques.

Salcut (Selective Apelin 36 Cutting): An apelin peptide derived from the apelin preproprotein (1-77). Salcut generally refers to any peptide derived from residues 42-57 of apelin (1-77). Salcut is more specifically derived from the amino (N)-terminal region (residues 42-57) of apelin-36 (42-77). Salcut can have a modified C-terminal glycine that has an amino ($-NH_2$) group substituted for its hydroxyl ($-OH$) group. This modified peptide is known as salcut-$NH_2$ or apelin-36 (42-57)-$NH_2$ (FIGS. 1 and 2). A salcut peptide can also be the free-acid derivative of salcut-$NH_2$ (salcut-OH; also referred to as apelin-36 (42-57)) or a glycine-extended apelin-36 (42-58) (salcut-glycine; salcut-gly).

Sample: Includes biological samples such as those derived from a human or other animal source (for example, blood, sweat, tears, breast milk, bone marrow, stool, sera, urine, saliva, tears, biopsy samples, broncho-alevolar lavage fluids, histology tissue samples, cellular smears, moles, warts, body secretions etc.); bacterial or viral preparations; cell cultures; forensic samples; agricultural products; waste or drinking water; milk or other processed foodstuff; air; and so forth. Samples containing a small number of cells can be acquired by any one of a number of methods, such as needle aspiration, biopsy, or tissue scrapes.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are. Homologs or orthologs of the disclosed apelin-36 (42-57) peptides, and the corresponding cDNA sequences, will possess a relatively high degree of sequence identity when aligned using standard methods. This homology will be more significant when the orthologous proteins or genes or cDNAs are derived from species that are more closely related (e.g., human and chimpanzee sequences), compared to species more distantly related (e.g., human and *C. elegans* sequences).

Methods of alignment of sequences for comparison are well known in the art. Various programs and alignment algorithms are described in: Smith & Waterman *Adv. Appl. Math.* 2: 482, 1981; Needleman & Wunsch *J. Mol. Biol.* 48: 443, 1970; Pearson & Lipman *Proc. Natl. Acad. Sci. USA* 85: 2444, 1988; Higgins & Sharp *Gene,* 73: 237-244, 1988; Higgins & Sharp *CABIOS* 5: 151-153, 1989; Corpet et al. *Nuc. Acids Res.* 16, 10881-90, 1988; Huang et al. *Computer Appls. in the Biosciences* 8, 155-65, 1992; and Pearson et al. *Meth. Mol. Bio.* 24, 307-31, 1994. Altschul et al. (*J. Mol. Biol.* 215:403-410, 1990), presents a detailed consideration of sequence alignment methods and homology calculations.

The NCBI Basic Local Alignment Search Tool (BLAST) (Altschul et al. *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx. When aligning short peptides (fewer than around 30 amino acids), the alignment is performed using the Blast 2 sequences function, employing the PAM30 matrix set to default parameters (open gap 9, extension gap 1 penalties).

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence remains hybridized to a perfectly matched probe or complementary strand. Conditions for nucleic acid hybridization and calculation of stringencies can be found in Sambrook et al. (In *Molecular Cloning: A Laboratory Manual*, CSHL, New York, 1989) and Tijssen (*Laboratory Techniques in Biochemistry and Molecular Biology—Hybridization with Nucleic Acid Probes* Part I, Chapter 2, Elsevier, N.Y., 1993). Nucleic acid molecules that hybridize under stringent conditions to a salcut protein-encoding sequence will typically hybridize to a probe based on either an entire salcut protein-encoding sequence or selected portions of the encoding sequence under wash conditions of 2×SSC at 50° C.

Nucleic acid sequences that do not show a high degree of sequence identity may nevertheless encode similar amino acid sequences, due to the degeneracy of the genetic code. It is understood that changes in nucleic acid sequence can be made using this degeneracy to produce multiple nucleic acid molecules that all encode substantially the same protein.

Small molecule inhibitor: An inhibitor of at least one function of a target molecule, with a molecular weight preferably below about 1000 Daltons.

Specific binding agent: An agent that binds substantially only to a defined target. Thus an apelin-36 (42-57) specific binding agent is an agent that binds substantially to apelin-36 (42-57). In one embodiment, the specific binding agent is a monoclonal antibody or a polyclonal antibody that specifically apelin-36 (42-57). In particular a embodiment, the monoclonal antibody is humanized.

Subject: Any vertebrate that has a vascular system and has hematopoietic cells in the wild-type organism. The term subject includes non-human mammals such as a monkey, mouse, rat, rabbit, pig, goat, sheep or cow. It also includes humans. It is understood that a cell or cell line in culture can be referred to as obtained from a subject even though the cell has been in culture for a length of time, even years.

Therapeutic: Therapeutic uses of apelin-36 (42-57) include administration for the inhibition, reversal or prevention of pathological conditions, such as neoplasia, hypertension, preeclampsia syndrome, diabetes, ocular degeneration, idiopathic pulmonary fibrosis, wound healing, abnormal angiogenesis, altered mast cell migration, chronic obstructive pulmonary disease, inflammatory diseases such as arthritis (juvenile and rheumatoid) and inflammatory bowel disease, cardiovascular disease, avascular or ischemic insult, myocardial infarction, stroke, vasculititis/angiitis, systemic or vascular sclerosis, gangrene, congelation (severe frostbite), alopecia, eczema, ulcers, lymphedema (parasite induced, for example elephantiasis/elephantitis, or tumor induced), vascular hyperplasia, hemangioma, diabetic induced retinopathy, macular degenerative disease, psoriasis, or endometriosis.

Therapeutically effective amount: A quantity of compound, such as the peptide salcut-$NH_2$ (apelin-36 (42-57)) or a specific inhibitor of salcut-$NH_2$, sufficient to achieve a desired effect in a subject being treated. For instance, this can be the amount necessary to treat or ameliorate any one of a number of diseases, such as neoplasia, hypertension, preeclampsia syndrome, diabetes, ocular degeneration, idiopathic pulmonary fibrosis, wound healing, abnormal angiogenesis, altered mast cell migration, chronic obstructive pulmonary disease, inflammatory diseases such as arthritis (juvenile and rheumatoid) and inflammatory bowel disease, cardiovascular disease, avascular or ischemic insult, myocardial infarction, stroke, vasculititis/angiitis, systemic or vascular sclerosis, gangrene, congelation (severe frostbite), alopecia, eczema, ulcers, lymphedema (parasite induced, for example elephantiasis/elephantitis, or tumor induced), vascular hyperplasia, hemangioma, diabetic induced retinopathy, macular degenerative disease, psoriasis, or endometriosis, in a subject. In some embodiments, it is the amount necessary to treat a subject by a measurable amount over a period of time, or to measurably inhibit progression of disease, in a subject. In other embodiments, a therapeutically effective amount is the amount necessary to prophylactically inhibit a disease.

An effective amount of salcut, for example salcut-$NH_2$, may be administered in a single dose, or in several doses, for example daily, during a course of treatment. However, the effective amount will be dependent on the compound applied, the subject being treated, the severity and type of the affliction, and the manner of administration of the compound.

Tumor: A neoplasm that may be either malignant or non-malignant. Tumors originating in a particular organ (such as breast, prostate, bladder or lung) are primary tumors. Tumors of the same tissue type may be divided into tumor of different sub-types (a classic example being bronchogenic carcinomas (lung tumors) which can be an adenocarcinoma, small cell, squamous cell, or large cell tumor).

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents and other references mentioned herein are incorporated by reference in their entirety. All sequence database references are incorporated by reference as of Feb. 27, 2009, unless specified otherwise. In case of conflict, the present specification, including explanations of terms, will control. In addition, the materials, methods, and examples are illustrative only and not intended to be limiting.

III. Overview of Several Embodiments

Disclosed herein are isolated apelin-36 (42-57) and apelin-36 (42-58) polypeptides having an amino acid sequence set forth as SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 41, SEQ ID NO: 42, or SEQ ID NO: 43. The polypeptides have cell growth modulating activity and can have up to four amino acid substitutions, which substitutions are not at the last position of the amino acid sequence. Alternatively, the polypeptides can have up to three, two, one, or no amino acid substitutions.

Also provided herein are polypeptides comprising a polypeptide comprising an amino acid sequence consisting of SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 41, SEQ ID NO: 42, or SEQ ID NO: 43, wherein the amino terminal end of the amino acid sequence is attached to a heterologous amino acid sequence, label, or reporter molecule.

Pharmaceutical compositions, comprising the disclosed polypeptide in a pharmaceutically acceptable carrier are also envisioned, as are inhibitors or activators of the cell growth modulating activity of the polypeptides. Such inhibitors and activators include peptides, small molecules, receptors, binding proteins, salcut-Gly, free-acid form of apelin-36 (42-57), or neutralizing antibodies. Also provided herein are methods of treating a tumor or a disease caused by abnormal angiogenesis in a subject. The method includes administering to a subject that has a tumor or a disease caused by abnormal angiogenesis a therapeutically effective amount of at least one of the disclosed inhibitors. Administration of an inhibitor modifies tumor cell growth or endothelial cell growth in the subject, thereby treating the tumor or disease caused by abnormal angiogenesis of the subject. The method also includes administering to a subject that has a disease caused by abnormal angiogenesis a therapeutically effective amount of the disclosed activators. Administration of an activator modifies endothelial cell growth in the subject, thereby treating the disease caused by abnormal angiogenesis of the subject.

In addition, disclosed herein are isolated antibodies that bind to an epitope that is specific to the disclosed polypeptides and does not bind to apelin-36 (42-77), apelin-17 (61-77), or apelin-13 (65-77). The antibodies can be monoclonal antibodies. In one embodiment, the monoclonal antibody is humanized. Nucleic acid sequences encoding the disclosed polypeptides are also provided herein.

A method of modulating cell growth is provided herein. The method comprises administering the disclosed polypeptides to a cell sample, thereby modulating cell growth. A modulation in cell growth can be an increase or a decrease in cell growth. The cells can be endothelial cells or tumor cells. In one embodiment, the method includes administering the disclosed polypeptides to a cell sample in vivo.

It is further disclosed a method of treating a tumor or a disease caused by abnormal angiogenesis of a subject, comprising administering to the subject a therapeutically effective amount of the disclosed polypeptides, wherein the subject has a tumor or a disease caused by abnormal angiogenesis and administration of the isolated polypeptide modifies tumor cell growth or endothelial cell growth in the subject, thereby treating the tumor or disease caused by abnormal angiogenesis of the subject.

A method of diagnosing severity of a disease is also provided herein. The method comprises measuring the level of the disclosed polypeptides in a biological sample, wherein a change in the level of the isolated polypeptide correlates with severity of disease, thereby diagnosing severity of a disease. In one embodiment of the method, measuring the level of the isolated polypeptide comprises contacting the biological sample with an antibody that is specific to the disclosed polypeptide and that does not bind to apelin-36 (42-77), apelin-17 (61-77), or apelin-13 (65-77).

Diseases treated or diagnosed, using the methods disclosed herein, include neoplasia, cardiovascular disease, peripheral vascular disease, hypertension, preeclampsia syndrome, abnormal angiogenesis, diabetes, ocular degeneration, idiopathic pulmonary fibrosis, wound healing, altered mast cell migration, chronic obstructive pulmonary disease, inflammatory diseases such as arthritis (juvenile and rheumatoid) and inflammatory bowel disease, cardiovascular disease, avascular or ischemic insult, myocardial infarction, stroke, vasculititis/angiitis, systemic or vascular sclerosis, gangrene, congelation (severe frostbite), alopecia, eczema, ulcers, lymphedema (parasite induced, for example elephantiasis/elephantitis, or tumor induced), vascular hyperplasia, hemangioma, diabetic induced retinopathy, macular degenerative disease, psoriasis, or endometriosis.

IV. Apelin and Related Peptides

Apelin cDNA has been identified in various species, including human (NM_017413; SEQ ID NO: 1), dog (ENSCAFT00000029682; SEQ ID NO: 2), bovine (NM_174503 or ENSBTAT00000026630; SEQ ID NO: 3), rat (GenBank Accession No. NM_031612; SEQ ID NO: 4), mouse (NM_013912; SEQ ID NO: 5), zebra fish (DQ062434; SEQ ID NO: 7), and rhesus monkeys (ENSMMUT00000003625; SEQ ID NO: 39). Each of these cDNAs code for a preprotein of 77 amino acids (SEQ ID NOs: 8-14 and 40, respectively; see also the following Accession Nos.: human—NP_059109 or AAF25815; dog—ENSCAFP00000027587; bovine—NP_776928 or ENSBTAP00000026630; rat—NP_113800.1; mouse—NP_038940; zebra fish—AAY46798; rhesus monkey—ENSMMUP00000003428). Frog cDNA (NM_001097924; SEQ ID NO: 36) and opossum cDNA (ENSMODT00000016827; SEQ ID NO: 6) encode for a preprotein of 76 amino acids (NP_001091393; SEQ ID NO: 37 and ENSMODP00000016523, respectively). The content of the Accession Numbers listed for human, dog, bovine, rat, mouse, opossum, frog, and zebra fish is incorporated by reference as of Feb. 27, 2009. The content of the Accession Numbers listed for rhesus monkey is incorporated by reference as of Mar. 1, 2010. The amino acid sequence of the apelin preproprotein (residues 1-77, or 1-76 for opossum) is highly conserved across species, with identity in the carboxy (C)-terminal region. Apelin-36 (see, for example, the human sequence; SEQ ID NO: 15) is a 36 amino acid peptide derived from the 77 amino acid apelin (1-77) preproprotein (Tatemoto et al., *Biochem. Biophys. Res. Comm.,* 251:471-476, 1998) and corresponds to residues 42-77 of the C-terminal region of the apelin (1-77) preproprotein (FIG. 1). Apelin-17 (for example, SEQ ID NO: 16) and apelin-13 (for example, SEQ ID NO: 17) are also derived from the C-terminal end of apelin (residues 61-77 and 65-77, respectively; FIG. 1).

Peptide-induced acidification rates of cells expressing the apelin G protein receptor (known as APJ) have been shown to increase in potency with decreased apelin peptide size, such that apelin-36 is least potent, apelin-17 is moderately potent, and apelin-13 is most potent (Tatemoto et al., *Biochem. Biophys. Res. Comm.*, 251:471-476, 1998). Apelin-13 has also been shown to have mitogenic activity and to have a specific effect on neoangiogenesis/endothelial cell growth (Kalin et al., *Dev. Biol.*, 305:599-614, 2007; Masri et al., *FASEB Journal* express article 10.1096/fj.04-1930fje. Published online Sep. 22, 2004, 26 pages; Sorli et al., *Oncogene*, 26:7692-7699, 2007). Both apelin-36 and apelin-13 bind the APJ apelin receptor and regulate the same set of intracellular effectors; however, they display different desensitization patterns on the APJ receptor, which may explain their varying physiological responses (Masri et al., *J. Biol. Chem.* 281:18317-18326, 2006).

V. Apelin-36 (42-57) Peptides and Nucleic Acids

It has been surprisingly discovered that a new biologically active peptide can be derived from apelin-36 (42-77). This sixteen amino acid peptide of human apelin-36 (42-77) (referred to herein as human salcut, human salcut-OH, or human apelin-36 (42-57); SEQ ID NO: 18), derived from the amino (N)-terminal region (residues 42-57) of human apelin-36, optionally has a modified C-terminal glycine that has an amino (—$NH_2$) group substituted for its hydroxyl (—OH) group. This C-terminal modified peptide is referred to as an amidation or amide derivative of human apelin-36 (42-57), and is also known as human salcut-$NH_2$ or apelin-36 (42-57)-$NH_2$ (SEQ ID NO: 19; FIGS. 1 and 2). The glycine-extended human apelin-36 (42-58) (salcut-glycine; salcut-gly; SEQ ID NO: 20) is also provided (FIG. 1).

An amidation or amide derivative of this peptide can also be derived from the N-terminal region (residues 42-57) (based on the numbering of the human apelin sequence) of apelin-36 from dog (SEQ ID NO: 22), bovine (SEQ ID NO: 25), rat (SEQ ID NO: 28), mouse (SEQ ID NO: 31), rhesus monkey (SEQ ID NO: 42), and opossum (SEQ ID NO: 34) apelin. In addition, a glycine-extended apelin-36 (42-58) (based on the numbering of the human apelin sequence) sequences from dog (SEQ ID NO: 23), bovine (SEQ ID NO: 26), rat (SEQ ID NO: 29), mouse (SEQ ID NO: 32), rhesus monkey (SEQ ID NO: 43), and opossum (SEQ ID NO: 35) are provided.

The salcut consensus amidation motif (G-R-R or G-R-K) is located, for example, at residues 58-60 of human, bovine, dog, rat, mouse, and rhesus monkey apelin (1-77) and at residues 57-59 of opossum apelin (1-76) (FIG. 2). In other embodiments, the salcut amidation motif is G-K-K or G-K-R. The amidation motif includes a glycine followed by no basic amino acid, or by one or more basic amino acids. Salcut and its biologically active derivatives may be isolated from nature, or synthesized in vitro using techniques well known to those of skill in the art. Representative production techniques are provided herein.

With the provision herein of the apelin-36 (42-57) amino acid and cDNA sequences, in vitro nucleic acid amplification (such as polymerase chain reaction (PCR)) may be utilized as a simple method for producing apelin-36 (42-57) nucleic acid sequences, and variants thereof. The selection of amplification primers will be made according to the portion(s) of the apelin preproprotein cDNA that is to be amplified, for example the portion of apelin (1-77) including apelin-36 (42-57). In one embodiment, primers may be chosen to amplify a segment of a cDNA that encodes the apelin-36 (42-57) polypeptide. Variations in amplification conditions may be useful to optimize amplification conditions when using primers and amplicons of differing lengths and composition; such considerations are well known in the art and are discussed for instance in Innis et al. (*PCR Protocols, A Guide to Methods and Applications*, Academic Press, Inc., San Diego, Calif., 1990).

Re-sequencing of PCR products obtained by amplification procedures optionally can be performed to facilitate confirmation of the amplified sequence and provide information about natural variation of this sequence in different populations or species. Oligonucleotides derived from the known or provided apelin sequences may be used in such sequencing methods.

In one embodiment, primers or oligonucleotides may comprise a sequence of at least 8 consecutive nucleotides of the apelin (1-77) or apelin-36 (42-57) nucleic acid sequence. If these primers or oligonucleotides are used with an in vitro amplification procedure (such as PCR), lengthening the primers or oligonucleotides may enhance amplification specificity. Thus, in other embodiments, oligonucleotides or primers comprising at least 10, 12, 15, 17, 20, 25, 30, 35, 40, 45, 50, or more consecutive nucleotides of these sequences may be used. These oligonucleotides or primers, for instance, may be obtained from any region of the disclosed sequences.

VI. Apelin-36 (42-57) Sequence Variants

With the provision of apelin-36 (42-57) protein (amidated or free-acid forms) and corresponding nucleic acid sequences herein, the creation of variants of these sequences is now enabled.

In one embodiment, variant apelin-36 (42-57) proteins include proteins that differ in amino acid sequence from the apelin-36 (42-57) sequences disclosed but that share at least 72% amino acid sequence identity with the provided apelin-36 (42-57) protein. In other embodiments, other variants will share at least 75%, at least 80%, at least 85%, at least 90%, at least 95%, at least 98%, or at least 99% amino acid sequence identity. Manipulation of the nucleotide sequence of apelin-36 (42-57) using standard procedures, including in one specific, non-limiting, embodiment, site-directed mutagenesis or in another specific, non-limiting, embodiment, PCR, can be used to produce such variants. The simplest modifications involve the substitution of one or more amino acids for amino acids having similar biochemical properties. These so-called conservative substitutions are likely to have minimal impact on the activity of the resultant protein. One would avoid substituting the residues of the salcut consensus amidation motif (for example, G-R-R or G-R-K), as well as any residues that have not diverged among mammalian species (FIG. 2).

Orthologs of apelin-36 (42-57) (amidated or free-acid forms; based on the numbering of the human sequence) can be isolated. In one embodiment, orthologs will generally share at least 65% sequence identity with the disclosed apelin-36 (42-57) cDNA. Where the orthologous species is more closely related to the subject species, the sequence identity will in general be greater. In other embodiments, closely related orthologous apelin-36 (42-57) molecules may share at least 70%, at least 75%, at least 80% at least 85%, at least 90%, at least 91%, at least 93%, at least 95%, at least 98%, or at least 99% sequence identity with the disclosed apelin-36 (42-57) nucleotide or amino acid sequences.

Additional aspects of the disclosure include analogs, derivatives, and mimetics based on the amino acid sequence of the apelin-36 (42-57) peptides (amidated or free-acid forms) disclosed herein. Typically, mimetic compounds are synthetic compounds having a three-dimensional structure (of at least part of the mimetic compound) that mimics, for example, the primary, secondary, and/or tertiary structural, and/or electrochemical characteristics of a selected peptide, structural domain, active site, or binding region (e.g., a homotypic or heterotypic binding site, a catalytic active site or domain, a receptor or ligand binding interface or domain, or a structural motif) thereof. The mimetic compound will often share a desired biological activity with a native peptide, as discussed herein (e.g., cell growth modulating activity). Typically, at least one subject biological activity of the mimetic compound is not substantially reduced in comparison to, and is often the same as or greater than, the activity of the native peptide on which the mimetic was modeled.

A variety of techniques well known to one of skill in the art are available for constructing peptide mimetics with the same, similar, increased, or reduced biological activity as the corresponding native peptide. Often these analogs, variants, derivatives and mimetics will exhibit one or more desired activities that are distinct or improved from the corresponding native peptide, for example, improved characteristics related to the modulation of cell growth.

In another embodiment, more substantial changes in apelin-36 (42-57) activity may be obtained by selecting amino acid substitutions that are less conservative than conservative substitutions. In one specific, non-limiting, embodiment, such changes include changing residues that differ more significantly in their effect on maintaining polypeptide backbone structure (e.g., sheet or helical conformation) near the substitution, charge or hydrophobicity of the molecule at the target site, or bulk of a specific side chain. The following specific, non-limiting, examples are generally expected to produce the greatest changes in protein properties: (a) a hydrophilic residue (e.g., seryl or threonyl) is substituted for (or by) a hydrophobic residue (e.g., leucyl, isoleucyl, phenylalanyl, valyl or alanyl); (b) a cysteine or proline is substituted for (or by) any other residue; (c) a residue having an electropositive side chain (e.g., lysyl, arginyl, or histadyl) is substituted for (or by) an electronegative residue (e.g., glutamyl or aspartyl); or (d) a residue having a bulky side chain (e.g., phenylalanine) is substituted for (or by) one lacking a side chain (e.g., glycine).

In other embodiments, changes in apelin-36 (42-57) activity or other protein features may be obtained by mutating, substituting or deleting regions of apelin-36 (42-57) that have a known function, regions where the function is yet to be determined, or regions that are known to be highly conserved or not conserved.

In another embodiment, a detectable moiety can be linked to the apelin-36 (42-57) peptides disclosed herein, creating a peptide-detectable moiety conjugate or fusion protein. Detectable moieties suitable for such use include any composition detectable by spectroscopic, photochemical, biochemical, immunochemical, electrical, optical or chemical means. The detectable moieties contemplated for the present disclosure can include, but are not limited to, a fluorescent moiety (e.g., fluorescein, rhodamine, Texas red, and the like), a radioactive moiety (e.g., $^{3}$H, $^{32}$P, $^{125}$I, $^{35}$S), an enzyme moiety (e.g., horseradish peroxidase, alkaline phosphatase), a colorimetric moiety (e.g., colloidal gold, biotin, colored glass or plastic, and the like). The detectable moiety can be linked to the apelin-36 (42-57) peptide at either the N- and/or C-terminus. Optionally, a linker can be included between the apelin-36 (42-57) peptide and the detectable moiety.

Means of detecting such moieties are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

Variant apelin-36 (42-57)-encoding sequences may be produced by standard DNA mutagenesis techniques. In one specific, non-limiting, embodiment, M13 primer mutagenesis is performed. Details of these techniques are provided in Sambrook et al. (In *Molecular Cloning: A Laboratory Manual*, CSHL, New York, 1989), Ch. 15. By the use of such techniques, variants may be created that differ in minor ways from the apelin-36 (42-57) sequences disclosed. In one embodiment, DNA molecules and nucleotide sequences that are derivatives of those specifically disclosed herein, and which differ from those disclosed by the deletion, addition, or substitution of nucleotides while still encoding a protein that has at least 65% sequence identity with the apelin-36 (42-57) sequences disclosed, are comprehended by this disclosure. In other embodiments, more closely related nucleic acid molecules that share at least 70%, at least 75%, at least 80%, at least 85%, at least 90%, at least 95%, at least 98%, or at least 99% nucleotide sequence identity with the disclosed apelin-36 (42-57) sequences are comprehended by this disclosure. Alternatively, specific examples of related nucleic acid molecules will have no more than 2, 3, 5, 7, 10, 12, 15, 20, 25, or 30 nucleic acid changes compared to the sequences disclosed herein. In one embodiment, such variants differ from the disclosed sequences by alteration of the coding region to fit the codon usage bias of the particular organism into which the molecule is to be introduced.

In other embodiments, the coding region may be altered by taking advantage of the degeneracy of the genetic code to alter the coding sequence such that, while the nucleotide sequence is substantially altered, it nevertheless encodes a protein having an amino acid sequence substantially similar to the disclosed apelin-36 (42-57) protein sequences. For example, because of the degeneracy of the genetic code, four nucleotide codon triplets—(CCU, CCC, CCA, and CCG)—code for proline. The coding sequence of any specific proline residue within the apelin-36 (42-57) protein, therefore, could be changed to any of these alternative codons without affecting the amino acid composition or characteristics of the encoded protein. Based upon the degeneracy of the genetic code, variant DNA molecules may be derived from the cDNA and gene sequences disclosed herein using standard DNA mutagenesis techniques as described above, or by synthesis of DNA sequences. Thus, this disclosure also encompasses nucleic acid sequences that encode an apelin-36 (42-57) protein, but which vary from the disclosed nucleic acid sequences by virtue of the degeneracy of the genetic code.

Nucleic acid molecules that are derived from the apelin-36 (42-57) cDNA nucleic acid sequences include molecules that hybridize under low stringency, high stringency, or very high stringency conditions to the disclosed apelin-36 (42-57) nucleic acid molecules, and fragments thereof.

Apelin-36 (42-57) nucleic acid encoding molecules, and orthologs and homologs of these sequences, may be incorporated into transformation or expression vectors.

VII. Synthesis, Purification, and Post-Translational Modification of Peptides

With the provision of apelin (1-77) (such as the cDNAs shown in SEQ ID NOs: 1-7 and 36) and apelin-36 nucleic acid sequences (FIG. 1), the synthesis and purification of apelin-36 (42-57) (salcut) peptides by standard laboratory techniques is now enabled. The apelin-36 (42-57) (salcut and salcut-NH$_2$) and apelin-36 (42-58) (salcut-Gly) peptides of the disclosure can be prepared using virtually any technique known to one of ordinary skill in the art for the preparation of peptides. For example, the peptides can be prepared using step-wise solution or solid phase peptide syntheses, or recombinant DNA techniques, or the equivalents thereof. Purified apelin-36 (42-57) protein, as well as its amidated and free-acid derivatives, may be used for functional analyses, antibody production, diagnostics, and patient therapy. Purified apelin-36 (42-58) may be used as an antagonist of the amidated form of apelin-36 (42-57). In another embodiment, the free-acid form of apelin-36 (42-57) can be used as an antagonist of the amidated form of apelin-36 (42-57).

A. Chemical Synthesis

Apelin-36 (42-57) and apelin-36 (42-58) peptides, and modified versions of these peptides (for example, amidated forms of the peptides) can be readily synthesized by automated solid phase procedures well known in the art. Techniques and procedures for solid phase synthesis are described in *Solid Phase Peptide Synthesis: A Practical Approach*, by E. Atherton and R. C. Sheppard, published by IRL, Oxford University Press, 1989. Alternatively, apelin-36 (42-57) peptides may be prepared by way of segment condensation, as described, for example, in Liu et al., *Tetrahedron Lett.* 37:933-936, 1996; Baca et al., *J. Am. Chem. Soc.* 117:1881-1887, 1995; Tam et al., *Int. J. Peptide Protein Res.* 45:209-216, 1995; Schnolzer and Kent, *Science* 256:221-225, 1992; Liu and Tam, *J. Am. Chem. Soc.* 116:4149-4153, 1994; Liu and Tam, *Proc. Natl. Acad. Sci. USA* 91:6584-6588, 1994; and Yamashiro and Li, *Int. J. Peptide Protein Res.* 31:322-334, 1988). Other methods useful for synthesizing the apelin-36 (42-57) peptides of the disclosure are described in Nakagawa et al., *J. Am. Chem. Soc.* 107:7087-7092, 1985.

Additional exemplary techniques known to those of ordinary skill in the art of peptide synthesis are taught by Bodanszky, M. and Bodanszky, A., *The Practice of Peptide Synthesis*, Springer Verlag, New York, 1994; and by Jones, J., *Amino Acid and Peptide Synthesis,* 2nd ed., Oxford University Press, 2002. The Bodanszky and Jones references detail the parameters and techniques for activating and coupling amino acids and amino acid derivatives. Moreover, the references teach how to select, use and remove various useful functional and protecting groups.

Peptides of the disclosure can also be readily purchased from commercial suppliers of synthetic peptides. Such suppliers include, for example, *Advanced ChemTech* (Louisville, Ky.), Applied Biosystems (Foster City, Calif.), Anaspec (San Jose, Calif.), and Cell Essentials (Boston, Mass.).

B. Recombinant Synthesis

The disclosed apelin-36 (42-57) (amidated or free-acid forms) and apelin-36 (42-58) peptides can also be synthesized using conventional recombinant genetic engineering techniques. For recombinant production, a polynucleotide sequence encoding the apelin-36 (42-57) or apelin-36 (42-58) peptide is inserted into an appropriate expression vehicle, that is, a vector which contains the necessary elements for the transcription and translation of the inserted coding sequence, or in the case of an RNA viral vector, the necessary elements for replication and translation. The expression vehicle is then transfected into a suitable target cell which will express the apelin-36 (42-57) or apelin-36 (42-58) peptide. Depending on the expression system used, the expressed peptide is then isolated by procedures well-established in the art. Methods for recombinant protein and peptide production are well known in the art (see, e.g., Sambrook et al. (ed.), *Molecular Cloning: A Laboratory Manual*, 2$^{nd}$ ed., vol. 1-3, Cold Spring Harbor Laboratory Press, Cold Spring Harbor, N.Y., 1989, Ch. 17 and Ausubel et al. *Short Protocols in Molecular Biology*, 4$^{th}$ ed., John Wiley & Sons, Inc., 1999).

DNA sequences can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with nucleic acid amplification. These techniques are known to those of ordinary skill.

Methods for expressing large amounts of protein from a cloned gene or cDNA sequence introduced into *Escherichia coli* (*E. coli*) may be utilized for the purification of proteins. By way of example, fusion proteins consisting of amino terminal peptides encoded by a portion of the *E. coli* lacZ or trpE gene linked to apelin-36 (42-57) proteins may be used to prepare polyclonal and monoclonal antibodies (including humanized monoclonal antibodies) against these proteins. Thereafter, these antibodies may be used in other embodiments to purify proteins by immunoaffinity chromatography, in diagnostic assays to quantitate the levels of protein and to localize proteins in tissues and individual cells by immunofluorescence. Such antibodies may be specific for epitope tags, which can be added to the expression construct for instance for identification and/or purification purposes.

To increase efficiency of production, the polynucleotide can be designed to encode multiple units of the apelin-36 (42-57) or apelin-36 (42-58) peptide separated by enzymatic cleavage sites. The resulting polypeptide can be cleaved (e.g., by treatment with the appropriate enzyme) in order to recover the peptide units. This can increase the yield of peptides driven by a single promoter. In one embodiment, a polycistronic polynucleotide can be designed so that a single mRNA is transcribed which encodes multiple peptides, each coding region operatively linked to a cap-independent translation control sequence, for example, an internal ribosome entry site (IRES). When used in appropriate viral expression systems, the translation of each peptide encoded by the mRNA is directed internally in the transcript, for example, by the IRES. Thus, the polycistronic construct directs the transcription of a single, large polycistronic mRNA which, in turn, directs the translation of multiple, individual peptides. This approach eliminates the production and enzymatic processing of polyproteins and can significantly increase yield of peptide driven by a single promoter.

A variety of host-expression vector systems may be utilized to express the peptides described herein. These include, but are not limited to, microorganisms such as bacteria transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus (CaMV) or tobacco mosaic virus (TMV)) or transformed with recombinant plasmid expression vectors (e.g., Ti plasmid) containing an appropriate coding sequence; or animal cell systems.

The transfer of DNA into eukaryotic, in particular human or other mammalian cells, is now a conventional technique. Recombinant expression vectors can be introduced into the recipient cells as pure DNA (transfection) by, for example, precipitation with calcium phosphate (Graham and vander Eb, *Virology* 52:466, 1973) or strontium phosphate (Brash et al., *Mol. Cell Biol.* 7:2013, 1987), electroporation (Neumann et al., *EMBO J* 1:841, 1982), lipofection (Feigner et al., *Proc. Natl. Acad. Sci USA* 84:7413, 1987), DEAE dextran (Mc-Cuthan et al., *J. Natl. Cancer Inst.* 41:351, 1968), microinjection (Mueller et al., *Cell* 15:579, 1978), protoplast fusion (Schafner, *Proc. Natl. Acad. Sci. USA* 77:2163-2167, 1980), or pellet guns (Klein et al., *Nature* 327:70, 1987). In another embodiment, the cDNA, or fragments thereof, can be introduced by infection with virus vectors. Systems are developed that use, for example, retroviruses (Bernstein et al., *Gen. Engr'g* 7:235, 1985), adenoviruses (Ahmad et al., *J. Virol.* 57:267, 1986), or Herpes virus (Spaete et al., *Cell* 30:295, 1982). Techniques of use in packaging long transcripts can be found in Kochanek et al. (*Proc. Natl. Acad. Sci. USA* 93:5731-5739, 1996), Parks et al. (*Proc. Natl. Acad. Sci. USA* 93:13565-13570, 1996) and Parks and Graham (*J. Virol.* 71:3293-3298, 1997). In yet another embodiment, apelin-36 (42-57) encoding sequences can be delivered to target cells in vitro via non-infectious systems, for instance liposomes.

Methods and plasmid vectors for producing fusion proteins or native proteins in bacteria are described in Sambrook et al. (Sambrook et al., In *Molecular Cloning: A Laboratory Manual*, Ch. 17, CSHL, New York, 1989). Such proteins may be made in large amounts, are easy to purify, and can be used to elicit antibody response. In one embodiment, apelin-36 (42-57) proteins can be produced in bacteria by placing a strong, regulated promoter and an efficient ribosome binding site upstream of the cloned gene. If low levels of protein are produced, additional steps may be taken to increase protein production; if high levels of protein are produced, purification is relatively easy. Suitable methods are presented in Sambrook et al. (In *Molecular Cloning: A Laboratory Manual*, CSHL, New York, 1989) and are well known in the art. In one embodiment, proteins expressed at high levels are found in insoluble inclusion bodies. Methods for extracting proteins from these aggregates are described by Sambrook et al. (In *Molecular Cloning: A Laboratory Manual*, Ch. 17, CSHL, New York, 1989).

It is appreciated that, for mutant or variant apelin-36 (42-57) and apelin-36 (42-58) sequences, similar systems are employed to express and produce the mutant/variant product. It is also appreciated that the recombinant apelin-36 (42-57) sequence can be further modified (for example, by amidation).

C. Purification

The apelin-36 (42-57) (amidated or free-acid forms) and apelin-36 (42-58) peptides can be purified by many techniques well known in the art, such as reverse phase chromatography, high performance liquid chromatography, ion exchange chromatography, size exclusion chromatography, affinity chromatography, gel electrophoresis, and the like. The actual conditions used to purify a particular apelin-36 (42-57) or apelin-36 (42-58) peptide, or their modified forms, will depend, in part, on synthesis strategy and on factors such as net charge, hydrophobicity, hydrophilicity, and the like, and will be apparent to those of ordinary skill in the art.

D. Post-Translational Modifications

Proteins can be altered by a chemical modification after translation by any means known in the art. Examples of post-translational modifications include addition of functional groups (such as amide, acetate, phosphate, lipids, or carbohydrates), removal of a portion of a protein (such as a signal sequence or the initial methionine residue) or formation of alternatively spliced variants, and formation of a disulfide bond. The modifications can be disease specific and differences in the extent of the modification can be diagnostic.

Proteins or protein fragments can be isolated and/or enriched based on a post-translational modification, for example using antibodies specific for the post-translational modification. In particular embodiments, apelin-36 (42-57) peptides (amidated or free-acid forms) can be isolated based on the presence or absence of the amidated glycine in salcut-$NH_2$ by using an antibody that specifically binds the amidated glycine. Such antibodies can be used to distinguish salcut-$NH_2$ (the amidated apelin-36 (42-57) protein) from the unmodified apelin-36 (42-57), the glycine-extended apelin-36 (42-58) form, or the larger apelin-36 (42-77) proteins. In other embodiments, cells that express a receptor that binds an apelin-36 (42-57) peptide can be isolated and/or enriched when an antibody specific for a post-translational modification (such as the amidated glycine of salcut-$NH_2$, the free-acid group of salcut, or the extended glycine of salcut-gly) binds the apelin-36 (42-57) peptide bound to its cell-surface receptor.

VIII. Apelin-36 (42-57) (Salcut) and Derivatives Thereof as Modulators of Cell Growth It has been surprisingly demonstrated that apelin-36 (42-57) (salcut) has biological activity and can modulate the growth (or proliferation) of cells. In particular embodiments, post-translationally modified forms of salcut (for example, salcut-$NH_2$) have a modified proliferative activity, compared to an unmodified salcut. Modulation of cell growth (or a modified proliferative activity) includes enhancing, stimulating, increasing, augmenting cell growth, or inhibiting, decreasing, reducing cell growth.

The cell growth enhancing or inhibiting activity of salcut occurs in a dose-dependent fashion. In some embodiments, the dose response is a biphasic (bell-shaped rise and fall) proliferative response. Without being bound by theory, a biphasic response is indicative of two different receptors involved in modulating the proliferative response: (i) a high affinity receptor involved in cell growth stimulation/proliferation at lower concentrations of salcut and (ii) a low affinity receptor involved in cell growth inhibition or suppression at higher concentrations of salcut. In other embodiments, the dose response increases (a proliferative response) or decreases (a cell growth suppressive response) with increasing concentrations of salcut, rather than exhibiting a biphasic effect. Salcut-$NH_2$-mediated endothelial cell proliferation is not suppressed in the presence of the APJ receptor antagonist apelin-13(F13A). Thus, salcut-$NH_2$ mediates its effects through a different receptor or receptor complex than APJ.

Recent findings have demonstrated that crypto expression is up-regulated by hypoxia and that apelin/APJ functions downstream of cripto during cardiomyocyte differentiation from embryonic cells (Bianco et al., *Am. J. Path*, 175:2146-2158, 2009; D'Aniello et al., *Circ. Res.*, 105:231-238, 2009) and may function with cripto in regulating tumor neovascularization. Thus, in addition to playing a role in breast carcinogenesis, salcut-$NH_2$ could play a modulatory role in nodal/cripto regulation of embryogenesis and melanoma progression (Strizzi et al., *Breast Dis.*, 29:91-103, 2008) and cripto control of cardiomyocyte differentiation (D'Aniello et al., *Circ. Res.*, 105:231-238, 2009).

An increase or decrease in cell growth or proliferation can be quantified using any method known to those of skill in the art. An increase or decrease in cell growth can be expressed as a statistically significant change in the number or percentage of cells in a cell population in the presence of salcut (for example, salcut-$NH_2$ or salcut-OH), compared to the same cell population in the absence of salcut. In specific, non-limiting examples, an increase in cell growth or proliferation can be a 10%, 20%, 30%, 50%, 70%, 80%, 90%, 100%, 200%, or more increase in cell growth or proliferation. In other specific, non-limiting examples, a decrease in cell growth or proliferation can be a 10%, 20%, 30%, 50%, 70%, 80%, 90%, or 100% decrease in cell growth or proliferation.

Salcut and its modified forms modulate the growth of cells derived from any species, for example human, bovine, dog, rat, mouse, rhesus monkey, or opossum cells. In addition, salcut-$NH_2$ and salcut-OH modulate cell growth either in vitro or in vivo.

A. Apelin-36 (42-57) (Salcut) and Derivatives Thereof as Mitogens

The current disclosure demonstrates that apelin-36 (42-57) (salcut) is a mitogen and can modulate cell growth. The amidated form of apelin-36 (42-57) (salcut-$NH_2$) is a potent mitogen and is capable of stimulating or enhancing the growth of cells, compared to unmodified apelin-36 (42-57), or other derivatives of apelin-36 (42-77). In one embodiment, salcut-$NH_2$ stimulates or enhances the growth of endothelial cells. Specific, non-limiting examples of endothelial cells include endothelial cells of the blood or lymphatic systems. In other embodiments, salcut-$NH_2$ stimulates or enhances the growth of inflammatory cells (for example, mast cells, granulocytes, lymphocytes, macrophages) or tumor cells (for example, breast cancer or gastric cancer cells). In particular embodiments, the free-acid derived form of salcut (salcut-OH) is a less potent mitogen than salcut-$NH_2$.

The cell growth enhancing or stimulating activity of salcut occurs in a dose-dependent fashion. In one embodiment, salcut-$NH_2$ is growth enhancing in the 10 pM-100 nM concentration range. In other embodiments, salcut-$NH_2$ has growth enhancing activity in the 100 pM-100 nM, 100 pM-10 nM, 10 pM-10 nM, 10 pM-1.0 nM, the 100 pM-1.0 nM, or the 1.0 nM-10 nM concentration range. The glycine-extended form of apelin-36 (42-57) (salcut-Gly) is substantially devoid of cell growth modulating activity.

B. Apelin-36 (42-57) (Salcut) and Derivatives Thereof as Suppressors of Proliferation It has also been surprisingly demonstrated that apelin-36 (42-57) (salcut) also has growth suppression activity. In particular embodiments, the amidated form of apelin-36 (42-57) (salcut-$NH_2$) has cell growth inhibitory activity at higher concentrations (for example, at 100 nM or higher concentration of salcut-$NH_2$) in addition to mitogenic activity at lower concentrations (for example, at 100 nM or lower concentration of salcut-$NH_2$). In one specific embodiment, salcut-$NH_2$ demonstrates a growth inhibitory effect of endothelial cells (for example, cells of the blood or lymphatic systems). In other embodiments, salcut-$NH_2$ inhibits the growth of inflammatory cells (for example, mast cells) or tumor cells (for example, lung cancer cells).

The cell growth inhibiting activity of salcut-$NH_2$ occurs in a dose-dependent fashion. In another embodiment, salcut-$NH_2$ has growth inhibiting activity in the 10 nM-10 µM concentration range. In other embodiments, salcut-$NH_2$ is growth inhibiting in the 500 nM-1.0 µM, 1.0 µM-10 µM, 100 nM-10 µM, 100 nM-1 µM concentration range, or at concentrations of salcut-$NH_2$ greater than 10 µM.

VIII. Production of an Antibody to Apelin-36 (42-57), and Apelin-36 (42-57) Variants and Derivatives Monoclonal or polyclonal antibodies may be produced to either the normal apelin-36 (42-57) protein or variant or mutant forms of this protein. In one embodiment, antibodies raised against the apelin-36 (42-57) protein would specifically detect the apelin-36 (42-57) protein. That is, such antibodies would recognize and bind the apelin-36 (42-57) protein, or fragments thereof, and would not substantially recognize or bind to other apelin proteins found in cells from the same species. In particular embodiments, such antibodies would recognize an epitope including the amidated glycine of apelin-36 (42-57) and could thereby distinguish the amidated apelin-36 (42-57) protein from the unmodified apelin-36 (42-57), the glycine-extended apelin-36 (42-58) form, or the larger apelin-36 (42-77) proteins from the same species. In some embodiments, antibodies against the human apelin-36 (42-57) protein may recognize apelin-36 (42-57) from other species (e.g., dog apelin-36 (42-57)), and vice versa.

Monoclonal antibodies directed against apelin-36 (42-57) can modify (either enhance or suppress) the activity of apelin-36 (42-57) when bound to the peptide. For example, such a monoclonal antibody can inhibit (or neutralize) the activity of apelin-36 (42-57) by blocking an epitope on apelin-36 (42-57) that is required for receptor binding (inhibitory or neutralizing antibody). In other embodiments, a monoclonal antibody can inhibit (or neutralize) the activity of apelin-36 (42-57) by blocking an epitope on the apelin-36 (42-57) receptor. Alternatively, monoclonal antibodies can be activating, for example a monoclonal antibody directed against apelin-36 (42-57) can block a proteolytic site on apelin-36 (42-57) and augment the half-life of the peptide, without affecting receptor binding, thereby enhancing the activity of apelin-36 (42-57).

Monoclonal or polyclonal antibodies to the protein can be prepared as follows:

A. Monoclonal Antibody Production by Hybridoma Fusion

Monoclonal antibody to epitopes of the apelin-36 (42-57) protein identified and isolated as described can be prepared from murine hybridomas according to the classical method of Kohler and Milstein (*Nature* 256:495-497, 1975) or derivative methods thereof. In one specific, non-limiting embodiment, a mouse is repetitively inoculated with a few micrograms of the selected protein over a period of a few weeks. The mouse is then sacrificed, and the antibody-producing cells of the spleen isolated. The spleen cells are fused with mouse myeloma cells using polyethylene glycol, and the excess, non-fused, cells destroyed by growth of the system on selective media comprising aminopterin (HAT media). Successfully fused cells are diluted and aliquots of the dilution placed in wells of a microtiter plate, where growth of the culture is continued. Antibody-producing clones are identified by detection of antibody in the supernatant fluid of the wells by immunoassay procedures, such as ELISA, as originally described by Engvall (*Enzymol.* 70(A):419-439, 1980), and derivative methods thereof. Selected positive clones can be expanded and their monoclonal antibody product harvested for use. Detailed procedures for monoclonal antibody production are described in Harlow and Lane (*Antibodies, A Laboratory Manual*, CSHL, New York, 1988). A monoclonal antibody is further intended to include humanized monoclonal molecules that specifically bind the target antigen. Methods of humanizing monoclonal antibodies are well known in the art.

B. Polyclonal Antibody Production by Immunization

Polyclonal antiserum containing antibodies to heterogeneous epitopes of a single protein can be prepared by immunizing suitable animals with the expressed protein (for instance, expressed using a method described herein), which, in one specific, non-limiting embodiment, can be modified to enhance immunogenicity. Effective polyclonal antibody production is affected by many factors related both to the antigen and the host species. In one embodiment, small molecules may tend to be less immunogenic than others and may require the use of carriers and adjuvant, examples of which are known. In another embodiment, host animals may vary in response to site of inoculations and dose, with either inadequate or excessive doses of antigen resulting in low titer antisera. In one specific, non-limiting embodiment, a series of small doses (ng level) of antigen administered at multiple intradermal sites may be most reliable. An effective immunization protocol for rabbits can be found in Vaitukaitis et al. (*J. Clin. Endocrinol. Metab.* 33:988-991, 1971).

In one embodiment, booster injections will be given at regular intervals, and antiserum harvested when antibody titer thereof begins to fall, as determined semi-quantitatively (for example, by double immunodiffusion in agar against known concentrations of the antigen). See, for example, Ouchterlony et al. (In *Handbook of Experimental Immunology*, Wier, D. (ed.) chapter 19. Blackwell, 1973). In one specific, non-limiting embodiment the plateau concentration of antibody is usually in the range of about 0.1 to 0.2 mg/ml of serum (about 12 µM). Affinity of the antisera for the antigen is determined by preparing competitive binding curves, as described, for example, by Fisher (*Manual of Clinical Immunology*, Ch. 42, 1980).

C. Antibodies Raised Against Synthetic Peptides

A third approach to raising antibodies against the apelin-36 (42-57) protein is to use synthetic peptides synthesized on a commercially available peptide synthesizer based upon the sequence of the apelin-36 (42-57) protein. Polyclonal antibodies can be generated by injecting such peptides into, for instance, rabbits (Example 3, for instance).

D. Antibodies Raised by Injection of Apelin-36 (42-57) Encoding Sequence

In one embodiment, antibodies may be raised against the apelin-36 (42-57) protein by subcutaneous injection of a recombinant DNA vector that expresses the apelin-36 (42-57) protein into laboratory animals, such as mice. In one specific, non-limiting embodiment, delivery of the recombinant vector into the animals may be achieved using a hand-held form of the Biolistic system (Sanford et al., *Particulate Sci. Technol.* 5:27-37, 1987), as described by Tang et al. (*Nature* 356:152-154, 1992). In other embodiments, expression vectors suitable for this purpose may include those that express the apelin-36 (42-57) encoding sequence under the transcriptional control of either the human β-actin promoter or the cytomegalovirus (CMV) promoter.

Antibody preparations prepared according to these protocols are useful in quantitative immunoassays which determine concentrations of antigen-bearing substances in biological samples; they are also used semi-quantitatively or qualitatively to identify the presence of antigen in a biological sample.

IX. Qualitative and Quantitative Detection of Apelin-36 (42-57) Peptide

Antibodies can be used to assess the presence or absence of apelin-36 (42-57) (amidated or free-acid forms) in cultured cells, primary cells, or biological samples. The determination that an antibody specifically detects the apelin-36 (42-57) is made by any one of a number of standard immunoassay methods; for instance, the Western blotting technique (Sambrook et al., In *Molecular Cloning: A Laboratory Manual*, CSHL, New York, 1989). In one embodiment, it is determined whether a given antibody preparation (such as one produced in a mouse) specifically detects the apelin-36 (42-57) peptide by Western blotting. In one specific, non-limiting embodiment total cellular protein is extracted from normal human cells (for example, endothelial cells or lymphocytes) and electrophoresed on a sodium dodecyl sulfate-polyacrylamide gel. In another embodiment, the cellular protein is extracted from a tumor. The proteins are then transferred to a membrane (for example, nitrocellulose or PVDF) by Western blotting, and the antibody preparation is incubated with the membrane. After washing the membrane to remove non-specifically bound antibodies, the presence of specifically bound antibodies is detected by the use of (by way of example) an anti-mouse antibody conjugated to an enzyme such as alkaline phosphatase. Application of an alkaline phosphatase substrate 5-bromo-4-chloro-3-indolyl phosphate/nitro blue tetrazolium results in the production of a dense blue compound by immunolocalized alkaline phosphatase. Antibodies that specifically detect the apelin-36 (42-57) peptide will, by this technique, be shown to bind to the apelin-36 (42-57) protein band (which will be localized at a given position on the gel determined by its molecular weight). Alternatively, this peptide can be recognized on a Western blot using an antibody that recognizes apelin or a peptide overlapping salcut and noting the different position/molecular weight of salcut. In particular embodiments, such antibodies would recognize an epitope including the amidated glycine of apelin-36 (42-57) and could thereby distinguish the amidated apelin-36 (42-57) protein from other apelin proteins.

Non-specific binding of the antibody to other proteins may occur and may be detectable as a weak signal on the Western blot. The non-specific nature of this binding will be recognized by one skilled in the art by the weak signal obtained on the Western blot relative to the strong primary signal arising from the specific antibody-apelin-36 (42-57) protein binding.

In other embodiments, antibodies against the apelin-36 (42-57) peptide (amidated or free-acid forms) are used to localize apelin-36 (42-57) to specific cell types or to specific subcellular locations in immunohistochemical or immunofluorescence assays. In one embodiment, the cells are selected from a variety of cell lines. In other embodiments, primary cells are isolated from a tumor in a subject and are maintained in culture or the tumor is biopsied and sectioned, and the sections are prepared directly for immunohistochemistry or immunofluorescence. In one specific, non-limiting embodiment, the cells are fixed, incubated in a blocking medium, incubated with the antibody directed against apelin-36 (42-57) followed by a second incubation with a secondary antibody that is conjugated to a fluorescent probe or a colorimetric agent. Cells that express an apelin-36 (42-57) peptide that is recognized by the antibody exhibit a color or are fluorescent when viewed under a light or fluorescence microscope, respectively. Hence, uses of antibodies directed against apelin-36 (42-57) include diagnostic tests (for example, to assess apelin-36 (42-57) levels in tissue extracts and body fluids).

An alternative method of diagnosing apelin-36 (42-57) deletion, reduction, amplification, or mutation is to quantitate the level of the apelin-36 (42-57) peptide (including the amidated or free-acid forms) in the cells of a subject. In one embodiment, this diagnostic tool would be useful for detecting reduced levels of the apelin-36 (42-57) peptide that result from, for example, mutations in the promoter regions of the apelin gene or mutations within the coding region of the apelin gene that produce truncated, non-functional or unstable apelin peptides, as well as from deletions of the entire apelin gene. In another embodiment, duplications (or more copies) of the apelin gene may be detected as an increase in the expression level of apelin-36 (42-57) peptide. The determination of reduced or increased apelin-36 (42-57)

peptide levels would be an alternative or supplemental approach to the direct determination of apelin gene deletion, duplication or mutation status.

The availability of antibodies specific to the apelin-36 (42-57) peptide (amidated or free-acid forms) will facilitate the quantitation of cellular apelin-36 (42-57) peptide by one of a number of immunoassay methods (for example, an ELISA or Enzyme-Linked ImmunoSorbent Assay), which are well known in the art and are presented herein and in, for instance, Harlow and Lane (*Antibodies, A Laboratory Manual*, CSHL, New York, 1988). Many techniques are commonly known in the art for the detection and quantification of antigen (for example, the apelin-36 (42-57) peptide). In one specific, non-limiting embodiment, the purified antigen will be bound to a substrate (for example, a multiwell plate), the antibody of the sample will bind via its Fab portion to this antigen, the substrate will then be washed and a second, labeled antibody will then be added which will bind to the Fc portion of the antibody that is the subject of the assay. The second, labeled antibody will be species specific, i.e., if the serum is from a rabbit, the second, labeled antibody will be anti-rabbit-IgG antibody. The specimen will then be washed and the amount of the second, labeled antibody that has been bound will be detected and quantified by standard methods.

Examples of methods for the detection of antibodies in biological samples, including methods employing dip strips or other immobilized assay devices, are disclosed for instance in the following patents: U.S. Pat. No. 5,965,356 (Herpes simplex virus type specific seroassay); U.S. Pat. No. 6,114,179 (Method and test kit for detection of antigens and/or antibodies); U.S. Pat. No. 6,077,681 (Diagnosis of motor neuropathy by detection of antibodies); U.S. Pat. No. 6,057,097 (Marker for pathologies comprising an auto-immune reaction and/or for inflammatory diseases); and U.S. Pat. No. 5,552,285 (Immunoassay methods, compositions and kits for antibodies to oxidized DNA bases).

In one embodiment, for the purposes of quantitating the apelin-36 (42-57) peptide (amidated or free-acid forms), a biological sample of the subject, which sample includes cellular proteins, is used. Such a biological sample may be obtained from body cells, such as those present in peripheral blood, urine, saliva, tissue biopsy, broncho-alveolar lavage fluids, amniocentesis samples, surgical specimens and autopsy material. Biological samples can be obtained from normal, healthy subjects or from subjects who are predisposed to or who are already suffering from any one of a variety of tumors, such as, but not limited to, tumors of the breast, lung, colon, pancreas, liver, brain, blood, skin, prostate, testis, ovary, and stomach, or any disorder caused by abnormal angiogenesis. In one embodiment, quantitation of the apelin-36 (42-57) peptide is achieved by immunoassay and compared to levels of the protein found in healthy cells (e.g., cells from a subject known not to suffer from a tumor). In one embodiment, a significant (e.g., 10% or greater, for instance, 20%, 25%, 30%, 50%, 75%, 90%, 95%, or more) reduction in the amount of apelin-36 (42-57) peptide in the cells of a subject compared to the amount of apelin-36 (42-57) peptide found in normal cells from a subject of the same species would be taken as an indication that the subject may have deletions or mutations in the apelin gene locus. In some embodiments, a 100% reduction in the amount of apelin-36 (42-57) would be taken as an indication that the subject may have deletions or mutations in the apelin gene locus. In another embodiment, a significant (e.g., 10% or greater, for instance, 20%, 25%, 30%, 50%, 75%, 90%, 95%, 100%, or more) increase would indicate that a duplication or enhancing mutation had occurred.

X. Pharmaceutical Compositions and Uses Thereof

The apelin-36 (42-57) peptides (amidated or free-acid forms) of the disclosure can be used to treat any disorder in a subject, especially mammals (e.g., humans), for which modulating cell growth is beneficial. Such conditions include, but are not limited to neoplasia, cardiovascular disease, peripheral vascular disease, hypertension, preeclampsia syndrome, abnormal angiogenesis, diabetes, ocular degeneration, idiopathic pulmonary fibrosis, wound healing, altered mast cell migration, chronic obstructive pulmonary disease, inflammatory diseases such as arthritis (juvenile and rheumatoid) and inflammatory bowel disease, avascular or ischemic insult, myocardial infarction, stroke, vasculititis/angiitis, systemic or vascular sclerosis, gangrene, congelation (severe frostbite), alopecia, eczema, ulcers, lymphedema (parasite induced, for example elephantiasis/elephantitis, or tumor induced), vascular hyperplasia, hemangioma, diabetic induced retinopathy, macular degenerative disease, psoriasis, endometriosis, and the like.

Abnormal angiogenesis plays an active role in numerous diseases and conditions. Thus, apelin-36 (42-57) peptides can be used to stimulate angiogenesis in subjects experiencing the following vessel suppressive disorders: avascular or ischemic insult, cardiovascular disease, myocardial infarction, stroke, vasculititis/angiitis, systemic or vascular sclerosis, gangrene, congelation (severe frostbite), alopecia, eczema, ulcers, lymphedema (parasite induced, for example elephantiasis/elephantitis, or tumor induced). Apelin-36 (42-57) peptides also can be used to inhibit angiogenesis in subjects experiencing the following vessel stimulatory disorders: neoplasia, vascular hyperplasia, hemangioma, diabetic induced retinopathy, macular degenerative disease, psoriasis, endometriosis, arthritis (juvenile and rheumatoid), and the like.

In particular embodiments, the peptides of the disclosure can be used to modulate angiogenesis or inhibit tumorigenesis. In one specific non-limiting example, the apelin-36 (42-57) peptides (amidated or free-acid forms) can be used to inhibit endothelial cell growth and reduce or inhibit angiogenesis. A reduction or inhibition of angiogenesis can result in a reduction in size or eradication of a tumor. In another specific, non-limiting example, the apelin-36 (42-57) peptides can be used to inhibit tumor cell growth.

The peptides described herein can be used alone or in combination therapy with other cell growth modulating compositions or drugs used to treat the foregoing conditions. Such combination therapies include, but are not limited to simultaneous or sequential administration of the drugs involved. For example, in the treatment of tumorigenesis, the formulations comprising apelin-36 (42-57) peptides can be administered with any one or more of the tumor cell-growth inhibiting agents currently in use, for example, cisplatin, HERCEPTIN®, or tamoxifen.

In other embodiments, the apelin-36 (42-57) peptide formulations can be administered with other cell growth modulating compositions or drugs to prevent, reduce or inhibit cardiovascular disease, peripheral vascular disease, hypertension, preeclampsia syndrome, abnormal angiogenesis, diabetes, ocular degeneration, idiopathic pulmonary fibrosis, wound healing, altered mast cell migration, chronic obstructive pulmonary disease, or inflammatory diseases such as arthritis (juvenile and rheumatoid) and inflammatory bowel disease, avascular or ischemic insult, myocardial infarction, stroke, vasculititis/angiitis, systemic or vascular sclerosis, gangrene, congelation (severe frostbite), alopecia, eczema, ulcers, lymphedema (parasite induced, for example elephantiasis/elephantitis, or tumor induced), vascular hyperplasia, hemangioma, diabetic induced retinopathy, macular degenerative disease, psoriasis, or endometriosis.

The present disclosure includes administering an inhibitor of apelin-36 (42-57) (for instance an inhibitor that is specific for this peptide or its receptor, such as a neutralizing monoclonal antibody, a small molecule inhibitor, the free-acid form of apelin-36 (42-57), or salcut-Gly) or a combination of an apelin-36 (42-57) inhibitor and one or more other pharmaceutical agents, to the subject in a pharmaceutically compatible carrier and in an amount effective to inhibit the condition, development or progression of the disorder. For example, other pharmaceutical agents may include one or more effective doses of another drug recognized for treatment of abnormal cell growth (such as one or more of those discussed at pages 260-269 of "Cecil Textbook of Medicine" (1992) W. B. Saunders).

Although the treatments described herein can be used prophylactically in any subject in a demographic group at significant risk for the disclosed disorders, subjects can also be selected using more specific criteria, such as a definitive diagnosis of the condition. For example, treatment can be initiated in a subject having signs and symptoms of a tumor or hypertension, which are recognized by those of ordinary skill.

A. Administration of Peptides or Peptide Analogs

Apelin peptides (the modified or unmodified forms) and inhibitors thereof can be administered directly to the subject. For example, an apelin-36 (42-57) peptide (amidated or free-acid forms) can be expressed in vitro, such as in an *E. coli* expression system, as is well known in the art, and isolated in amounts useful for therapeutic compositions.

In exemplary applications, therapeutic compositions are administered to a subject suffering from a disorder, such as neoplasia, cardiovascular disease, peripheral vascular disease, hypertension, preeclampsia syndrome, abnormal angiogenesis, diabetes, ocular degeneration, idiopathic pulmonary fibrosis, wound healing, altered mast cell migration, chronic obstructive pulmonary disease, inflammatory diseases such as arthritis (juvenile and rheumatoid) and inflammatory bowel disease, avascular or ischemic insult, myocardial infarction, stroke, vasculititis/angiitis, systemic or vascular sclerosis, gangrene, congelation (severe frostbite), alopecia, eczema, ulcers, lymphedema (parasite induced, for example elephantiasis/elephantitis, or tumor induced), vascular hyperplasia, hemangioma, diabetic induced retinopathy, macular degenerative disease, psoriasis, or endometriosis, in an amount sufficient to inhibit or treat the disorder. Amounts effective for this use will depend upon the severity of the disorder and the general state of the subject's health. A therapeutically effective amount of the compound is that which provides either subjective relief of a symptom(s) or an objectively identifiable improvement as noted by the clinician or other qualified observer.

An apelin-36 (42-57) peptide (amidated or free-acid forms) can be administered by any means known to one of skill in the art (see, e.g., Banga, "Parenteral Controlled Delivery of Therapeutic Peptides and Proteins," in *Therapeutic Peptides and Proteins*, Technomic Publishing Co., Inc., Lancaster, Pa., 1995), such as by intramuscular, subcutaneous, or intravenous injection, but even oral, nasal, or anal administration is contemplated. In one embodiment, administration is by subcutaneous or intramuscular injection. To extend the time during which the apelin-36 (42-57) peptide is available to inhibit or treat a disorder, the apelin-36 (42-57) peptide can be provided as an implant, an oily injection, or as a particulate system. The particulate system can be a microparticle, a microcapsule, a microsphere, a nanocapsule, or similar particle (Banga, "Parenteral Controlled Delivery of Therapeutic Peptides and Proteins," in *Therapeutic Peptides and Proteins*, Technomic Publishing Co., Inc., Lancaster, Pa., 1995).

In one specific, non-limiting example, an apelin-36 (42-57) peptide is administered that includes one or more of the disclosed amino acid sequences (for example, SEQ ID NOs: 19, 22, 25, 28, 31, 34, 37, or 42).

In another specific, non-limiting example, the apelin-36 (42-57) peptide (amidated or free-acid form) is administered in a dosage that enhances angiogenesis, and optionally is administered in combination with a mitogenic agent; such agent need not be covalently linked, or even administered simultaneously with, the peptide that promotes angiogenesis. Such agents need not be covalently linked, or even administered simultaneously with, the apelin-36 (42-57) peptide.

In a further specific, non-limiting example, the apelin-36 (42-57) peptide (amidated or free-acid form) is administered in a dosage that inhibits angiogenesis, and optionally is administered in combination with a cell growth inhibiting agent. Such agents need not be covalently linked, or even administered simultaneously with, the apelin-36 (42-57) peptide.

In yet another specific, non-limiting example, the apelin-36 (42-57) peptide (amidated or free-acid form) is administered in a dosage that inhibits tumorigenesis, and optionally is administered in combination with a cell growth inhibiting agent. Such agents need not be covalently linked, or even administered simultaneously with, the apelin-36 (42-57) peptide.

B. Administration of Nucleic Acid Molecules

In some embodiments, administration of the apelin-36 (42-57) peptide (amidated or free-acid forms) can be achieved by an appropriate nucleic acid expression vector (or combination of vectors) which is administered so that it becomes intracellular, for example, by use of a retroviral vector (see U.S. Pat. No. 4,980,286), or by direct injection, or by use of microparticle bombardment (e.g., a gene gun; Biolistic, DuPont), or coating with lipids or cell-surface receptors or transfecting agents, or by administering it in linkage to a homeobox-like peptide which is known to enter the nucleus (see e.g., Joliot et al., *Proc. Natl. Acad. Sci.*, 88:1864-1868, 1991). Alternatively, the nucleic acid can be introduced intracellularly and incorporated within host cell DNA for expression, for example, by homologous or non-homologous recombination.

Use of a DNA expression vector (e.g., the vector pcDNA) is an example of a method of introducing the foreign cDNA into a cell under the control of a strong viral promoter (e.g., cytomegalovirus) to drive the expression. However, other vectors can be used. Other retroviral vectors (such as pRETRO-ON, BD Biosciences, Palo Alto, Calif.) also use this promoter but have the advantages of entering cells without any transfection aid, integrating into the genome of target cells only when the target cell is dividing. It is also possible to turn on the expression of a therapeutic nucleic acid by administering tetracycline when these plasmids are used. Hence these plasmids can be allowed to transfect the cells, then administer a course of tetracycline to achieve regulated expression.

Other plasmid vectors, such as pMAM-neo (BD Biosciences, Palo Alto, Calif.) or pMSG (Invitrogen, Carlsbad, Calif.) use the MMTV-LTR promoter (which can be regulated with steroids) or the SV10 late promoter (pSVL, Invitrogen, Carlsbad, Calif.) or metallothionein-responsive promoter (pBPV, Invitrogen, Carlsbad, Calif.) and other viral vectors, including retroviruses. Examples of other viral vectors include adenovirus, AAV (adeno-associated virus), recombinant HSV, poxviruses (vaccinia) and recombinant lentivirus (such as HIV). All these vectors achieve the basic goal of delivering into the target cell the cDNA sequence and control elements needed for transcription.

Retroviruses have been considered a preferred vector for gene therapy, with a high efficiency of infection and stable integration and expression (Orkin et al., *Prog. Med. Genet.* 7:130-142, 1988). A nucleic acid encoding the apelin-36 (42-57) peptide can be cloned into a retroviral vector and driven from either its endogenous promoter (where applicable) or from the retroviral LTR (long terminal repeat). Other viral transfection systems may also be utilized for this type of approach, including adenovirus, AAV (McLaughlin et al., *J. Virol.* 62:1963-1973, 1988), vaccinia virus (Moss et al., *Annu. Rev. Immunol.* 5:305-324, 1987), Bovine Papilloma virus (Rasmussen et al., *Methods Enzymol.* 139:642-654, 1987) or members of the herpesvirus group such as Epstein-Barr virus (Margolskee et al., *Mol. Cell. Biol.* 8:2837-2847, 1988).

In addition to delivery of a nucleic acid encoding the apelin-36 (42-57) peptide (amidated or free-acid forms) to cells using viral vectors, it is possible to use non-infectious methods of delivery. For instance, lipidic and liposome-mediated gene delivery has recently been used successfully for transfection with various genes (for reviews, see Templeton and Lasic, *Mol. Biotechnol.*, 11:175-180, 1999; Lee and Huang, *Crit. Rev. Ther. Drug Carrier Syst.*, 14:173-206, 1997; and Cooper, *Semin. Oncol.*, 23:172-187, 1996). For instance, cationic liposomes have been analyzed for their ability to transfect monocytic leukemia cells, and shown to be a viable alternative to using viral vectors (de Lima et al., *Mol. Membr. Biol.*, 16:103-109, 1999). Such cationic liposomes can also be targeted to specific cells through the inclusion of, for instance, monoclonal antibodies or other appropriate targeting ligands (Kao et al., *Cancer Gene Ther.*, 3:250-256, 1996).

C. Representative Methods of Administration, Formulations and Dosage

The provided apelin-36 (42-57) peptides (amidated or free-acid forms), constructs, or vectors encoding such peptides, can be combined with a pharmaceutically acceptable carrier (e.g., a phospholipid or other type of lipid) or vehicle for administration to human or animal subjects. In some embodiments, more than one apelin-36 (42-57) peptide can be combined to form a single preparation. The apelin-36 (42-57) peptides can be conveniently presented in unit dosage form and prepared using conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers. Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of a sterile liquid carrier, for example, water for injections, immediately prior to use. Extemporaneous injection solutions and suspensions may be prepared from sterile powders, granules and tablets commonly used by one of ordinary skill in the art.

In certain embodiments, unit dosage formulations are those containing a dose or unit, or an appropriate fraction thereof, of the administered ingredient. It should be understood that in addition to the ingredients particularly mentioned above, formulations encompassed herein may include other agents commonly used by one of ordinary skill in the art.

The pharmaceutical compositions provided herein, including those for use in treating disorders such as neoplasia, cardiovascular disease, peripheral vascular disease, hypertension, preeclampsia syndrome, abnormal angiogenesis, diabetes, ocular degeneration, idiopathic pulmonary fibrosis, wound healing, altered mast cell migration, chronic obstructive pulmonary disease, inflammatory diseases such as arthritis (juvenile and rheumatoid) and inflammatory bowel disease, cardiovascular disease, avascular or ischemic insult, myocardial infarction, stroke, vasculititis/angiitis, systemic or vascular sclerosis, gangrene, congelation (severe frostbite), alopecia, eczema, ulcers, lymphedema (parasite induced, for example elephantiasis/elephantitis, or tumor induced), vascular hyperplasia, hemangioma, diabetic induced retinopathy, macular degenerative disease, psoriasis, or endometriosis, may be administered through different routes, such as oral, including buccal and sublingual, rectal, parenteral, aerosol, nasal, intramuscular, subcutaneous, intradermal, and topical. They may be administered in different forms, including but not limited to solutions, emulsions and suspensions, microspheres, particles, microparticles, nanoparticles, and liposomes.

It may be desirable to administer the pharmaceutical compositions locally to the area in need of treatment. This may be achieved by, for example, and not by way of limitation, local or regional infusion or perfusion during surgery, topical application (e.g., wound dressing), injection, catheter, suppository, or implant (e.g., implants formed from porous, non-porous, or gelatinous materials, including membranes, such as sialastic membranes or fibers), and the like.

In a specific embodiment, one or more of the disclosed peptides capable of modulating cell growth may be associated either by coating or impregnating an implant such as stent to treat a vascular disorder. These peptides are prepared and purified as described herein. In an example, the implant can be partially or completely coated with the peptide. For instance, the luminal surface of the implant may be coated with the peptide. The peptide may be attached to the implant by any chemical or mechanical bond or force, including linking agents. Alternatively, the coating may be directly linked (tethered) to the first surface, such as through silane groups. In other examples, the implant may be impregnated with at least one peptide by methods known to those of skill in the art so that multiple surfaces (such as the outer and inner surfaces) of the implant include the peptide.

In an additional embodiment, the implant may be coated or impregnated with materials in addition to the disclosed peptides to further enhance their bio-utility. Examples of suitable coatings are medicated coatings, drug-eluting coatings, hydrophilic coatings, smoothing coatings.

In one embodiment, administration can be by direct injection at the site (or former site) of a tissue that is to be treated, such as the peripheral vasculature or a tumor. In another embodiment, the pharmaceutical compositions are delivered in a vesicle, in particular liposomes (see, e.g., Langer, *Science* 249:1527-1533, 1990; Treat et al., in *Liposomes in the Therapy of Infectious Disease and Cancer*, Lopez-Berestein and Fidler (eds.), Liss, N.Y., pp. 353-365, 1989).

In yet another embodiment, the pharmaceutical compositions can be delivered in a controlled release system. In one embodiment, a pump can be used (see, e.g., Langer *Science* 249:1527-1533, 1990; Sefton *Crit. Rev. Biomed. Eng.* 14:201-240, 1987; Buchwald et al., *Surgery* 88:507-516, 1980; Saudek et al., *N. Engl. J. Med.* 321:574-579, 1989). In another embodiment, polymeric materials can be used (see, e.g., Ranger et al., *Macromol. Sci. Rev. Macromol. Chem.* 23:61-64, 1983; Levy et al., *Science* 228:190-192, 1985; During et al., *Ann. Neurol.* 25:351-356, 1989; and Howard et al., *J. Neurosurg.* 71:105-112, 1989). Other controlled release systems, such as those discussed in the review by Langer (*Science* 249:1527-1533, 1990), can also be used.

The amount of the pharmaceutical compositions that will be effective depends on the nature of the disorder or condition to be treated, as well as the stage of the disorder or condition. Effective amounts can be determined by standard clinical techniques. The precise dose to be employed in the formulation will also depend on the route of administration, and should be decided according to the judgment of the health care practitioner and each subject's circumstances. For example, a therapeutically effective amount of an active ingredient can vary from about 0.001 mg/kg body weight to about 1 g/kg body weight. Another example of such a dosage range is 0.1 to 200 mg/kg body weight in single or divided doses. A further example of a dosage range is 1.0 to 100 mg/kg body weight in single or divided doses. Alternatively, therapeutically effective amounts can be calculated in moles, for instance from about 0.5 nmol/kg to about 100 nmol/kg or more of an active ingredient. It is recognized that salcut peptides, including salcut-NH2, salcut-OH, or salcut-Gly, are administered such that their circulating concentrations are in a physiologic range.

The specific dose level and frequency of dosage for any particular subject may be varied and will depend upon a variety of factors, including the activity of the specific compound, the metabolic stability and length of action of that compound, the age, body weight, general health, sex, diet, mode and time of administration, rate of excretion, drug combination, and severity of the condition of the subject undergoing therapy.

The pharmaceutical compositions of the present disclosure can be administered at about the same dose throughout a treatment period, in an escalating dose regimen, or in a loading-dose regime (e.g., in which the loading dose is about two to five times the maintenance dose). In some embodiments, the dose is varied during the course of a treatment based on the condition of the subject being treated, the severity of the disease or condition, the apparent response to the therapy, and/or other factors as judged by one of ordinary skill in the art. The volume of administration will vary depending on the route of administration. By way of example, intramuscular injections may range from about 0.1 ml to about 1.0 ml. Those of ordinary skill in the art will know appropriate volumes for different routes of administration.

XI. Methods of Screening for Inhibitors or Activators of Apelin-36 (42-57) Activity In certain circumstances, it is desirable to reduce or inhibit the activity of apelin-36 (42-57), for example, for the treatment of neoplasia or abnormal angiogenesis. An effect can be achieved by inhibiting apelin-36 (42-57) activity (amidated or free-acid forms) in vitro or in vivo. In particular embodiments, apelin-36 (42-57) activity is inhibited by administering an apelin-36 (42-57) inhibitor to a subject. In other embodiments, apelin-36 (42-57) activity is inhibited by administering an apelin-36 (42-57) inhibitor to a cell in vitro. Such an inhibitor can be identified in a screening assay for inhibitors of apelin-36 (42-57)-mediated angiogenesis or tumor cell growth.

In other embodiments, it is desirable to activate or augment the activity of apelin-36 (42-57), for example, for the treatment of abnormal angiogenesis. An effect can be achieved by increasing apelin-36 (42-57) activity (amidated or free-acid forms) in vitro or in vivo. In particular embodiments, apelin-36 (42-57) activity is augmented by administering an apelin-36 (42-57) activator to a subject. In other embodiments, apelin-36 (42-57) activity is augmented by administering an apelin-36 (42-57) activator to a cell in vitro. Such an activator can be identified in a screening assay for activators of apelin-36 (42-57)-mediated angiogenesis.

In general, a screening assay is carried out by determining whether a given test compound inhibits (or activates) apelin-36 (42-57)-mediated cell growth or suppression; inhibition of apelin-36 (42-57)-mediated cell growth (at lower concentrations of apelin-36 42-57)) or decreased apelin-36 (42-57)-mediated growth suppression (at higher concentrations of apelin-36 (42-57)) indicates that the test compound is an apelin-36 (42-57) inhibitor. Augmentation of apelin-36 (42-57)-mediated cell growth (at lower concentrations of apelin-36 42-57)) or increased apelin-36 (42-57)-mediated growth suppression (at higher concentrations of apelin-36 (42-57)) indicates that the test compound is an apelin-36 (42-57) activator. In some embodiments, this is accomplished by contacting cells (for example, endothelial cells or tumor cells) with apelin-36 (42-57) (amidated or free-acid forms) in the presence and absence of the test compound.

A reduction of apelin-36 (42-57)-induced cell growth at concentrations of 10 nM and below, for example as measured by reduced relative luminescent units in a cell proliferation assay or reduced endothelial cell tube formation, indicates that the test compound is an inhibitor of the mitogenic effect of apelin-36 (42-57). A reduction of apelin-36 (42-57)-induced cell suppression at concentrations of 10 nM and above, for example as measured by increased relative luminescent units in a cell proliferation assay or increased endothelial cell tube formation, indicates that the test compound is an inhibitor of the cell growth suppressive effect of apelin-36 (42-57). Similarly, an increase of apelin-36 (42-57)-induced cell growth at concentrations of 10 nM and below, for example as measured by increased relative luminescent units in a cell proliferation assay or endothelial cell tube formation, indicates that the test compound is an activator of the mitogenic effect of apelin-36 (42-57). An increase of apelin-36 (42-57)-induced cell suppression at concentrations of 10 nM and above, for example as measured by decreased relative luminescent units in a cell proliferation assay or decreased endothelial cell tube formation, indicates that the test compound is an activator of the cell growth suppressive effect of apelin-36 (42-57).

An apelin-36 (42-57) inhibitor can be any type of compound that is capable of opposing (inhibiting or reducing) a cell growth activity of apelin-36 (42-57), for example, an antibody (such as a neutralizing monoclonal antibody), a small molecule inhibitor, a receptor, a binding protein, or a peptide (for example, apelin-36 (42-58) or the free-acid form of apelin-36 (42-57)). An apelin-36 (42-57) activator can be any type of compound that is capable of enhancing (increasing or stimulating) a cell growth activity of apelin-36 (42-57), for example, an antibody (such as an activating monoclonal antibody), a small molecule, a receptor, a binding protein, or a peptide. Libraries of molecules useful for screening for inhibitors or activators are well known to those of ordinary skill in the art. See, for instance, published international application PCT/US02/23172 (WO 03/008627; incorporated herein by reference), which describes additional methods of screening for interacting molecules and libraries adapted for such screens.

XII. Kits

The compounds disclosed herein, and in particular apelin-36 (42-57) (amidated or free-acid forms) or an inhibitor of apelin-36 (42-57), can be supplied in the form of kits for use in modulating angiogenesis or inhibiting tumorigenesis, as well as in the prevention and/or other treatment of a specific disorder, condition or diseases (for example, cardiovascular disease, peripheral vascular disease, hypertension, preeclampsia syndrome, diabetes, ocular degeneration, idiopathic pulmonary fibrosis, wound healing, chronic obstructive pulmonary disease). In such a kit, a clinically effective amount of the active ingredient(s) is provided in one or more containers. The active ingredient(s) may be provided suspended in an aqueous solution or as a freeze-dried or lyophilized powder, for instance. In certain embodiments, it will be provided in the form of a pharmaceutical composition.

Kits according to certain embodiments of this disclosure can also include instructions, usually written instructions, to assist the user in treating a disorder, condition or disease with the apelin-36 (42-57) peptide. Still other kits, particularly those in which an inhibitor of apelin-36 (42-57) is provided, will include instructions to assist the user in treating a disorder, condition or disease with the apelin-36 (42-57) inhibitor. The instructions in kits can be for use of the active ingredient for any of the purposes described herein. Instructions can optionally be provided on a computer readable medium.

The container(s) in which an active ingredient, optionally with other compound(s), is supplied can be any conventional container that is capable of holding the supplied form, for instance, microfuge tubes, ampoules, or bottles. In some applications, the therapeutic compound may be provided in pre-measured single use amounts in individual, typically disposable, tubes or equivalent containers.

The amount of active ingredient (for example, apelin-36 (42-57) or an inhibitor of apelin-36 (42-57)) supplied in the kit can be any appropriate amount, depending for instance on the market to which the product is directed. For instance, if the kit is adapted for research or clinical use, the amount of vasoconstrictor compound provided would likely be an amount sufficient for several treatments.

Certain kits according to this disclosure will also include one or more other agents useful in treating the conditions disclosed herein. For example, such kits may include one or more effective doses of other agents or other agents useful in the treatment of particular conditions (such as an antibiotic in the treatment of septic shock). Still other kits will also include one or more effective doses of other drugs recognized for treatment of hypertension (such as those discussed in "Cecil Textbook of Medicine" (1992) W. B. Saunders, at pages 260-269 (incorporated herein by reference) for instance), or other agents useful in the treatment of particular conditions.

The subject matter of the present disclosure is further illustrated by the following non-limiting Examples.

EXAMPLES

Example 1

Production of Amide, Free-acid, and Glycine-Extended Forms of Apelin-36 (42-57) (Salcut-NH$_2$, Salcut-OH, and Salcut-Gly)

Apelin-36, apelin-13, (Pyr$^1$)-apelin-13, and (Ala$^{13}$)-apelin-13 were obtained commercially from Bachem (Switzerland). The amide, free-acid, and glycine extended forms of apelin-36 (42-57) were synthesized using standard techniques on an Applied Biosystems automated peptide synthesizer following manufacturer's instructions.

Example 2

Effect of salcut-NH$_2$ on a Variety of Endothelial and Epithelial Cell Lines

This example demonstrates the proliferative effect of salcut-NH$_2$ on a variety of cell types.

Proliferation response profiles of apelin, salcut-NH$_2$, salcut-Gly, and/or salcut-OH on a variety of endothelial and tumor cell lines or primary endothelial cells were obtained using the following method. Human blood vessel endothelial cells (HMEC-1), human primary microvascular dermal EC (dB1), human lymphatic endothelial cells (LEC), human mast cells (HMC-1), human breast cancer cells (MCF-7; T47D), human gastric cancer cells (HTB 103), human lung cancer cells (A549), monkey endothelial cells (CRL 1780), and porcine aortic endothelial cells (PAE) were seeded at 25,000 cells per well at 50 µl volume in appropriate media containing 0.5% serum in a 96 well plate. After overnight incubation the peptide was added in serum free media and cells were incubated for 3-5 days. To measure growth proliferation, the adenosine triphosphate ATPLITE™ one-step assay (PerkinElmer), which is based on firefly luciferase and has high sensitivity for quantification of viable cells, was used. Data were expressed as mean plus minus standard deviation. Statistical analyses were performed using Student's t-test, p values less than 0.05 were considered statistically significant.

Figure 3A:
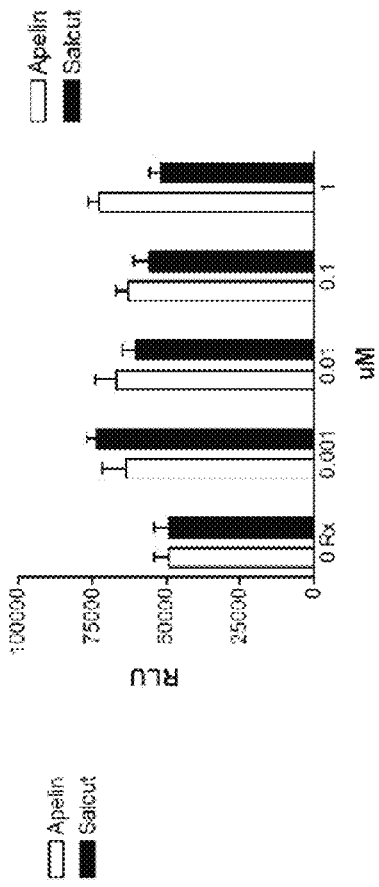
FIG. 3A shows the proliferative response of the MCF-7 human breast cancer (estrogen dependent) cell line in the presence of both apelin-13 (65-77) and apelin 36 (42-57).
Figure 3B:
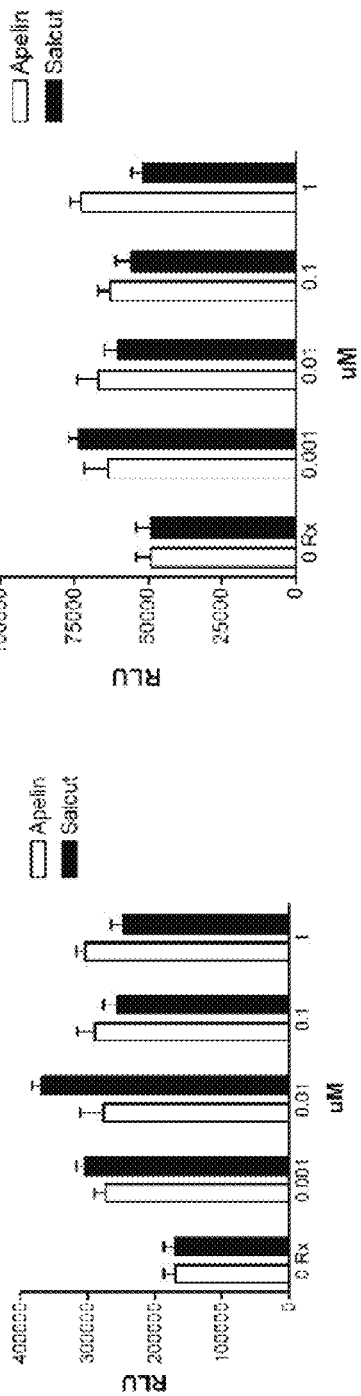
FIG. 3B shows the proliferative response of the T47D human breast cancer (estrogen-independent) cell line in the presence of both apelin-13 (65-77) and apelin-36 (42-57).
Figure 3C:
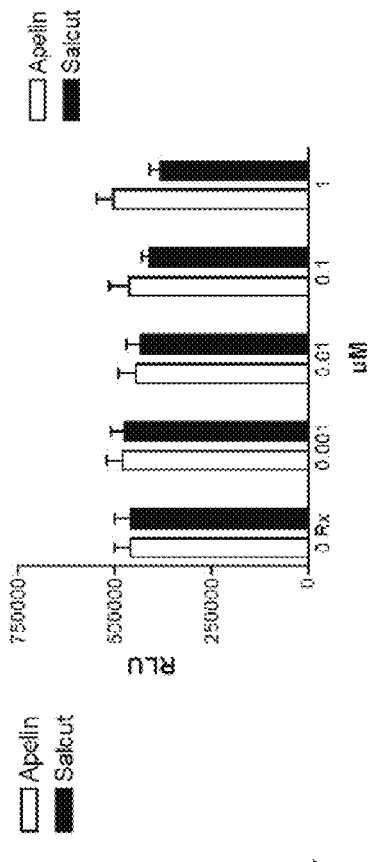
FIG. 3C shows the proliferative response of the HTB 103 human gastric cancer cell line in the presence of both apelin-13 (65-77) and apelin 36 (42-57).
Figure 3D:
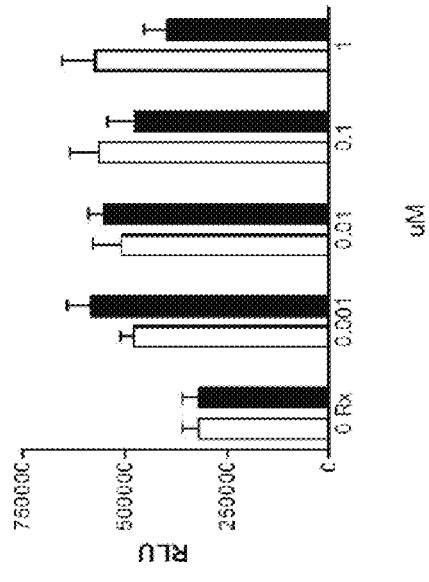
FIG. 3D shows the proliferative response of the A549 human lung cancer cell line in the presence of both apelin-13 (65-77) and apelin 36 (42-57).
Figure 3E:
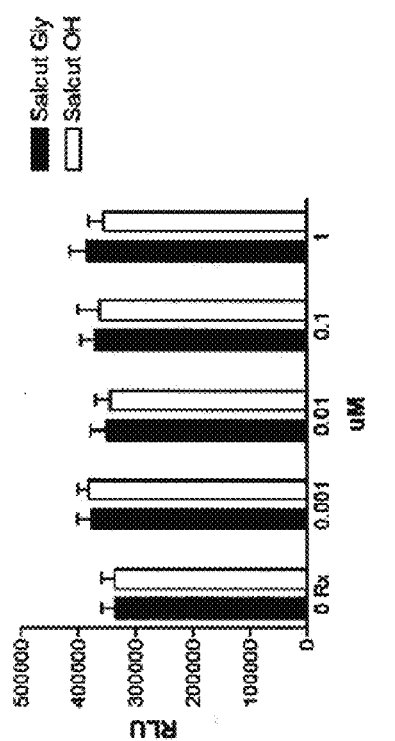
FIG. 3E shows the proliferative response of the HMEC-1 human blood vessel endothelial cell line in the presence of both apelin-13 (65-77) and apelin 36 (42-57).
Figure 3F:
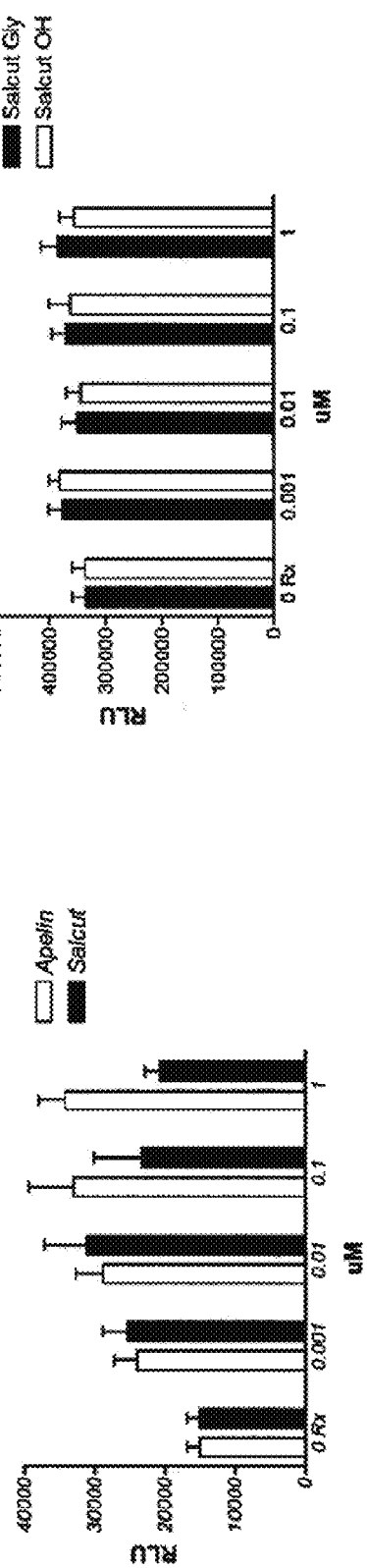
FIG. 3F shows the proliferative response of the HMEC-1 human blood vessel endothelial cell line in the presence of both the free acid form of apelin-36 (42-57) and apelin 36 (42-58).
Figure 3G:
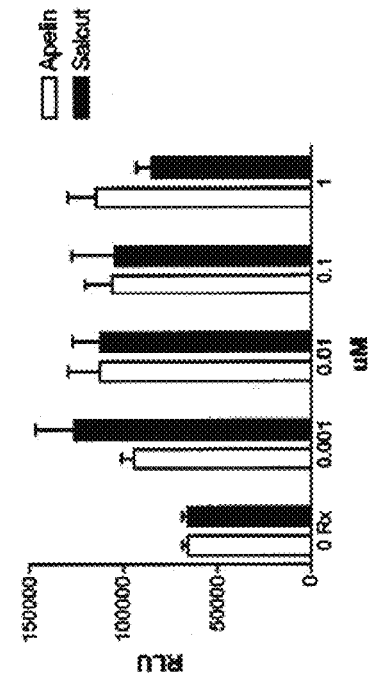
FIG. 3G shows the proliferative response of porcine aortic endothelial (PAE) cells in the presence of both apelin-13 (65-77) and apelin 36 (42-57).
Figure 3H:
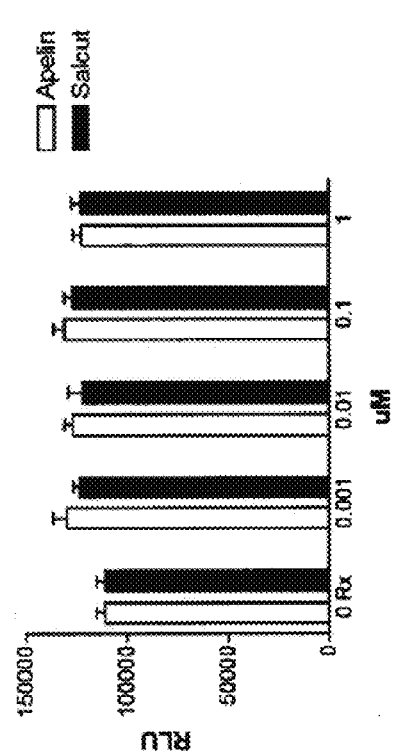
FIG. 3H shows the proliferative response of human primary microvascular dermal endothelial cells in the presence of both apelin-13 (65-77) and apelin 36 (42-57).
Figure 3L:
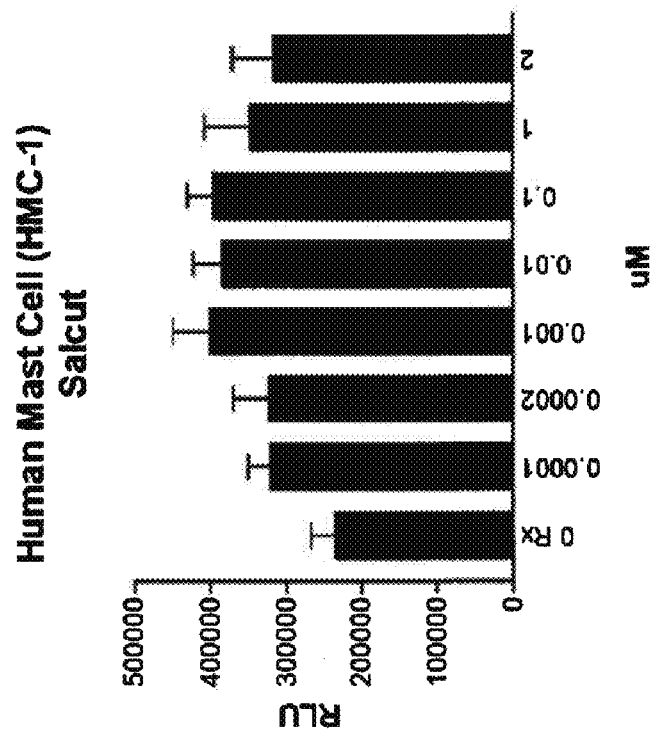
FIG. 3L shows the proliferative response of the HMC-1 human mast cell line in the presence of apelin-13 (65-77).
Figure 3M:
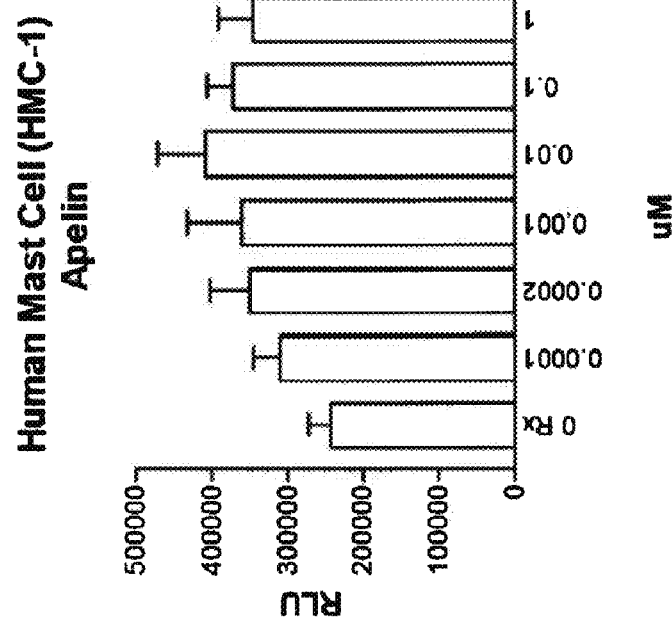
FIG. 3M shows the proliferative response of the HMC-1 human mast cell line in the presence of apelin 36 (42-57).
Figure 3N:
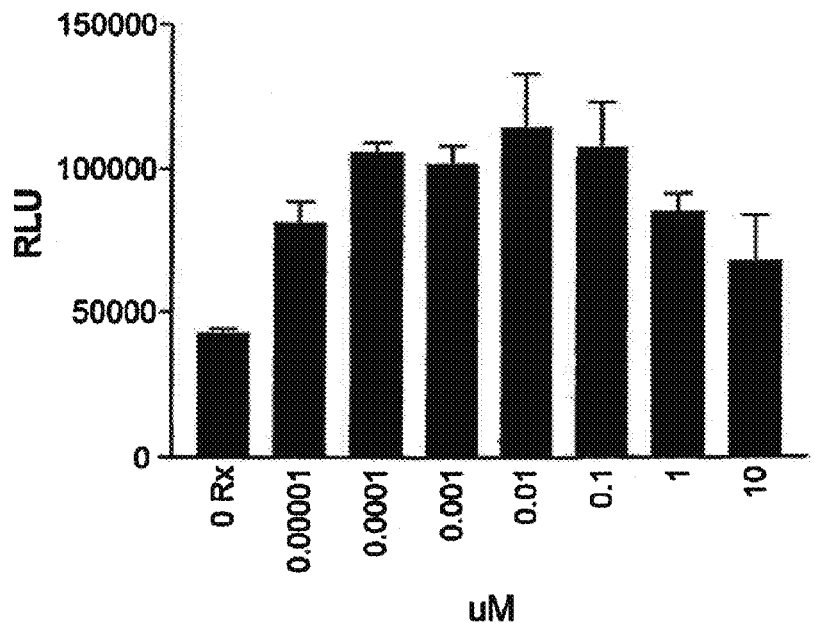
FIG. 3N shows the proliferative response of the HTB 103 human gastric cancer cell line in the presence of apelin 36 (42-57).

FIGS. 3A-3C, 3E, and 3G-3O show that the cell proliferation (as measured by relative luminescent units [RLU]) increases in the presence of both apelin-13 (65-77) and the amidated form of apelin-36 (42-57) (salcut-NH$_2$), compared to cells cultured in the absence of these compounds (0 Rx), and that the maximal increase in proliferation occurs within the concentration range of 10 nM and 100 pM salcut-NH$_2$. In contrast, FIG. 3D shows that neither apelin-13 (65-77) nor salcut-NH$_2$ affect proliferation of the human lung cancer cell line A549 in the 10 nM to 100 pM range. Side-by-side graphs of the effect of apelin-13 and salcut-NH$_2$ (FIG. 3E), as well as salcut-Gly and salcut-OH (FIG. 3F), on human blood vessel endothelial (HMEC-1) cells demonstrate that while apelin-13 (65-77) and salcut-NH2 are potent stimulators of HMEC-1 proliferation, salcut-OH and salcut-Gly have a minor effect on proliferation of these cells.

Figure 3O:
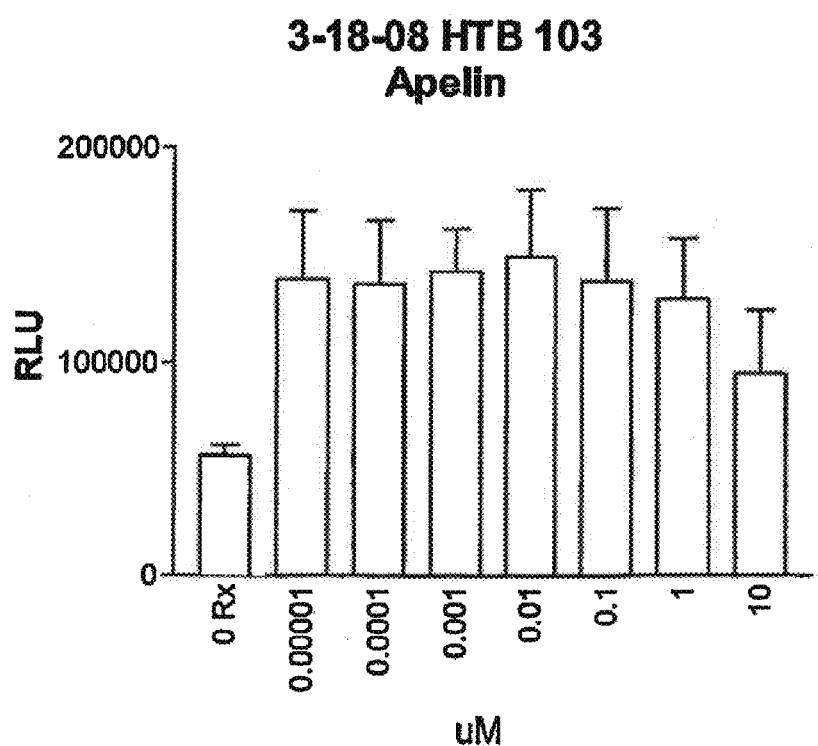
FIG. 3O shows the proliferative response of the HTB 103 human gastric cancer cell line in the presence of apelin 13 (65-77). RLU (relative luminescent units) value is proportional to proliferation or cell growth.

FIGS. 3A-3D, 3E, and 3G, 3I-3O show that salcut-NH2 concentrations of 10 nM and greater have a suppressive effect on cell proliferation in these cells, whereas apelin-13 (65-77) maintains its positive effect on proliferation. FIG. 3D shows that although salcut-NH$_2$ does not stimulate proliferation, it has a cell growth suppressive effect at higher concentrations. FIG. 3O shows that at high enough concentrations of apelin-13 (65-77) (for example, at 10 µM), a suppressive effect may be seen. This biphasic (rise and fall) response is indicative of two different receptors being involved in modulating the proliferative response: (i) a high affinity receptor involved in cell growth stimulation/proliferation at lower concentrations of salcut-NH$_2$ (10 nM and below) and (ii) a low affinity receptor involved in cell growth inhibition or suppression at higher concentrations of salcut-NH$_2$ (10 nM and above).

Figure 4:
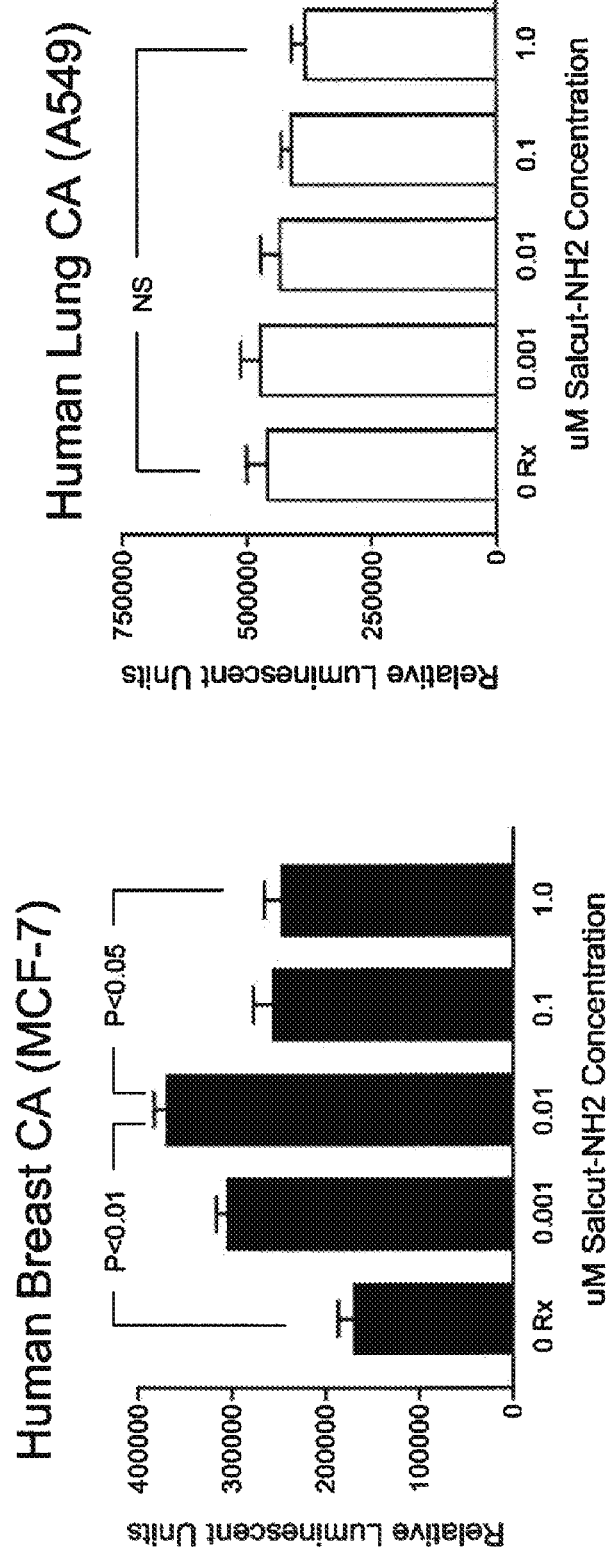
FIG. 4 is a series of graphs demonstrating the proliferative response of two cancer cell lines to apelin 36 (42-57) (salcut-$NH_2$) over a 1 nM to 1 µM dose range.

FIG. 4 shows the biphasic (rise and fall) response of salcut-NH$_2$ on growth of the human breast cancer cell line MCF-7, whereas the human lung cancer cell line A549 did not respond in a statistically significant manner to higher concentrations of salcut-NH$_2$ by inhibiting proliferation, although there is a downward trend in proliferation with increasing concentration of salcut-NH$_2$.

Figure 5:
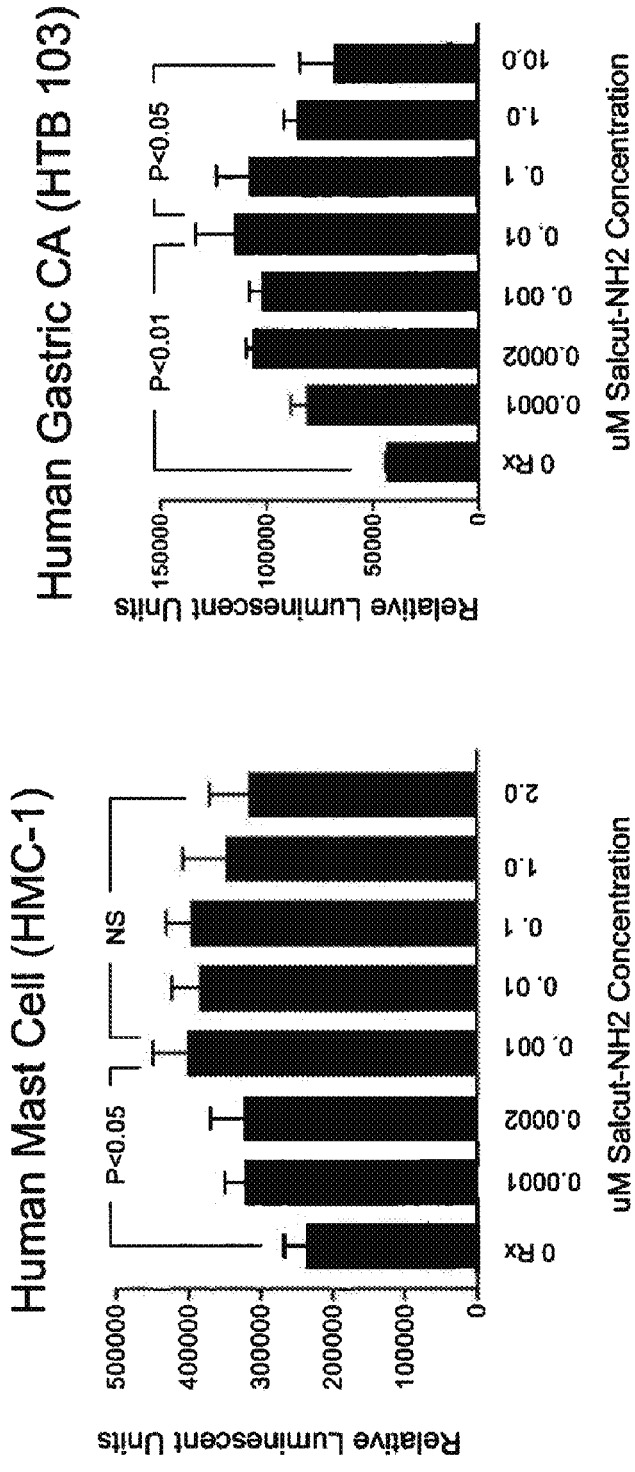
FIG. 5 is a series of graphs demonstrating the proliferative response of two human cell lines to various concentrations of apelin 36 (42-57) (salcut-$NH_2$).

FIG. 5 shows the biphasic (rise and fall) response of salcut-NH$_2$ on growth of the human gastric cancer cell line HTB-103, whereas the human mast cell line HMC-1 only responded to lower concentrations of salcut-NH$_2$ by stimulating proliferation in a statistically significant manner.

Figure 6:
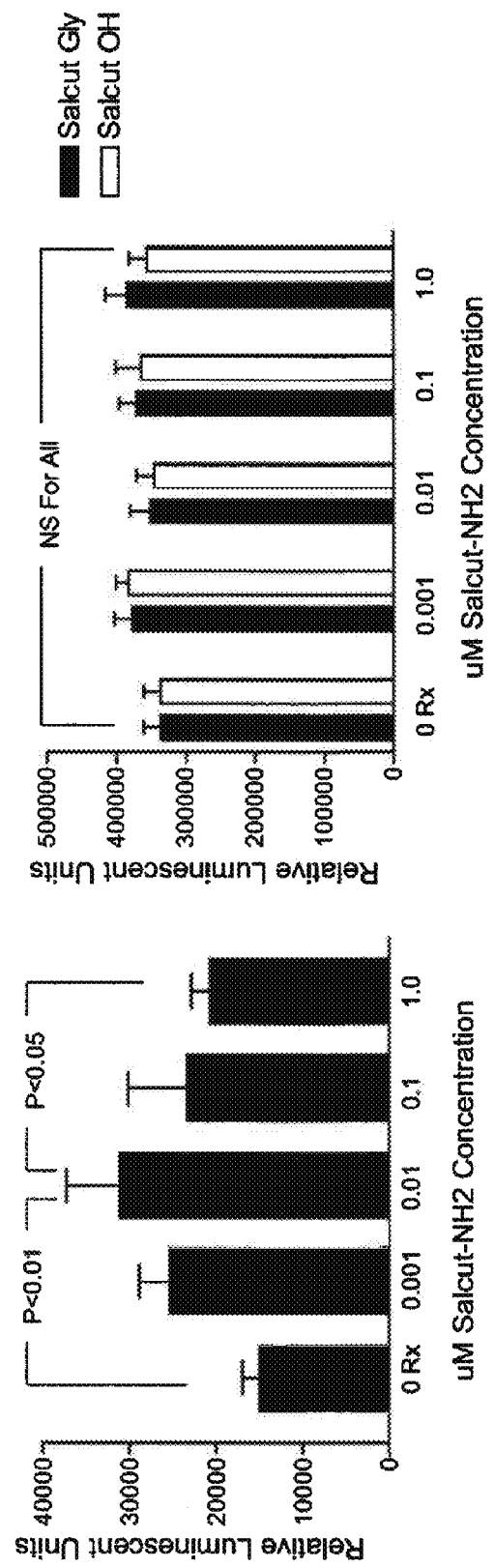
FIG. 6 is a series of graphs demonstrating the proliferative response of the HMEC-1 human blood vessel endothelial cell line to various concentrations of apelin 36 (42-57) (salcut-$NH_2$), the free acid form of apelin 36 (42-57) (salcut OH), and apelin 37 (42-58) (salcut Gly).

FIG. 6 shows the biphasic (rise and fall) response of salcut-NH$_2$ on growth of the human blood endothelial cell line HMEC-1, whereas the salcut-OH and salcut-Gly do not have a statistically significant effect on cell growth.

Example 3

Tube Formation Assay

This example demonstrates the effect of salcut-NH$_2$ on endothelial cells using an in vitro tube formation assay.

Porcine aortic endothelial (PAE) cells were stably transfected with Green Fluorescent Protein (GFP) and seeded at a concentration of 18,000 cells per well of a 96-well culture plate. The wells were coated with GELTREX™ basement membrane matrix (Invitrogen, CA). Cells were resuspended in medium at a concentration of $2.25 \times 10^5$ to $2.5 \times 10^5$ cells/ml. An 80 cell suspension (18,000-20,000) cells were added per well. Positive control cells were cultured with medium supplemented with 1.0% fetal bovine serum (FBS). Negative control cells were cultured with serum-free medium. Cells were incubated at 37° C. with salcut-NH$_2$. Salcut-NH$_2$ was added to each well to give the following concentrations: 0.1 pM, 1.0 pM, 10 pM, 100 pM, 1 nM, 10 nM, 100 nM, 1 µM, and 10 µM. After three or more hours of incubation, cells were assessed for tube formation and were photographed. Assays were performed in triplicate.

Figure 7:
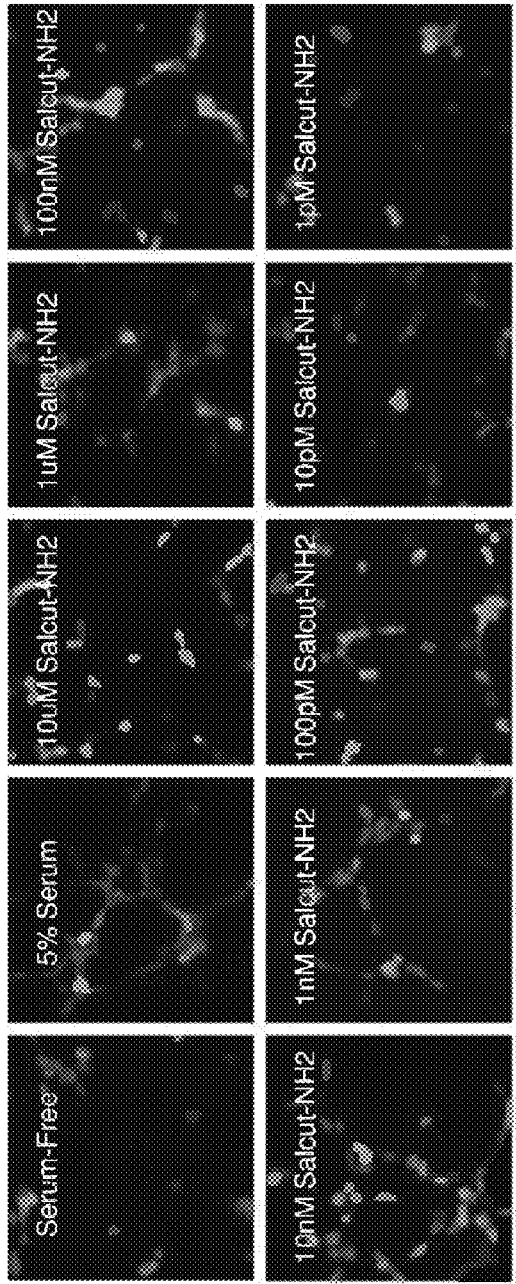
FIG. 7 is a series of immunofluorescence images demonstrating the effect of various concentrations of apelin 36 (42-57) (salcut-$NH_2$), the free acid form of apelin 36 (42-57), or apelin 36 (42-58) on porcine aortic endothelial cell tube formation.

Endothelial cell tubes began to form with as little as 1.0 pM to 10 pM of salcut-NH$_2$ peptide, compared to the negative control sample (FIG. 7). Maximum tube formation occurred between 100 pM and 10 nM of salcut-NH2 and then a suppressive effect was observed at concentrations exceeding 10 nM salcut-NH$_2$, with 10 µM giving similar results as the negative control well. 1 nM and 10 nM concentrations of salcut-OH and salcut-Gly also gave similar results as the negative control.

Figure 8:
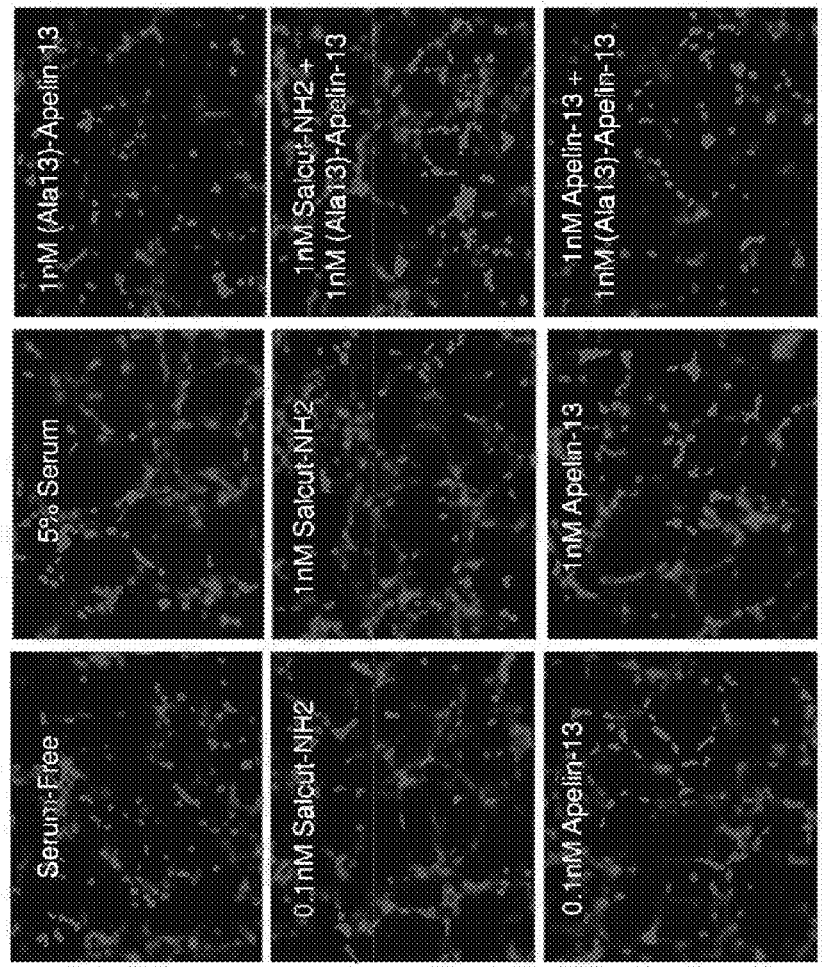
FIG. 8 is a series of immunofluorescence images demonstrating the effect of the APJ receptor antagonist ala13-apelin 13 (also known as apelin-12 (F13A)) on endothelial cell tube formation in the presence of apelin 36 (42-57) (salcut-$NH_2$) and apelin 13 (65-77).

Formation of endothelial cell tubes in the presence of 1 nM salcut-NH$_2$ was not inhibited by the APJ receptor peptide antagonist (Ala13)-apelin-13 (where the carboxy-terminal phenylalanine is substituted with an alanine) (FIG. 8 and FIG. 13). In contrast, (Ala13)-apelin-13 inhibited endothelial cell tube formation in the presence of 1 nM apelin-13 (FIG. 8). As the effect of salcut-NH$_2$ is not altered by the APJ receptor antagonist, these results indicate that salcut-NH$_2$ does not act through the APJ receptor. Instead, salcut-NH$_2$ mediates its effect through a different receptor or receptor complex. Thus, salcut-NH$_2$ and apelin-13 act via different mechanisms.

Example 4

Production of Polyclonal Antibody Directed Against Apelin-36 (42-57) Amide (Salcut-NH$_2$)

Polyclonal serum directed against salcut-NH$_2$ was generated using standard protocols (see, for example, Harlow and Lane (*Antibodies, A Laboratory Manual*, CSHL, New York, 1988). This example describes quantitation experiments which were used to determine the sensitivity of the anti-salcut-NH$_2$ polyclonal antiserum at different dilutions. Also described are titration assays of the anti-salcut-NH$_2$ polyclonal antiserum using ELISA.

Titration Protocol Binding to C-Salcut-NH$_2$ or Salcut-NH$_2$

Solid phase cysteine-salcut-NH$_2$ (C-salcut-NH$_2$; modified cross-linker immunogen; Rows A, B, C of a 96 well plate), Apelin-36 (Rows D, E, F), and Apelin-13 (Rows G and H) were applied to a 96 well plate at 100 ng/50 µl/well and incubated for 2 hours at room temperature (or overnight at 4° C.). The solution containing unbound immunogen was then aspirated and the wells were blocked with 1% bovine serum albumin (BSA) in phosphate buffered saline (PBS) for 1 hour at room temperature. The blocking solution was aspirated and the wells were washed three times with PBS. Serial dilutions of 50 µl of rabbit polyclonal anti-salcut-NH$_2$ (from a 1:100 to 1:204,800 dilution, columns 1-12 of the 96 well plate) previously absorbed three times with solid phased (i) BSA (Rows A, D, and G), (ii) Apelin-36 (Rows B and E), or (iii) C-salcut-NH$_2$ (Rows C, F, and H) were applied to the wells and were incubated at room temperature for 1.5 hours. The anti-serum was aspirated and the wells washed three times with PBS. Goat anti-rabbit IgG-horseradish peroxidase (HRP) secondary antibody reagent (50 µl) was added to the wells at a 1:500 dilution in 1% BSA in PBS. The wells were incubated for 1 hour at room temperature, then aspirated and washed four times with PBS. In order to visualize the antibody binding, 100 µl of Stabilized Chromogen (Biosource) was applied to the wells and the wells were incubated in the dark for 30 minutes at room temperature. Stop Solution (100 µl) was added and the samples were immediately read at 450 nm on a TECAN Infinite M200 multi-reader scanner.

Figure 11:
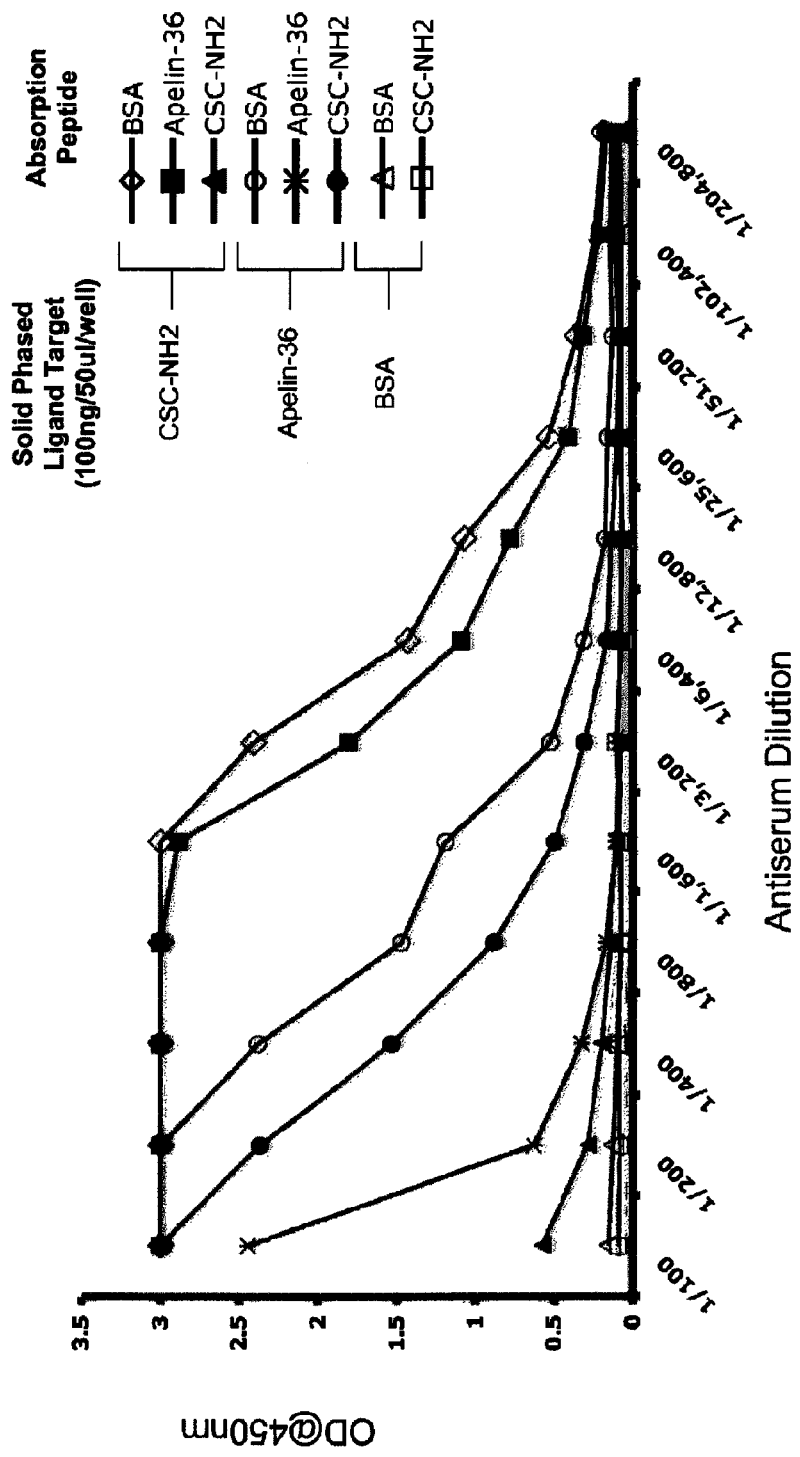
FIG. 11 is a graph demonstrating an ELISA titration curve using different absorption peptides and different solid phased ligand targets. Antibodies with bovine serum albumin (BSA) or Apelin-36 bind effectively to CSC-$NH_2$ (cysteine-salcut-$NH_2$, a modified cross-linker immunogen) (◊, ■), but antibodies with CSC-$NH_2$ dramatically block binding to CSC-$NH_2$ (▲). Antibodies with BSA or CSC-$NH_2$ bind to Apelin-36 (○, ●), but antibodies with Apelin-36 block binding to Apelin-36 (X).

The results of the ELISA titration curve, using different adsorption peptides and different solid phased ligand targets, are shown in FIG. 11. When the antiserum is preabsorbed with BSA or apelin-36, the resulting cleared antiserum still effectively binds to solid phased C-salcut-NH2, but when it is preabsorbed to C-salcut-NH$_2$ binding to C-salcut-NH$_2$ is almost completely blocked, even at the lowest dilution of antiserum, demonstrating the specificity of the antiserum for salcut-NH$_2$ and/or the carboxy-terminal amidated glycine residue. Given the close similarity of the primary amino acid sequence between the amino-terminus of apelin-36 and C-salcut-NH$_2$, the resulting binding data would indicate that unique immune epitopes exist on C-salcut-NH$_2$ (original immunogen) that do not exist on apelin-36, namely the carboxy-terminal amide. Antibodies to this immune epitope would only be removed by absorption with C-salcut-NH$_2$. Furthermore, when the antiserum is preabsorbed with BSA or C-salcut-NH$_2$, the antiserum is still capable of binding to solid phased apelin-36, indicating the presence of residual antibodies that remain following C-salcut-NH$_2$ absorption and recognize immune epitopes on apelin-36. Given the large portion of antibodies that exist towards the amide, it is presumed that during the absorption process, due to proportional differences, weighted antibodies binding to the amide residue block the attachment of glycine directed antibodies to C-salcut-NH$_2$ via steric hindrance and thus remain free to bind to the regional glycine residue on solid phased apelin-36. Finally, when the antiserum is absorbed with apelin-36, binding to apelin-36 is blocked.

Quantitative ELISA Assay for Salcut-NH$_2$

Solid phase C-salcut-NH2 (immunogen) was applied to a 96 well plate either at 100 ng/50 µl/well (Rows A and B), 50 ng/50 µl/well (Rows C and D), 25 ng/50 µl/well (Rows E and F), or 12.5 ng/50 µl/well (Rows G and H) and incubated for one hour at room temperature.

The solution containing unbound immunogen was then aspirated and the wells were blocked with 1% BSA in PBS for 1 hour at room temperature. The blocking solution was aspirated and the wells were washed three times with PBS. 25 µl of 1% BSA in PBS (columns 1 and 12) or free C-salcut-NH$_2$ (10 pg, 50 pg, 100 pg, 500 pg, 1 ng, 5 ng, 10 ng, 50 ng, 100 ng, 500 ng; columns 2-11) in 1% BSA in PBS was added to the wells, followed by 25 µl of rabbit polyclonal anti-salcut-NH$_2$ (1:400 dilution). The wells were incubated at room temperature for 1.5 hours. The anti-serum was aspirated and the wells washed three times with PBS. Goat anti-rabbit IgG-horseradish peroxidase (HRP) secondary antibody reagent (50 µl) was added to the wells at a 1:500 dilution in 1% BSA in PBS. The wells were incubated for 1 hour at room temperature, then aspirated and washed four times with PBS. In order to visualize the antibody binding, 100 µl of Stabilized Chromogen (Biosource) was applied to the wells and the wells were incubated in the dark for 30 minutes at room temperature. Stop Solution (100 µl) was added and the samples were immediately read at 450 nm on a TECAN INFINITE® M200 multi-reader scanner.

Figure 10:
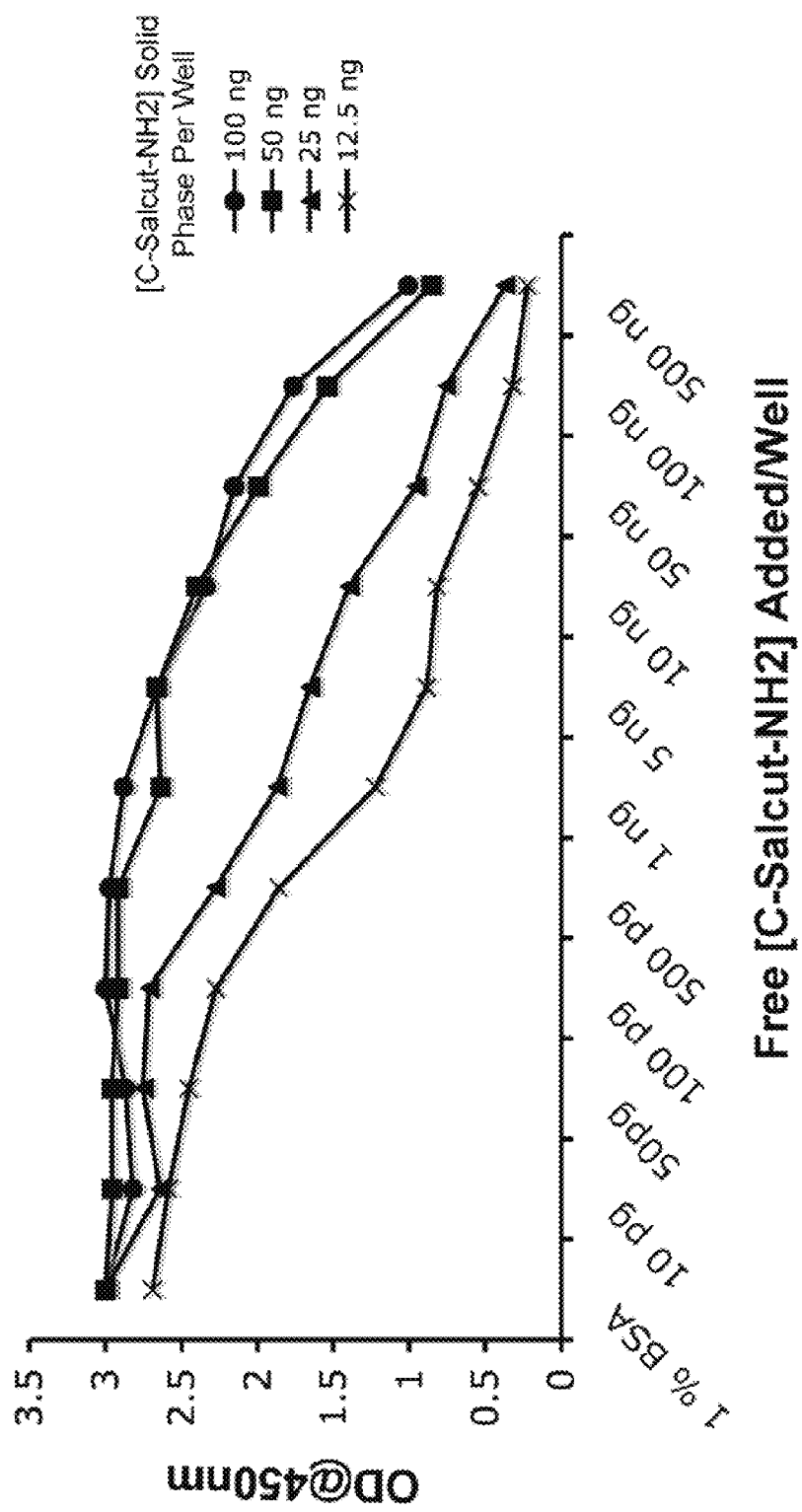
FIG. 10 is a graph demonstrating the sensitivity of the salcut-$NH_2$ quantitative ELISA when lowering the solid phase concentration of c-salcut-$NH_2$. As the solid phased [c-salcut-$NH_2$] is lowered, the resulting titration curve becomes more linear and the sensitivity (detectable peptide) increases.

The results of the quantitative ELISA are shown in FIG. 10 and demonstrate that sensitivity of the salcut-NH$_2$ antiserum was augmented by lowering the solid phase concentration of C-salcut-NH$_2$. Thus, as the concentration of the solid phased C-salcut-NH$_2$ is lowered, the resulting titration curve becomes more linear and the sensitivity (detectable peptide) increases.

Example 5

Nude Mouse Xenograft Studies

Six week old female nude mice were used in this study; ten mice were used per test group. A549 human bronchioloalveolar cancer cells were cultured at the SAIC/Frederick facility. 1×10$^7$ A549 cells were injected subcutaneously in the hindquarter of each nude mouse. The following treatment regime was started seven days following tumor injection: Group 1—PBS control; Group 2—salcut-NH$_2$ peptide (10 µM). Appropriate Groups were treated with 25 µl injections at four corners around the tumor, three times per week for five weeks. Mice were inspected, weighed, and tumors measured (H×W× L) three times per week with calipers. Following completion of the experiment, mice were euthanized, tumors excised, and cut into four pieces. Two segments were frozen and stored at −80° C. and two segments were paraffin embedded for pathology. Nude mice injected with the A549 cell line showed a dramatic reduction in tumor growth when treated with salcut-NH$_2$, compared to treatment with PBS alone.

Figure 12:
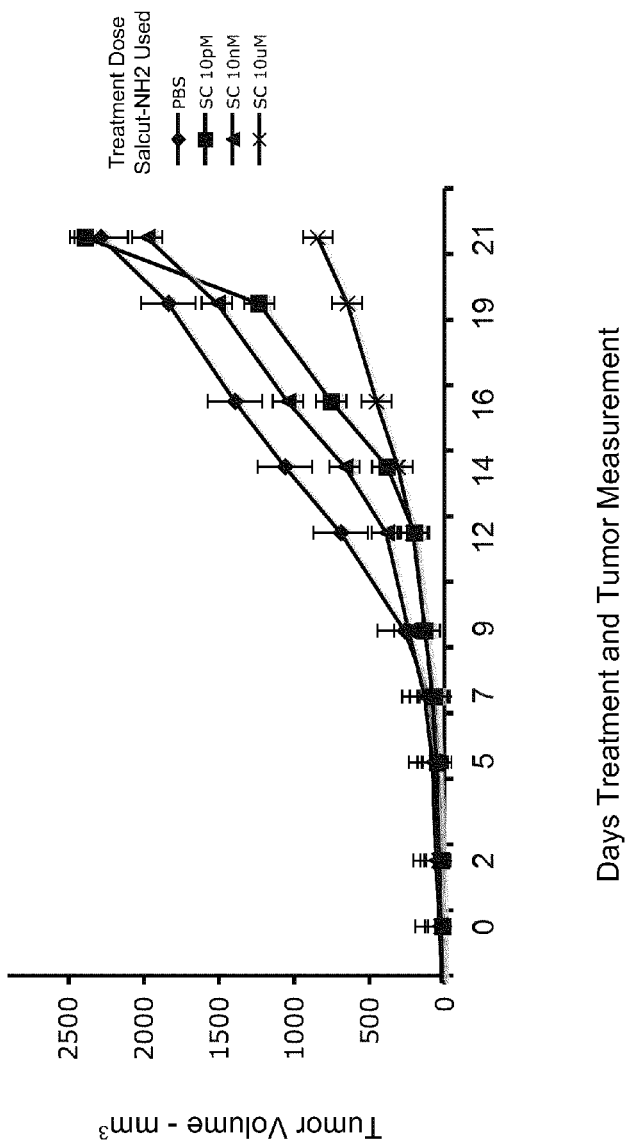
FIG. 12 is a graph demonstrating effects of salcut-$NH_2$ treatment on nude mouse xenograft growth of the human bronchioloalveolar cancer cell line A549.

In another experiment, six week old female nude mice were used in this study; ten mice were used per test group. A549 human bronchioloalveolar cancer cells were cultured at the SAIC/Frederick facility. 1×10$^7$ A549 cells were injected subcutaneously in the hindquarter of each nude mouse. The following treatment regime was started seven days following tumor injection: Group 1—PBS control; Group 2—salcut-NH$_2$ peptide (10 pM); Group 3—salcut-NH$_2$ peptide (10 nM); Group 4—salcut-NH$_2$ peptide (10 µM). Appropriate Groups were treated with 100 µl injections intraperitoneally, three times per week for four weeks. Mice were inspected, weighed, and tumors measured (H×W×L) three times per week with calipers. Following completion of the experiment, mice were euthanized, tumors excised, and cut into four pieces. Two segments were frozen and stored at −80° C. and two segments were paraffin embedded for pathology. FIG. 12 demonstrates reduced tumor growth in the presence of salcut-NH$_2$, compared to PBS, a highly statistically significant (<0.005) suppression of tumor growth in the presence of 10 µM salcut-NH$_2$.

Example 6

Effect of Salcut-NH$_2$ on Aortic Ring/Vessel Outcropping

This example measures the effect of various concentrations of salcut-NH$_2$ on a rat aortic ring assay.

On day 0, rats were euthanized and decapitated, and aortas were harvested and transferred to a culture dish containing EGM-2 with growth factors (20 ml media; Clonetics). Fibroadipose tissue and other non-aortic tissue were removed. Using dissecting microscope, the aorta was sectioned into 1 mm-long rings. Aortic rings were then rinsed 6-8× with EGM-2 with growth factors. Aortic rings were each placed in the center of a matrix (GELTREX™; Invitrogen Corp)-coated culture well. Aortic tissue was covered with 250 µl GELTREX™ and each well was incubated with 1 ml EGM-2 with growth factors supplemented for 24 hours at 37° C., 5% CO$_2$.

Figure 9:
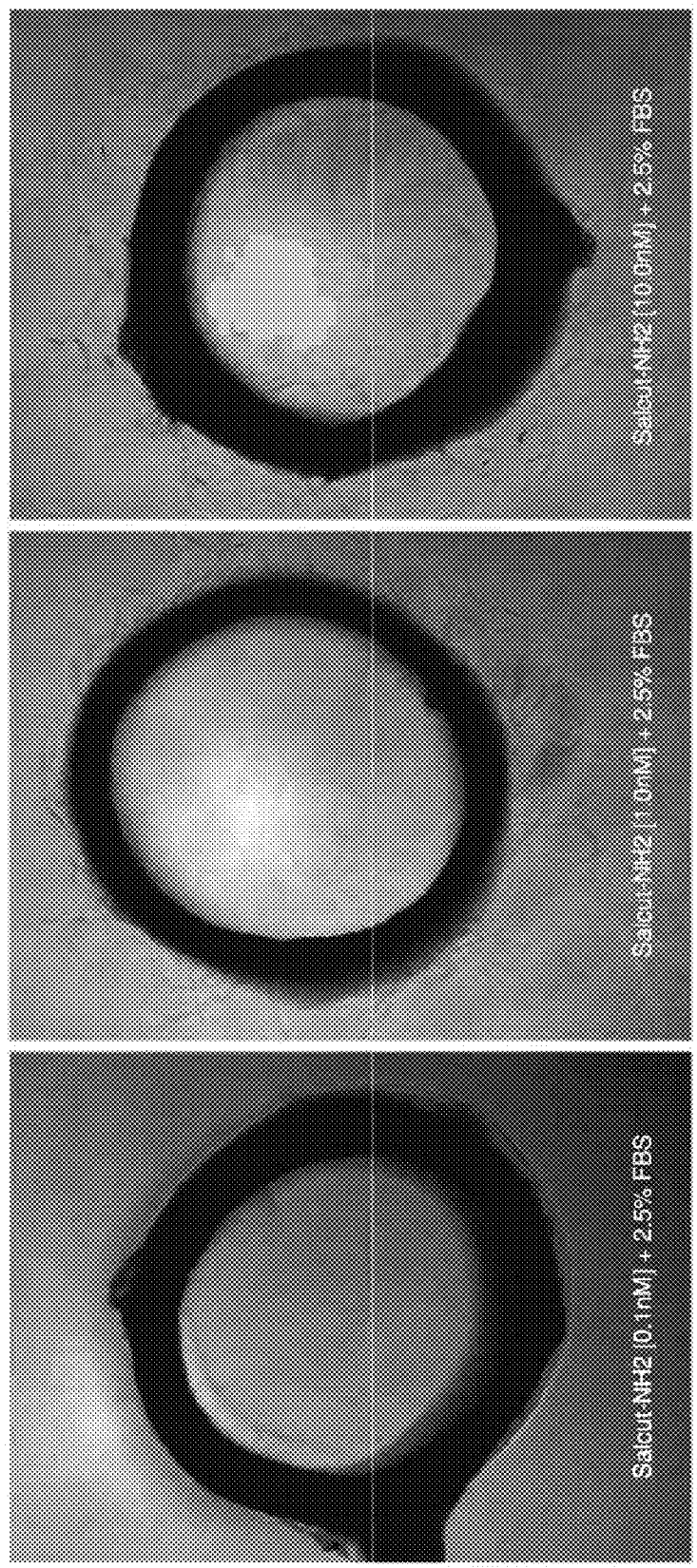
FIG. 9 is a series of images demonstrating the dose response of apelin 36 (42-57) (salcut-$NH_2$) on aortic ring vessel outcropping. The images show that the number of vessels formed increase with increasing concentration of apelin 36 (42-57) (salcut-$NH_2$). Vessels begin to form with the ring at 10 nM apelin 36 (42-57).

On day 1, media with growth factors was removed, 250 µl of media (without growth factors) with either 0.1 nM, 1.0 nM, or 10 nM of salcut-NH$_2$ was added to each well and incubated at 37° C., 5% CO$_2$ for 5-7 days. FIG. 9 demonstrates that increasing the concentration of salcut-NH$_2$ generated an increased number of vessels forming from the aortic ring. In addition, at the 10 nM salcut-NH$_2$ dose, vessels were beginning to form within the aortic ring.

Example 7

Production of Neutralizing Monoclonal Antibody Directed Against Apelin-36 (42-57) Amide (Salcut-NH$_2$)

This example described the production of a neutralizing monoclonal antibody against salcut-NH$_2$.

Hybridomas expressing a neutralizing monoclonal antibody against salcut-NH$_2$ are generated as described in Harlow and Lane (*Antibodies, A Laboratory Manual*, CSHL, New York, 1988). Hybridomas are screened for their ability to bind salcut-NH$_2$ but not salcut-OH or salcut-Gly, thus selecting for antibodies that exclusively target the carboxy-terminal amide. An antibody which binds at or near the carboxy-terminal amide suppresses peptide/receptor recognition and function as an antagonist. The resulting anti-salcut-NH$_2$ antibodies are evaluated in vitro and in vivo assay systems to confirm the neutralizing antibody's activity.

Example 8

Effect of APJ Antagonist on Salcut-NH$_2$-Mediated Endothelial Cell Proliferation This example describes the effect of an APJ peptide antagonist on salcut-NH$_2$-mediated endothelial cell proliferation.

Figures 13A, 13B:
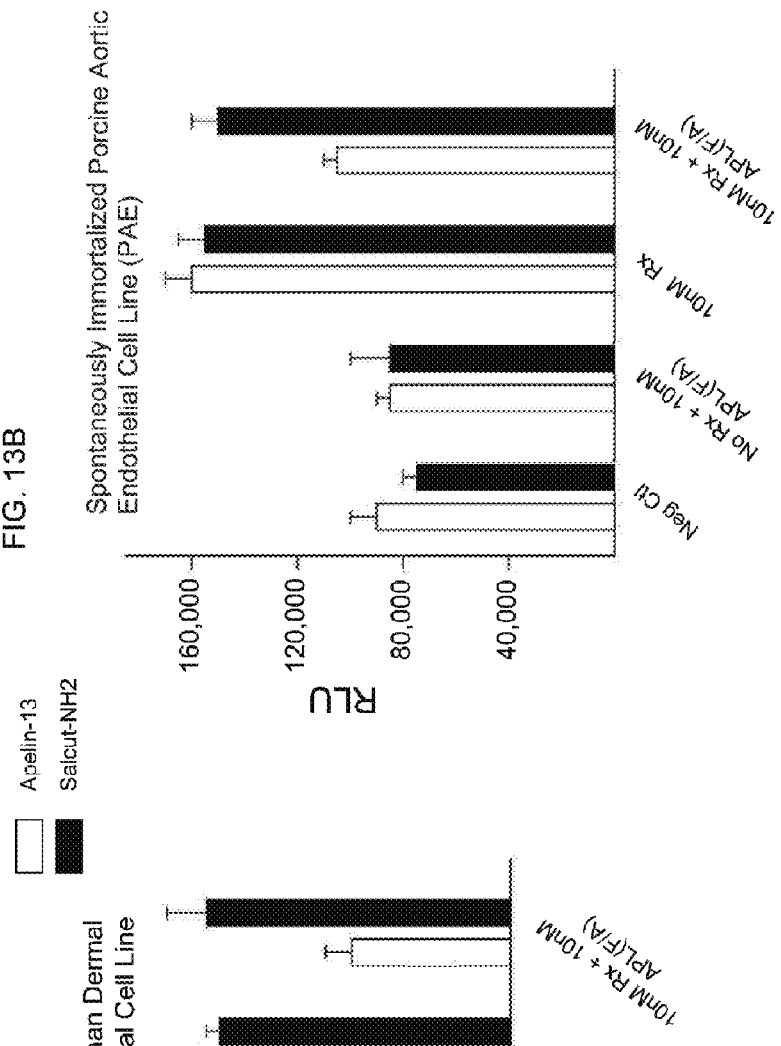
FIG. 13A is a graph showing the proliferative response of SV40 immortalized human dermal microvascular endothelial cell line HMEC-1 to apelin-13 and salcut-NH2 in the presence or absence of APJ receptor antagonist apelin-13 (F13A) (also known as ala13-apelin).
FIG. 13B is a graph showing the proliferative response of the spontaneously immortalized rat aortic cell line PAE to apelin-13 and salcut-NH2 in the presence or absence of APJ receptor antagonist apelin-13 (F13A). Rx is apelin-13 or salcut-$NH_2$; APL (F/A) is apelin-13 (F13A); RLU is relative luminescent units.

Endothelial cell proliferation assays were performed as described above with both spontaneously immortalized porcine aortic endothelial (PAE) cells and SV40 immortalized human dermal microvascular endothelial (HMEC-1). FIG. 13A (HMEC-1 cells) and FIG. 13B (PAE cells) demonstrate that apelin-13(F13A) selectively inhibits apelin-13 mediated proliferation. However, cell proliferation regulated by Salcut- NH₂ is not blocked by apelin-13(F13A) (FIGS. 13A and 13B). These findings clearly demonstrate that Salcut-NH₂ does not initiate its biological effects through the APJ receptor, as is done by apelin-13 and instead mediates its effects through a different receptor or receptor complex.

Example 9

Identification of Salcut-NH₂ Receptor

This example describes the use of a biotinylated form of salcut-NH₂ to identify and isolate the salcut-NH₂ receptor.

Figure 14A:
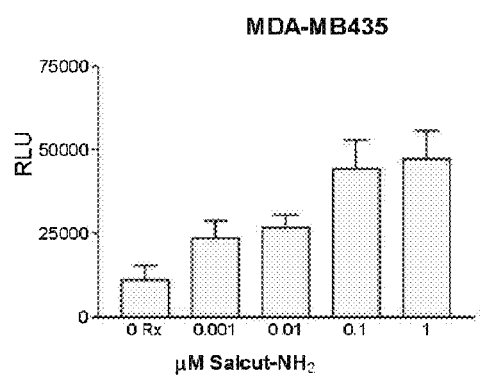
FIG. 14A shows the proliferative response of the MDA-MB43 human breast cancer cell line in the presence of salcut-$NH_2$ prepared by Princeton Biomolecules (Langhorne, Pa.).
Figure 14B:
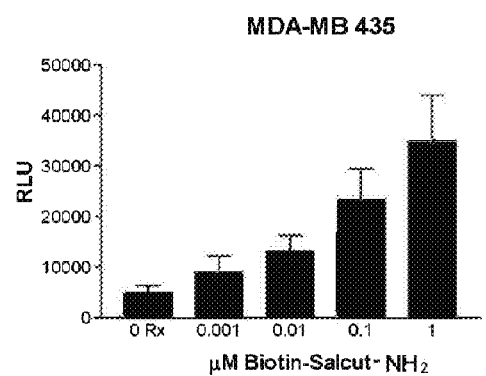
FIG. 14B shows the proliferative response of the MDA-MB43 human breast cancer cell line in the presence of biotinylated amino terminal derivative of salcut.
Figure 14C:
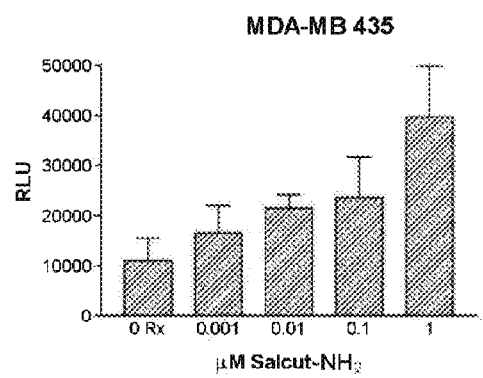
FIG. 14C shows the proliferative response of the MDA-MB43 human breast cancer cell line in the presence of salcut prepared by GenScript Corporation (Piscataway, N.Y.).

An N-terminal biotinylated salcut-NH₂ ligand was synthesized (a single biotin moiety was attached to the amino-terminal leucine residue). Validity of the chemical composition of the biotinylated salcut-NH₂ was accomplished using amino acid sequence analysis and MADLI-TOF mass spectrometry characterization. Comparison studies on human breast cancer cell line MDA-MB-435 show that salcut-NH₂ produced by two different manufacturers (FIGS. 14A and 14C) and biotinylated salcut (FIG. 14B) compounds are equipotent in proliferation assays (FIG. 14A-14C). In addition, the MDA-MB-435 cells demonstrate a large change in response in the presence of different concentrations of the salcut-NH₂ or biotinylated salcut over a dose range of 1 nM to 1 uM (FIG. 14A-14C).

The biotinylated amino terminal derivative of salcut-NH₂ bound to cells demonstrates high intensity fluorescent labeling. This binding can be inhibited by administering unlabeled salcut-NH₂ to the cells in the presence of biotinylated salcut-NH₂, indicating the specificity of binding of the biotinylated salcut-NH₂. Salcut-NH₂ is used in combination with ALEXA FLUOR® 488 streptavidin to enrich MDA-MB-345 cells for high cognate receptor expression via FACS sorting. Such high receptor expressing cells serve as a source of solubilized biotin-Salcut-NH₂/receptor complexes. The enriched high-intensity salcut-NH₂ receptor expressing cells are isolated, and membranes isolated and purified by sedimentation centrifugation. Isolated membranes are solubilized with a non-ionic detergent and micelle biotin ligand/receptor complex for salcut-NH₂ is isolated on a streptavidin column. The solid phased ligand/receptor complex is uncoupled using a mild acid wash (0.1M glycine, pH 3.0) and the receptor protein eluate rapidly neutralized (pH 7.0) with 1.0M ammonium hydroxide. The sample with the receptor protein is further fractionated using routine polyacrylamide gel electrophoresis and resulting protein bands assessed by MALDI MS/MS for amino acid sequence determination. Protein/molecular database analysis of resulting amino acid sequences is used to identify known or orphan receptor entities. Transfection studies with non-responsive cell lines (for example A549) are performed to confirm functionality of the receptor.

Example 10

Identification of Salcut-NH₂ Signal Transduction Pathway

This example describes the identification of the salcut-NH₂ signal transduction pathway.

Studies with MDA-MB-435 using cholera or pertussis toxin inhibitors determine if salcut-NH₂ proliferative activity is mediated through a G-coupled protein receptor (GCPR). In similar studies, Chinese Hamster Ovary (CHO) target cells are transfected with about 200 known and orphaned GCPRs linked to a beta-galactosidase (beta-gal) reporter. When the transfected receptor is activated with an appropriate ligand, the reported cells are turned on to express beta-gal and are visually identified by the addition of a color substrate. Hence, using this receptor panning technique it is possible to identify a specific GCPR for salcut-NH₂ in the CHO cell library. The identified GCPR is transfected into A549 cells (which are non-responsive in the proliferation assays discussed above) to determine if growth function is restored when the cells are exposed to salcut-NH₂. Many of the GCPRs have known signal transduction pathways and inhibitors to these pathways will identify which signal transduction avenue is required for salcut-NH₂ induced cell growth.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. An isolated polypeptide, the amino acid sequence of which consists of SEQ ID NO: 19 (salcut-NH$_2$).

2. An isolated polypeptide, comprising the polypeptide of claim 1, wherein the amino terminal end of the amino acid sequence is attached to a heterologous amino acid sequence, label, or reporter molecule.

3. A pharmaceutical composition, comprising the polypeptide of claim 1 in a pharmaceutically acceptable carrier.

* * * * *

```
SEQUENCE LISTING

<160> NUMBER OF SEQ ID NOS: 43

<210> SEQ ID NO 1
<211> LENGTH: 234
<212> TYPE: DNA
<213> ORGANISM: homo sapiens

<400> SEQUENCE: 1
atgaatctgc ggctctgcgt gcaggcgctc ctgctgctct ggctctcctt gaccgcggtg      60
tgtggagggt ccctgatgcc gcttcccgat gggaatgggc tggaagacgg caatgtccgc     120
cacctggtgc agcccagagg gtcaaggaat gggccagggc cctggcaggg aggtcggagg     180
aaattccgcc gccagcggcc ccgcctctcc cataagggac ccatgccttt ctga           234

<210> SEQ ID NO 2
<211> LENGTH: 234
<212> TYPE: DNA
<213> ORGANISM: Canis familiaris
```

<400> SEQUENCE: 2

```
atgaatctgc ggcgctgcgt gcaggcgctc ctgctgctct ggctctctct gaccgcggcg    60
tgtggagggc cgctgctgca gccttctgac ggcaaggcgc tggaggaagg caatatccgc   120
cacctggtgc agcccagagg ctcgagaaac ggaccggggc cctggcaggg cggtcggaag   180
aaatttcgcc gtcagcggcc acgcctctcc cataagggcc ccatgccttt ctga         234
```

<210> SEQ ID NO 3
<211> LENGTH: 234
<212> TYPE: DNA
<213> ORGANISM: bos taurus

<400> SEQUENCE: 3

```
atgaatctgc ggcgctgcgt gcaggcgctc ctgctgctct ggctctgcct gagcgcggtg    60
tgcggaggac ccctgctgca gacttctgac gggaaggaga tggaagaagg caccatccga   120
tacctggtgc agcccagggg gccgaggagc ggcccaggcc cctggcaggg aggtcggagg   180
aagttccggc gccagcggcc acgcctctcc cacaagggtc ccatgccttt ctga         234
```

<210> SEQ ID NO 4
<211> LENGTH: 234
<212> TYPE: DNA
<213> ORGANISM: rattus norvegicus

<400> SEQUENCE: 4

```
atgaatctga gtttctgcgt gcaggcgctg ctgctgctct ggctctcctt gactgccgtg    60
tgtggagtgc cactgatgct gcctccagat gggaaagggc tagaagaagg caacatgcgc   120
tacctggtga agcccagaac ttcgaggact ggaccagggg cctggcaggg aggcaggagg   180
aaatttcgca gacagcggcc ccgtctctcc cataagggac ccatgccttt ctaa         234
```

<210> SEQ ID NO 5
<211> LENGTH: 234
<212> TYPE: DNA
<213> ORGANISM: mus musculus

<400> SEQUENCE: 5

```
atgaatctga ggctctgcgt gcaggcgctg ctgctgctct ggctctcctt gactgcagtt    60
tgtggagtgc cactgatgtt gcctccagat ggaacaggac tagaagaagg aagcatgcgc   120
tacctggtga agcccagaac ttcgaggact ggaccaggag cctggcaggg aggcaggagg   180
aaatttcgca gacagcgccc ccggctctcc cataagggcc ccatgccttt ctaa         234
```

<210> SEQ ID NO 6
<211> LENGTH: 231
<212> TYPE: DNA
<213> ORGANISM: Monodelphis domestica

<400> SEQUENCE: 6

```
atgaatttgc ggcgctgcct gcaggcgctg ctcctgctct ggctctccct ggcttcggtt    60
tgcggagggc ccctggtgga gccatcagac aggaaggagc tggaggaagg gaacattcga   120
accctggtgc agcccaaagg agcaagagtt ggaggaccct ggccaggtgg taggaggaag   180
ttccgaaggc agcgtccccg tctctcccac aaaggcccca tgcctttctg a            231
```

<210> SEQ ID NO 7
<211> LENGTH: 234
<212> TYPE: DNA
<213> ORGANISM: Danio rerio

```
<400> SEQUENCE: 7
atgaatgtga agatcttgac gctggtgatt gtgctggtgg tttctctgct gtgttcagcc    60
agtgctggtc caatggcctc caccgagcat agcaaagaga tcgaggaggt gggaagcatg   120
aggactcctt tgcggcagaa tcccgctcga gctggccgga gccaaagacc cgctggctgg   180
aggaggagac ccctcgacc ccgcctctcc cataagggc ccatgccatt ctag           234
```

```
<210> SEQ ID NO 8
<211> LENGTH: 77
<212> TYPE: PRT
<213> ORGANISM: homo sapiens

<400> SEQUENCE: 8
```

| Met | Asn | Leu | Arg | Leu | Cys | Val | Gln | Ala | Leu | Leu | Leu | Trp | Leu | Ser |
|---|---|---|---|---|---|---|---|---|---|---|---|---|---|---|
| 1 | | | | 5 | | | | | 10 | | | | | 15 |

| Leu | Thr | Ala | Val | Cys | Gly | Gly | Ser | Leu | Met | Pro | Leu | Pro | Asp | Gly | Asn |
|---|---|---|---|---|---|---|---|---|---|---|---|---|---|---|---|
| | | | 20 | | | | | 25 | | | | | 30 | | |

| Gly | Leu | Glu | Asp | Gly | Asn | Val | Arg | His | Leu | Val | Gln | Pro | Arg | Gly | Ser |
|---|---|---|---|---|---|---|---|---|---|---|---|---|---|---|---|
| | | 35 | | | | | 40 | | | | | 45 | | | |

| Arg | Asn | Gly | Pro | Gly | Pro | Trp | Gln | Gly | Gly | Arg | Arg | Lys | Phe | Arg | Arg |
|---|---|---|---|---|---|---|---|---|---|---|---|---|---|---|---|
| 50 | | | | | 55 | | | | | 60 | | | | | |

| Gln | Arg | Pro | Arg | Leu | Ser | His | Lys | Gly | Pro | Met | Pro | Phe |
|---|---|---|---|---|---|---|---|---|---|---|---|---|
| 65 | | | | | 70 | | | | | 75 | | |

```
<210> SEQ ID NO 9
<211> LENGTH: 77
<212> TYPE: PRT
<213> ORGANISM: Canis familiaris

<400> SEQUENCE: 9
```

| Met | Asn | Leu | Arg | Arg | Cys | Val | Gln | Ala | Leu | Leu | Leu | Trp | Leu | Ser |
|---|---|---|---|---|---|---|---|---|---|---|---|---|---|---|
| 1 | | | | 5 | | | | | 10 | | | | | 15 |

| Leu | Thr | Ala | Ala | Cys | Gly | Gly | Pro | Leu | Leu | Gln | Pro | Ser | Asp | Gly | Lys |
|---|---|---|---|---|---|---|---|---|---|---|---|---|---|---|---|
| | | | 20 | | | | | 25 | | | | | 30 | | |

| Ala | Leu | Glu | Glu | Gly | Asn | Ile | Arg | His | Leu | Val | Gln | Pro | Arg | Gly | Ser |
|---|---|---|---|---|---|---|---|---|---|---|---|---|---|---|---|
| | | 35 | | | | | 40 | | | | | 45 | | | |

| Arg | Asn | Gly | Pro | Gly | Pro | Trp | Gln | Gly | Gly | Arg | Lys | Lys | Phe | Arg | Arg |
|---|---|---|---|---|---|---|---|---|---|---|---|---|---|---|---|
| 50 | | | | | 55 | | | | | 60 | | | | | |

| Gln | Arg | Pro | Arg | Leu | Ser | His | Lys | Gly | Pro | Met | Pro | Phe |
|---|---|---|---|---|---|---|---|---|---|---|---|---|
| 65 | | | | | 70 | | | | | 75 | | |

```
<210> SEQ ID NO 10
<211> LENGTH: 77
<212> TYPE: PRT
<213> ORGANISM: bos taurus

<400> SEQUENCE: 10
```

| Met | Asn | Leu | Arg | Arg | Cys | Val | Gln | Ala | Leu | Leu | Leu | Trp | Leu | Cys |
|---|---|---|---|---|---|---|---|---|---|---|---|---|---|---|
| 1 | | | | 5 | | | | | 10 | | | | | 15 |

| Leu | Ser | Ala | Val | Cys | Gly | Gly | Pro | Leu | Leu | Gln | Thr | Ser | Asp | Gly | Lys |
|---|---|---|---|---|---|---|---|---|---|---|---|---|---|---|---|
| | | | 20 | | | | | 25 | | | | | 30 | | |

| Glu | Met | Glu | Glu | Gly | Thr | Ile | Arg | Tyr | Leu | Val | Gln | Pro | Arg | Gly | Pro |
|---|---|---|---|---|---|---|---|---|---|---|---|---|---|---|---|
| | | 35 | | | | | 40 | | | | | 45 | | | |

| Arg | Ser | Gly | Pro | Gly | Pro | Trp | Gln | Gly | Gly | Arg | Lys | Phe | Arg | Arg |
|---|---|---|---|---|---|---|---|---|---|---|---|---|---|---|
| 50 | | | | | 55 | | | | | 60 | | | | | |

| Gln | Arg | Pro | Arg | Leu | Ser | His | Lys | Gly | Pro | Met | Pro | Phe |
|---|---|---|---|---|---|---|---|---|---|---|---|---|
| 65 | | | | | 70 | | | | | 75 | | |

```
<210> SEQ ID NO 11
<211> LENGTH: 77
<212> TYPE: PRT
<213> ORGANISM: rattus norvegicus

<400> SEQUENCE: 11
```

| Met | Asn | Leu | Ser | Phe | Cys | Val | Gln | Ala | Leu | Leu | Leu | Trp | Leu | Ser |
|---|---|---|---|---|---|---|---|---|---|---|---|---|---|---|
| 1 | | | | 5 | | | | | 10 | | | | | 15 |

| Leu | Thr | Ala | Val | Cys | Gly | Val | Pro | Leu | Met | Leu | Pro | Pro | Asp | Gly | Lys |
|---|---|---|---|---|---|---|---|---|---|---|---|---|---|---|---|
| | | | 20 | | | | | 25 | | | | | 30 | | |

| Gly | Leu | Glu | Glu | Gly | Asn | Met | Arg | Tyr | Leu | Val | Lys | Pro | Arg | Thr | Ser |
|---|---|---|---|---|---|---|---|---|---|---|---|---|---|---|---|
| | | | | 35 | | | | | 40 | | | | | 45 | |

| Arg | Thr | Gly | Pro | Gly | Ala | Trp | Gln | Gly | Gly | Arg | Arg | Lys | Phe | Arg | Arg |
|---|---|---|---|---|---|---|---|---|---|---|---|---|---|---|---|
| | 50 | | | | | 55 | | | | | 60 | | | | |

| Gln | Arg | Pro | Arg | Leu | Ser | His | Lys | Gly | Pro | Met | Pro | Phe |
|---|---|---|---|---|---|---|---|---|---|---|---|---|
| 65 | | | | | 70 | | | | | 75 | | |

```
<210> SEQ ID NO 12
<211> LENGTH: 77
<212> TYPE: PRT
<213> ORGANISM: mus musculus

<400> SEQUENCE: 12
```

| Met | Asn | Leu | Arg | Leu | Cys | Val | Gln | Ala | Leu | Leu | Leu | Trp | Leu | Ser |
|---|---|---|---|---|---|---|---|---|---|---|---|---|---|---|
| 1 | | | | 5 | | | | | 10 | | | | | 15 |

| Leu | Thr | Ala | Val | Cys | Gly | Val | Pro | Leu | Met | Leu | Pro | Pro | Asp | Gly | Thr |
|---|---|---|---|---|---|---|---|---|---|---|---|---|---|---|---|
| | | | 20 | | | | | 25 | | | | | 30 | | |

| Gly | Leu | Glu | Glu | Gly | Ser | Met | Arg | Tyr | Leu | Val | Lys | Pro | Arg | Thr | Ser |
|---|---|---|---|---|---|---|---|---|---|---|---|---|---|---|---|
| | | | | 35 | | | | | 40 | | | | | 45 | |

| Arg | Thr | Gly | Pro | Gly | Ala | Trp | Gln | Gly | Gly | Arg | Arg | Lys | Phe | Arg | Arg |
|---|---|---|---|---|---|---|---|---|---|---|---|---|---|---|---|
| | 50 | | | | | 55 | | | | | 60 | | | | |

| Gln | Arg | Pro | Arg | Leu | Ser | His | Lys | Gly | Pro | Met | Pro | Phe |
|---|---|---|---|---|---|---|---|---|---|---|---|---|
| 65 | | | | | 70 | | | | | 75 | | |

```
<210> SEQ ID NO 13
<211> LENGTH: 76
<212> TYPE: PRT
<213> ORGANISM: Monodelphis domesticaulus

<400> SEQUENCE: 13
```

| Met | Asn | Leu | Arg | Arg | Cys | Leu | Gln | Ala | Leu | Leu | Leu | Trp | Leu | Ser |
|---|---|---|---|---|---|---|---|---|---|---|---|---|---|---|
| 1 | | | | 5 | | | | | 10 | | | | | 15 |

| Leu | Ala | Ser | Val | Cys | Gly | Gly | Pro | Leu | Val | Glu | Pro | Ser | Asp | Arg | Lys |
|---|---|---|---|---|---|---|---|---|---|---|---|---|---|---|---|
| | | | 20 | | | | | 25 | | | | | 30 | | |

| Glu | Leu | Glu | Glu | Gly | Asn | Ile | Arg | Thr | Leu | Val | Gln | Pro | Lys | Gly | Ala |
|---|---|---|---|---|---|---|---|---|---|---|---|---|---|---|---|
| | | | | 35 | | | | | 40 | | | | | 45 | |

| Arg | Val | Gly | Gly | Pro | Trp | Pro | Gly | Gly | Arg | Lys | Phe | Arg | Arg | Gln |
|---|---|---|---|---|---|---|---|---|---|---|---|---|---|---|
| | 50 | | | | | 55 | | | | | 60 | | | |

| Arg | Pro | Arg | Leu | Ser | His | Lys | Gly | Pro | Met | Pro | Phe |
|---|---|---|---|---|---|---|---|---|---|---|---|
| 65 | | | | | 70 | | | | | 75 | |

```
<210> SEQ ID NO 14
<211> LENGTH: 77
<212> TYPE: PRT
<213> ORGANISM: Danio rerio

<400> SEQUENCE: 14
```

| Met | Asn | Val | Lys | Ile | Leu | Thr | Leu | Val | Ile | Val | Leu | Val | Ser | Leu |
|---|---|---|---|---|---|---|---|---|---|---|---|---|---|---|

-continued

```
                1               5                  10                 15
Leu Cys Ser Ala Ser Ala Gly Pro Met Ala Ser Thr Glu His Ser Lys
                20                 25                 30
Glu Ile Glu Glu Val Gly Ser Met Arg Thr Pro Leu Arg Gln Asn Pro
                35                 40                 45
Ala Arg Ala Gly Arg Ser Gln Arg Pro Ala Gly Trp Arg Arg Arg
        50                 55                 60
Pro Arg Pro Arg Leu Ser His Lys Gly Pro Met Pro Phe
65                 70                 75

<210> SEQ ID NO 15
<211> LENGTH: 36
<212> TYPE: PRT
<213> ORGANISM: homo sapiens

<400> SEQUENCE: 15

Leu Val Gln Pro Arg Gly Ser Arg Asn Gly Pro Gly Pro Trp Gln Gly
1               5                  10                 15
Gly Arg Arg Lys Phe Arg Arg Gln Arg Pro Arg Leu Ser His Lys Gly
                20                 25                 30
Pro Met Pro Phe
        35

<210> SEQ ID NO 16
<211> LENGTH: 17
<212> TYPE: PRT
<213> ORGANISM: homo sapiens

<400> SEQUENCE: 16

Lys Phe Arg Arg Gln Arg Pro Arg Leu Ser His Lys Gly Pro Met Pro
1               5                  10                 15
Phe

<210> SEQ ID NO 17
<211> LENGTH: 13
<212> TYPE: PRT
<213> ORGANISM: homo sapiens

<400> SEQUENCE: 17

Gln Arg Pro Arg Leu Ser His Lys Gly Pro Met Pro Phe
1               5                  10

<210> SEQ ID NO 18
<211> LENGTH: 16
<212> TYPE: PRT
<213> ORGANISM: homo sapiens

<400> SEQUENCE: 18

Leu Val Gln Pro Arg Gly Ser Arg Asn Gly Pro Gly Pro Trp Gln Gly
1               5                  10                 15

<210> SEQ ID NO 19
<211> LENGTH: 16
<212> TYPE: PRT
<213> ORGANISM: homo sapiens
<220> FEATURE:
<221> NAME/KEY: MOD_RES
<222> LOCATION: (16)..(16)
<223> OTHER INFORMATION: AMIDATION

<400> SEQUENCE: 19

Leu Val Gln Pro Arg Gly Ser Arg Asn Gly Pro Gly Pro Trp Gln Gly
```

```
1               5                  10                  15
```

<210> SEQ ID NO 20
<211> LENGTH: 17
<212> TYPE: PRT
<213> ORGANISM: homo sapiens

<400> SEQUENCE: 20

```
Leu Val Gln Pro Arg Gly Ser Arg Asn Gly Pro Gly Pro Trp Gln Gly
1               5                  10                  15

Gly
```

<210> SEQ ID NO 21
<211> LENGTH: 16
<212> TYPE: PRT
<213> ORGANISM: Canis familiaris

<400> SEQUENCE: 21

```
Leu Val Gln Pro Arg Gly Ser Arg Asn Gly Pro Gly Pro Trp Gln Gly
1               5                  10                  15
```

<210> SEQ ID NO 22
<211> LENGTH: 16
<212> TYPE: PRT
<213> ORGANISM: Canis familiaris
<220> FEATURE:
<221> NAME/KEY: MOD_RES
<222> LOCATION: (16)..(16)
<223> OTHER INFORMATION: AMIDATION

<400> SEQUENCE: 22

```
Leu Val Gln Pro Arg Gly Ser Arg Asn Gly Pro Gly Pro Trp Gln Gly
1               5                  10                  15
```

<210> SEQ ID NO 23
<211> LENGTH: 17
<212> TYPE: PRT
<213> ORGANISM: Canis familiaris

<400> SEQUENCE: 23

```
Leu Val Gln Pro Arg Gly Ser Arg Asn Gly Pro Gly Pro Trp Gln Gly
1               5                  10                  15

Gly
```

<210> SEQ ID NO 24
<211> LENGTH: 16
<212> TYPE: PRT
<213> ORGANISM: bos taurus

<400> SEQUENCE: 24

```
Leu Val Gln Pro Arg Gly Pro Arg Ser Gly Pro Gly Pro Trp Gln Gly
1               5                  10                  15
```

<210> SEQ ID NO 25
<211> LENGTH: 16
<212> TYPE: PRT
<213> ORGANISM: bos taurus
<220> FEATURE:
<221> NAME/KEY: MOD_RES
<222> LOCATION: (16)..(16)
<223> OTHER INFORMATION: AMIDATION

<400> SEQUENCE: 25

```
Leu Val Gln Pro Arg Gly Pro Arg Ser Gly Pro Gly Pro Trp Gln Gly
1               5                  10                  15
```

<210> SEQ ID NO 26
<211> LENGTH: 17
<212> TYPE: PRT
<213> ORGANISM: bos taurus

<400> SEQUENCE: 26

Leu Val Gln Pro Arg Gly Pro Arg Ser Gly Pro Gly Pro Trp Gln Gly
1               5                   10                  15

Gly

<210> SEQ ID NO 27
<211> LENGTH: 16
<212> TYPE: PRT
<213> ORGANISM: rattus norvegicus

<400> SEQUENCE: 27

Leu Val Lys Pro Arg Thr Ser Arg Thr Gly Pro Gly Ala Trp Gln Gly
1               5                   10                  15

<210> SEQ ID NO 28
<211> LENGTH: 16
<212> TYPE: PRT
<213> ORGANISM: rattus norvegicus
<220> FEATURE:
<221> NAME/KEY: MOD_RES
<222> LOCATION: (16)..(16)
<223> OTHER INFORMATION: AMIDATION

<400> SEQUENCE: 28

Leu Val Lys Pro Arg Thr Ser Arg Thr Gly Pro Gly Ala Trp Gln Gly
1               5                   10                  15

<210> SEQ ID NO 29
<211> LENGTH: 17
<212> TYPE: PRT
<213> ORGANISM: rattus norvegicus
<220> FEATURE:
<221> NAME/KEY: MOD_RES
<222> LOCATION: (16)..(16)
<223> OTHER INFORMATION: AMIDATION

<400> SEQUENCE: 29

Leu Val Lys Pro Arg Thr Ser Arg Thr Gly Pro Gly Ala Trp Gln Gly
1               5                   10                  15

Gly

<210> SEQ ID NO 30
<211> LENGTH: 16
<212> TYPE: PRT
<213> ORGANISM: mus musculus

<400> SEQUENCE: 30

Leu Val Lys Pro Arg Thr Ser Arg Thr Gly Pro Gly Ala Trp Gln Gly
1               5                   10                  15

<210> SEQ ID NO 31
<211> LENGTH: 16
<212> TYPE: PRT
<213> ORGANISM: mus musculus
<220> FEATURE:
<221> NAME/KEY: MOD_RES
<222> LOCATION: (16)..(16)
<223> OTHER INFORMATION: AMIDATION

<400> SEQUENCE: 31

```
Leu Val Lys Pro Arg Thr Ser Arg Thr Gly Pro Gly Ala Trp Gln Gly
1               5                   10                  15

<210> SEQ ID NO 32
<211> LENGTH: 17
<212> TYPE: PRT
<213> ORGANISM: mus musculus

<400> SEQUENCE: 32

Leu Val Lys Pro Arg Thr Ser Arg Thr Gly Pro Gly Ala Trp Gln Gly
1               5                   10                  15

Gly

<210> SEQ ID NO 33
<211> LENGTH: 15
<212> TYPE: PRT
<213> ORGANISM: Monodelphis domesticaulus

<400> SEQUENCE: 33

Leu Val Gln Pro Lys Gly Ala Arg Val Gly Gly Pro Trp Pro Gly
1               5                   10                  15

<210> SEQ ID NO 34
<211> LENGTH: 15
<212> TYPE: PRT
<213> ORGANISM: Monodelphis domesticaulus
<220> FEATURE:
<221> NAME/KEY: MOD_RES
<222> LOCATION: (15)..(15)
<223> OTHER INFORMATION: AMIDATION

<400> SEQUENCE: 34

Leu Val Gln Pro Lys Gly Ala Arg Val Gly Gly Pro Trp Pro Gly
1               5                   10                  15

<210> SEQ ID NO 35
<211> LENGTH: 16
<212> TYPE: PRT
<213> ORGANISM: Monodelphis domesticaulus

<400> SEQUENCE: 35

Leu Val Gln Pro Lys Gly Ala Arg Val Gly Gly Pro Trp Pro Gly Gly
1               5                   10                  15

<210> SEQ ID NO 36
<211> LENGTH: 231
<212> TYPE: DNA
<213> ORGANISM: Xenopus laevis

<400> SEQUENCE: 36
atgaatctca gactttgggc actggcgctt ctgctcttca ttttaacctt gacttcagca      60
tttggagctc cactggctga aggctcagat aggaatgacg aagaacagaa tatccggaca     120
ctggtgaacc ccaaaatggt tcgtaactct gcacctcaac ggcaagcaaa ccgaagaaaa     180
ctcatacgtc aaagaccccg tctttcacac aagggcccaa tgcccttcta a              231

<210> SEQ ID NO 37
<211> LENGTH: 76
<212> TYPE: PRT
<213> ORGANISM: Xenopus laevis

<400> SEQUENCE: 37

Met Asn Leu Arg Leu Trp Ala Leu Ala Leu Leu Leu Phe Ile Leu Thr
```

```
                1               5                  10                  15
Leu Thr Ser Ala Phe Gly Ala Pro Leu Ala Glu Gly Ser Asp Arg Asn
            20                  25                  30

Asp Glu Glu Gln Asn Ile Arg Thr Leu Val Asn Pro Lys Met Val Arg
        35                  40                  45

Asn Ser Ala Pro Gln Arg Gln Ala Asn Arg Arg Lys Leu Ile Arg Gln
    50                  55                  60

Arg Pro Arg Leu Ser His Lys Gly Pro Met Pro Phe
65                  70                  75

<210> SEQ ID NO 38
<211> LENGTH: 17
<212> TYPE: PRT
<213> ORGANISM: homo sapiens

<400> SEQUENCE: 38

Cys Leu Val Gln Pro Arg Gly Ser Arg Asn Gly Pro Gly Pro Trp Gln
1               5                   10                  15

Gly

<210> SEQ ID NO 39
<211> LENGTH: 234
<212> TYPE: DNA
<213> ORGANISM: Macaca mulatta

<400> SEQUENCE: 39
atgaatctgc ggctctgcgt gcaggcgctc ctgctgctct ggctctcctt gaccgcggtg      60
tgtggagggc ccctgatgca gcttccctat gggaatgggc tggaagaggg caatgtccgc     120
cacctggtgc agcccagagg gtcgaggaac gggccagggc cctggcaggg aggtcgaagg     180
aaattccgcc gccagcggcc cgcctctccc ataagggac ccatgccttt ctga            234

<210> SEQ ID NO 40
<211> LENGTH: 77
<212> TYPE: PRT
<213> ORGANISM: Macaca mulatta

<400> SEQUENCE: 40

Met Asn Leu Arg Leu Cys Val Gln Ala Leu Leu Leu Trp Leu Ser
1               5                   10                  15

Leu Thr Ala Val Cys Gly Gly Pro Leu Met Gln Leu Pro Tyr Gly Asn
            20                  25                  30

Gly Leu Glu Glu Gly Asn Val Arg His Leu Val Gln Pro Arg Gly Ser
        35                  40                  45

Arg Asn Gly Pro Gly Pro Trp Gln Gly Gly Arg Arg Lys Phe Arg Arg
    50                  55                  60

Gln Arg Pro Arg Leu Ser His Lys Gly Pro Met Pro Phe
65                  70                  75

<210> SEQ ID NO 41
<211> LENGTH: 16
<212> TYPE: PRT
<213> ORGANISM: Macaca mulatta

<400> SEQUENCE: 41

Leu Val Gln Pro Arg Gly Ser Arg Asn Gly Pro Gly Pro Trp Gln Gly
1               5                   10                  15

<210> SEQ ID NO 42
```

```
<211> LENGTH: 16
<212> TYPE: PRT
<213> ORGANISM: Macaca mulatta
<220> FEATURE:
<221> NAME/KEY: MOD_RES
<222> LOCATION: (16)..(16)
<223> OTHER INFORMATION: AMIDATION

<400> SEQUENCE: 42

Leu Val Gln Pro Arg Gly Ser Arg Asn Gly Pro Gly Pro Trp Gln Gly
1               5                   10                  15

<210> SEQ ID NO 43
<211> LENGTH: 17
<212> TYPE: PRT
<213> ORGANISM: Macaca mulatta

<400> SEQUENCE: 43

Leu Val Gln Pro Arg Gly Ser Arg Asn Gly Pro Gly Pro Trp Gln Gly
1               5                   10                  15

Gly
```